(12) United States Patent
Venkataramani

(10) Patent No.: US 8,283,357 B2
(45) Date of Patent: Oct. 9, 2012

(54) CYCLOALKYLCARBAMATE BENZAMIDE ANILINE HDAC INHIBITOR COMPOUNDS

(75) Inventor: Chandrasekar Venkataramani, Redwood City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 276 days.

(21) Appl. No.: 12/795,575

(22) Filed: Jun. 7, 2010

(65) Prior Publication Data
US 2010/0311794 A1   Dec. 9, 2010

Related U.S. Application Data

(60) Provisional application No. 61/185,134, filed on Jun. 8, 2009.

(51) Int. Cl.
*A61K 31/4468* (2006.01)
*C07D 211/56* (2006.01)
(52) U.S. Cl. .......................................... 514/278; 546/16
(58) Field of Classification Search .................. 514/278; 546/16
See application file for complete search history.

(56) References Cited

U.S. PATENT DOCUMENTS

| | | | |
|---|---|---|---|
| 5,760,246 | A | 6/1998 | Biller et al. |
| 6,403,588 | B1 | 6/2002 | Hayakawa et al. |
| 7,253,204 | B2 | 8/2007 | Delorme et al. |
| 2002/0168761 | A1 | 11/2002 | Gour et al. |
| 2004/0006011 | A1 | 1/2004 | Gour et al. |
| 2005/0054850 | A1 | 3/2005 | Wu et al. |
| 2005/0187266 | A1 | 8/2005 | Su |
| 2005/0234066 | A1 | 10/2005 | Bailey et al. |
| 2005/0288282 | A1 | 12/2005 | Delorme et al. |
| 2006/0293320 | A1 | 12/2006 | Schmitz et al. |
| 2007/0093492 | A1 | 4/2007 | Jiaang et al. |
| 2007/0213330 | A1 | 9/2007 | Delorme et al. |
| 2009/0005374 | A1 | 1/2009 | Melvin, Jr. et al. |
| 2009/0076021 | A1 | 3/2009 | Plato |
| 2010/0009990 | A1 | 1/2010 | Venkataramani |
| 2010/0022543 | A1 | 1/2010 | Melvin, Jr. et al. |
| 2010/0029638 | A1 | 2/2010 | Melvin, Jr. et al. |
| 2010/0310500 | A1 | 12/2010 | Graupe et al. |

FOREIGN PATENT DOCUMENTS

| | | |
|---|---|---|
| CA | 2644933 A1 | 9/2007 |
| EP | 0847992 A1 | 6/1998 |
| EP | 1277754 A1 | 1/2003 |
| JP | 2003-313126 A | 11/2003 |
| JP | 2004-002826 A | 1/2004 |
| JP | 2007-001885 A | 1/2007 |
| WO | WO-97/26240 A1 | 7/1997 |
| WO | WO-00/18733 A1 | 4/2000 |
| WO | WO-01/14375 A1 | 3/2001 |
| WO | WO-01/19788 A2 | 3/2001 |
| WO | WO-01/53331 A2 | 7/2001 |
| WO | WO-01/56989 A2 | 8/2001 |
| WO | WO-01/83481 A1 | 11/2001 |
| WO | WO-02/00651 A2 | 1/2002 |
| WO | WO-02/26712 A2 | 4/2002 |
| WO | WO-02/34748 A1 | 5/2002 |
| WO | WO-02/46170 A2 | 6/2002 |
| WO | WO-02/065979 A2 | 8/2002 |
| WO | WO-02/066480 A2 | 8/2002 |
| WO | WO-02/066481 A1 | 8/2002 |
| WO | WO-03/000682 A1 | 1/2003 |
| WO | WO-03/000689 A1 | 1/2003 |
| WO | WO-03/002524 A2 | 1/2003 |
| WO | WO-03/031446 A1 | 4/2003 |
| WO | WO-03/041649 A2 | 5/2003 |
| WO | WO-03/084948 A1 | 10/2003 |
| WO | WO-03/084997 A1 | 10/2003 |
| WO | WO-03/099221 A2 | 12/2003 |
| WO | WO-03/099817 A1 | 12/2003 |
| WO | WO-03/103151 A1 | 12/2003 |
| WO | WO-2004/021989 A2 | 3/2004 |
| WO | WO-2004/035525 A1 | 4/2004 |
| WO | WO-2004/039325 A2 | 5/2004 |
| WO | WO-2004/041191 A2 | 5/2004 |
| WO | WO-2004/048343 A1 | 6/2004 |
| WO | WO-2004/060318 A2 | 7/2004 |
| WO | WO-2004/069133 A2 | 8/2004 |
| WO | WO-2004/069803 A2 | 8/2004 |
| WO | WO-2004/076452 A1 | 9/2004 |

(Continued)

OTHER PUBLICATIONS

Acharya et al. (2005) "Rational Development of Histone Deacetylase Inhibitors as Anticancer Agents" *A Review, Molecular Pharmacology* 68:917-932.
Alam et al. (2007) "Synthesis and SAR of Aminopyriidines as Novel c-Jun N-terminal Kinase (JNK) Inhibitors" *Science Direct, Bioorganic & Medicinal Chemistry Letters* 17:3463-3467.
Buggy et al. (2006) "CRA-024781: A Novel Synthetic Inhibitor of Histone Decetylase Enzymes with Antitumor Activity In Vitro and In Vivo" *Mol. Cancer Ther.* 5:1309-1317.
Bush et al. (2009) "Targeting Histone Deacetylases for Heart Failure" *Myogen, Inc.* 1-39.

(Continued)

*Primary Examiner* — Taofiq A Solola
(74) *Attorney, Agent, or Firm* — J. Elin Hartrum

(57) ABSTRACT

The present invention provides a compound of general Formula (I) having histone deacetylase (HDAC) inhibitory activity, a pharmaceutical composition comprising the compound, and a method useful to treat diseases using the compound.

Formula (I)

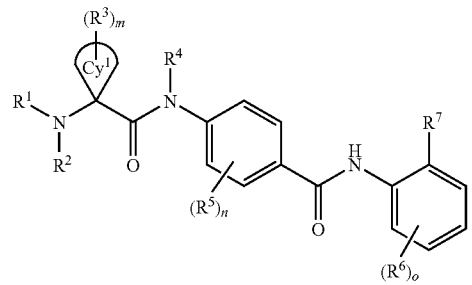

35 Claims, No Drawings

FOREIGN PATENT DOCUMENTS

| | | |
|---|---|---|
| WO | WO-2004/080390 A2 | 9/2004 |
| WO | WO-2004/084901 A1 | 10/2004 |
| WO | WO-2004/092115 A2 | 10/2004 |
| WO | WO-2004/092145 A1 | 10/2004 |
| WO | WO-2004/110350 A2 | 12/2004 |
| WO | WO-2005/006945 A2 | 1/2005 |
| WO | WO-2005/030140 A2 | 4/2005 |
| WO | WO-2005/030705 A1 | 4/2005 |
| WO | WO-2005/046594 A2 | 5/2005 |
| WO | WO-2005/054850 A2 | 6/2005 |
| WO | WO-2005/060571 A2 | 7/2005 |
| WO | WO-2005/070180 A2 | 8/2005 |
| WO | WO-2005/077368 A2 | 8/2005 |
| WO | WO-2005/077373 A2 | 8/2005 |
| WO | WO-2005/082871 A2 | 9/2005 |
| WO | WO-2005/092899 A1 | 10/2005 |
| WO | WO-2005/102318 A1 | 11/2005 |
| WO | WO-2005/102325 A1 | 11/2005 |
| WO | WO-2005/102326 A2 | 11/2005 |
| WO | WO-2005/102346 A2 | 11/2005 |
| WO | WO-2005/102455 A2 | 11/2005 |
| WO | WO-2005/103022 A1 | 11/2005 |
| WO | WO-2005/112920 A1 | 12/2005 |
| WO | WO-2005/115304 A2 | 12/2005 |
| WO | WO-2005/115385 A1 | 12/2005 |
| WO | WO-2006/010750 A1 | 2/2006 |
| WO | WO-2006/038001 A1 | 4/2006 |
| WO | WO-2006/044509 A1 | 4/2006 |
| WO | WO-2006/058007 A2 | 6/2006 |
| WO | WO-2006/058905 A1 | 6/2006 |
| WO | WO-2006/064251 A1 | 6/2006 |
| WO | WO-2006/070943 A1 | 7/2006 |
| WO | WO-2006/077401 A1 | 7/2006 |
| WO | WO-2006/104983 A1 | 10/2006 |
| WO | WO-2006/108059 A1 | 10/2006 |
| WO | WO-2006/122011 A2 | 11/2006 |
| WO | WO-2007/008664 A1 | 1/2007 |
| WO | WO-2007/026251 A2 | 3/2007 |
| WO | WO-2007/030362 A1 | 3/2007 |
| WO | WO-2007/036732 A1 | 4/2007 |
| WO | WO-2007/037187 A1 | 4/2007 |
| WO | WO-2007/040440 A1 | 4/2007 |
| WO | WO-2007/055941 A2 | 5/2007 |
| WO | WO-2007/076034 A2 | 7/2007 |
| WO | WO-2007/076035 A2 | 7/2007 |
| WO | WO-2007/079185 A2 | 7/2007 |
| WO | WO-2007/087129 A2 | 8/2007 |
| WO | WO-2007/087717 A1 | 8/2007 |
| WO | WO-2007/093492 A1 | 8/2007 |
| WO | WO-2007/095124 A2 | 8/2007 |
| WO | WO-2007/100795 A2 | 9/2007 |
| WO | WO-2007/106192 A2 | 9/2007 |
| WO | WO-2007/127137 A2 | 11/2007 |
| WO | WO-2007/135036 A1 | 11/2007 |
| WO | WO-2008/033743 A1 | 3/2008 |
| WO | WO-09/002534 A1 | 12/2008 |
| WO | WO-2009/079391 A1 | 6/2009 |
| WO | WO-2010/009139 A2 | 1/2010 |
| WO | WO-2010/009155 A2 | 1/2010 |
| WO | WO-2010/009166 A1 | 1/2010 |
| WO | WO-2010/014611 A1 | 2/2010 |

OTHER PUBLICATIONS

Feng et al. (2006) "Synthesis and SAR of 2-(4-fluorophenyl)-3-pyrimidin-4-ylimidazo[1,2-a]pyridine Derivatives as Anticoccidial Agents" *Science Direct, Bioorganic & Medicinal Chemistry Letters* 16:5978-5981.

Gudmundsson et al. (2007) "Imidazo[1,2-a]ayridines With Potent Activity Against Herpesviruses" *Scienc Direct, Bioorganic & Medicinal Chemistry Letters* 17:2735-2739.

Hayakawa et al. (2007) "Synthesis and Biological Evaluation of Imidazol[1,2-a]pyridine Derivatives As Novel PI3 Kinase p110a Inhibitors" *Science Direct, Bioorganic & Medicinal Chemistry* 15:403-412.

International Search Report for PCT/US2008/007963, International Filing Date Jun. 26, 2008, mailed Oct. 1, 2008.

International Search Report for PCT/US2008/086643, International Filing Date Dec. 12, 2008, mailed Mar. 23, 2009.

International Search Report for PCT/US2009/050558, International Filing Date Jul. 14, 2009, mailed Oct. 12, 2009.

International Search Report for PCT/US2009/050577, International Filing Date Jul. 14, 2009, mailed Nov. 11, 2009.

International Search Report for PCT/US2009/050595, International Filing Date Jul. 14, 2009, mailed Nov. 18, 2009.

International Search Report for PCT/US2009/051964, International Filing Date Jul. 28, 2009, mailed Oct. 2, 2009.

Liang et al. (2007) "Synthesis and SAR Studies of Potent Imidazopyridine Anticoccidial Agents" *Science Direct, Bioorganic & Medicinal Chemistry Letters* 17:3558-3561.

Mahboobi et al. (2007) "2-Aroylindoles and w-Arolbenzofurans with N-Hydroxyacrylamide Substructures as a Novel Series of Rationally Designed Histone Deacetylase Inhibitors" *American Chemical Society* A-N.

Marcou et al. (2007) "Optimizing Fragment and Scaffold Docking by Use of Molecular Interaction Fingerprints" *Journal of Chemistry Inf. Model* 47(1):195-207.

Moradeli et al. (2005) "Histone Deacetylase Inhibitors" *Latest Developments, Trends, and Prospects, Current Medicinal Chemistry—Anti-Cancer Agents* 529-560.

Paris et al. (2008) "Histone Deacetylase Inhibitors: From Bench to Clinic" *Journal of Medicinal Chemistry* A-Y.

Park et al. (2007) "A Simple and Efficient Docking Method to the Cyclin-Dependent Kinase 2" *Bull. Korean Chemistry Soc.* 28(2):211-219.

Price et al. (2007) Histone Deacetylase Inhibitors: An Analysis of REcent Patenting Activity *Informa UK Ltd, Expert Opinion, Ther. Patents* 745-765.

Rosato et al. (2003) "The Histone Deacetylase Inhibitor MS-275 Promotes Differentiation or Apoptosis in Human Leukemia Cells Through a Process Regulated by Generation of Reactive Oxygen Species and Induction of p21" *Cancer Research* 63:3637-3645.

Vadivelan et al. (2007) "Virtual Screening Studies to Design Patent CDKS2-Cyclin A Inhibitors" *Journal of Chemistry Inf. Model* 47(4):205-218.

Vigushin et al. (2004) "Targeted Histone Deacetylase Inhibition for Cancer Therapy" *Current Cancer Drug Targets* 4(2):205-218.

International Search Report for PCT/US2010/037647, International Filing Date Jun. 7, 2010, mailed Nov. 9, 2010.

U.S. Office Action for U.S. Appl. No. 12/747,159, mailed Dec. 10, 2010.

Fischer, B. et al. (2007) "Targeting Receptor Tyrosine Kinase Signalling in Small Cell Lung Cancer (SCLC): What Have We Learned So Far?", *Cancer Treatment Reviews*, vol. 33, pp. 391-406.

Arbiser, J.L. (2007) "Why Targeted Therapy Hasn't Worked in Advanced Cancer", *The Journal of Clinical Investigation*, vol. 17, No. 10 pp. 2762-2765.

Madhusudan, S. et al. (2004) "Tyrosine Kinase Inhibitors in Cancer Therapy", *Clinincal Biochemistry*, vol. 37, 00.618-635.

Lee, M. et al. (2003) "Molecular Targets for Cell Cycle Inhibition and Cancer Therapy", *Expert opinion on Therapeutic Patents*. 13(3):329-346.

CYCLOALKYLCARBAMATE BENZAMIDE ANILINE HDAC INHIBITOR COMPOUNDS

CROSS-REFERENCE TO RELATED APPLICATIONS

This application is filed under 35. U.S.C. 111(a) claiming the benefit under 35 U.S.C. 119(e) of U.S. Provisional Patent Application No. 61/185,134 filed Jun. 8, 2009, which is herein incorporated by reference in its entirety for all purposes.

FIELD

The present invention generally relates to compounds having enzyme inhibitory activity, pharmaceutical compositions comprising the compound, and methods useful for treating diseases.

BACKGROUND

Histones are protein components making up chromatin in association with DNA. Histones are subject to covalent modifications of various enzymes such as, for example, histone deacetylase (HDAC), histone methyltransferase (HMT) and histone acetyltransferase (HAT). Covalent modifications of core histones influence protein-protein interaction and protein access to DNA.

HDACs catalyze deacetylation of lysine residues on histones and other proteins. It is known that low levels of histone-acetylation are associated with repression of gene expression. Therefore, abnormal HDAC activities could destroy the delicate balance in cell regulation. The HDACs belong to four structurally and functionally different phylogenetic classes: class I (HDAC-1, -2, -3, and -8) compounds are closely related to yeast RPD3; class IIa (HDAC-4, -5, -7, and -9) and class IIb (HDAC-6 and -10) share domains with yeast HDAC-1; class IV, recently described (comprising HDAC-11), exhibits properties of both class I and class II HDACs. All the above HDACs are zinc dependent proteases. Class III HDACs have been identified on the basis of sequence similarity with Sir2, a yeast transcription repressor, and require the cofactor NAD⁺ for their deacetylase function. See, for example, Marielle Paris et al., *Histone Deacetylase Inhibitors: From Bench to Clinic*, JOURNAL OF MEDICINAL CHEMISTRY 51(11): 3330-3330 (2008).

It has been reported that HDAC activities play an important role in a variety of human disease states. Accordingly, an HDAC inhibitor can provide therapeutic benefits to a broad range of patients. Due to the therapeutic significance, various types of HDAC inhibitors have been developed to date. See, for example, Moradei et al., *Histone Deacetylase Inhibitors: Latest Developments, Trends, and Prospects*, CURR. MED. CHEM.: ANTI-CANCER AGENTS 5(5):529-560 (2005).

WO 2009/002534 mentions imidazopyridinyl compounds linked to anilide or hydroxamate moiety via thiazolylamino linker. The compounds are described as having enzyme inhibitory activity such as histone deacetylase inhibitory activity.

There is a continued need to develop new inhibitors to provide appropriate therapy for a variety of disease conditions implicated in HDAC activity.

SUMMARY

In various embodiments, a compound having HDAC inhibitory activity, a composition comprising the compound, and a method useful to treat diseases arising from abnormal cell proliferation or differentiation are provided.

In an embodiment, there is provided a compound of Formula (I) or a pharmaceutically acceptable salt thereof:

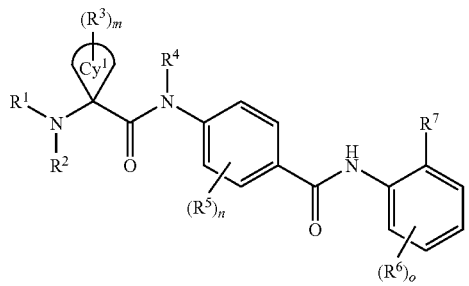

Formula (I)

$Cy^1$ is cycloalkylidene or heterocycloalkylidene;

$R^1$ and $R^2$ are independently selected from the group consisting of:

(a) H, alkyl, alkenyl, alkynyl, cycloalkyl, cycloalkylalkyl, heterocyclyl, heterocyclylalkyl, aryl, and arylalkyl; and (b) $R^8$—C(O)—$X^1$—, $R^8$—O—C(O)—$X^1$— and $R^8$—S(O)$_a$—$X^1$—, wherein $X^1$ is selected from the group consisting of a bond, —CH$_2$—, —NH—C$_{1-6}$ alkylene, —O—C$_{1-6}$ alkylene, C$_{1-6}$ alkylene, C$_{2-6}$ akenylene, C$_{2-6}$ alkynylene, C$_{3-6}$ cycloalkylene, arylene, and heterocyclylene;

$R^8$ is selected from the group consisting of H, hydroxy, amino, alkyl, N-alkylamino, N,N-dialkylamino, cycloalkyl, and heterocyclyl; and a is 0, 1 or 2, wherein each $R^1$ and $R^2$ is optionally substituted with one or more A where such an optional substitution is chemically feasible;

$R^3$ is independently selected from the group consisting of:

(a) cyano, oxo, halo, nitro, hydroxy, amino, mercapto, alkyl, aryl, cycloalkyl, heterocyclyl, and heterocyclylalkyl; and (b) $R^9$—C(O)—$X^2$—, $R^9$—O—C(O)—$X^2$— and $R^9$—S(O)$_a$—$X^2$—, wherein $X^2$ is selected from the group consisting of a bond, —NH—C$_{1-6}$ alkylene, —O—C$_{1-6}$ alkylene, C$_{1-6}$ alkylene, C$_{2-6}$ akenylene, C$_{2-6}$ alkynylene, C$_{3-6}$ cycloalkylene, arylene, and heterocyclylene;

$R^9$ is selected from the group consisting of H, amino, hydroxy, alkyl, alkoxy, alkylamino, N,N-dialkylamino, cycloalkyl, heterocyclyl, heterocyclylalkyl, and aryl; and a is 0, 1 or 2, wherein $R^1$ is optionally substituted with one or more B where such an optional substitution is chemically feasible; or when m is 2, the two $R^1$ groups can be substituted on the same carbon ring atom of Cy and together with the carbon ring atom of Cy form a ring situated on Cy in a spiro configuration, wherein the spiro ring is cycloalkyl or heterocycloalkyl;

m is an integer from 0 to the maximum number of substitutable positions on $Cy^1$;

$R^4$ is selected from the group consisting of —H, alkyl, cycloalkyl, heterocycloalkyl, aryl, heteroaryl, cycloalkylalkyl, heterocycloalkylalkyl, aralkyl, heteroaralkyl, alkylamino, alkylaminoalkyl, cycloalkylamino, heterocycloalkylamino, and arylamino, wherein $R^4$ is optionally substituted with one or more selected from halo, oxo, hydroxy, amino, alkylamino, carbamoyloxy, carbamoyl, cycloalkyl, cycloalkenyl, heterocyclyl and aryl where such an optional substitution is chemically feasible;

$R^5$ is independently selected from the group consisting of halo, hydroxy, nitro, cyano, haloalkyl, haloalkoxy, amino, carboxy, carbamoyl, sulphamoyl, $C_{1-10}$ alkyl, $C_{2-10}$ alkenyl, $C_{2-10}$ alkynyl, $C_{1-10}$ alkoxy, $C_{1-10}$ alkanoyl, N—$(C_{1-10}$ alkyl) amino, N,N—$(C_{1-10}$ alkyl)$_2$ amino, $C_{1-10}$ alkanoylamino, N—$(C_{1-10}$ alkyl)carbamoyl, N,N—$(C_{1-10}$ alkyl)$_2$ carbamoyl, $C_{1-10}$ alkyl-S(O)$_a$ wherein a is 0, 1 or 2, NH$_2$—S(O)$_2$NH—, N—$(C_{1-10}$ alkyl)sulphamoyl, N,N—$(C_{1-10}$ alkyl)$_2$sulphamoyl, cycloalkyl, heterocyclyl and aryl;

n is 0, 1, 2, 3 or 4;

$R^6$ is independently selected from the group consisting of —H, halo, haloalkyl, aryl and heteroaryl wherein the aryl or heteroaryl is optionally substituted with one or more substituents selected from the group consisting of amino, halo, alkyl, haloalkyl, cycloalkyl, heterocycloalkyl, aryl and heteroaryl;

o is 0, 1, 2, 3, or 4;

$R^7$ is NH$_2$— or OH—;

A is independently selected from the group consisting of oxo, halo, amino, hydroxyl, cyano, carbamoyl, $C_{1-10}$ alkyl, $C_{1-10}$ alkoxy, $C_{1-10}$ haloalkyl, $C_{1-10}$ alkanoylamino, N—$(C_{1-10}$ alkyl)amino, N,N—$(C_{1-10}$ dialkyl)amino, $C_{1-10}$ alkanoyl, N—$(C_{1-10}$ alkyl)carbamoyl, N,N—$(C_{1-10}$ dialkyl)carbamoyl, $C_{3-10}$ cycloalkyl, $(C_{3-10}$ cycloalkyl)$C_{1-10}$ alkyl, $C_{3-10}$ cycloalkoxy, $C_{1-10}$ haloalkoxy, heterocycloalkyl, (heterocycloalkyl)$C_{1-10}$ alkyl, aryl, (aryl)$C_{1-10}$ alkyl, heteroaryl, (heteroaryl)$C_{1-10}$ alkyl and R(R')(R")silyl wherein R, R' and R" are independently alkyl or aryl, or when $R^1$ or $R^2$ is a saturated or unsaturated cyclic group, two A groups can be substituted at adjacent positions of $R^1$ or $R^2$ and form a 5- or 6-membered, saturated or unsaturated cyclic moiety to make a fused ring with $R^1$ or $R^2$, wherein the cyclic moiety can contain one or more heteroatoms selected from N, O and S; and B is independently selected from the group consisting of halo, amino, carboxy, carbamoyl, $C_{1-10}$ alkyl, $C_{1-10}$ alkoxy, N—$(C_{1-10}$ alkyl)amino, N,N—$(C_{1-10}$ dialkyl)amino, N—$(C_{1-10}$ alkyl)carbamoyl, N,N—$(C_{1-10}$ dialkyl)carbamoyl, $C_{1-10}$ haloalkyl, $C_{3-10}$ cycloalkyl, $C_{3-10}$ heterocycloalkyl, $C_{3-10}$ aryl, heteroaryl, $(C_{1-10}$ alkyl)$C_{3-10}$ cycloalkyl and R(R')(R")silyl wherein R, R' and R" are independently alkyl or aryl.

In another embodiment, there is provided a compound of Formula (II) or a pharmaceutically acceptable salt thereof:

Formula (II)

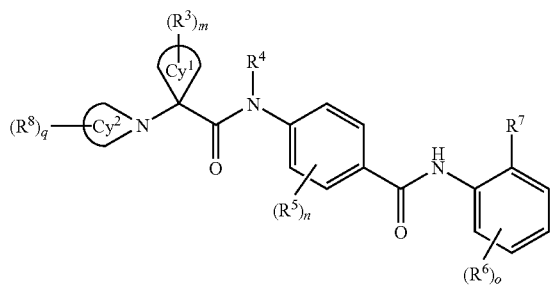

wherein

Cy$^2$ is heterocyclyl containing at least one nitrogen ring atom wherein Cy$^2$ is optionally substituted with one or more $R^8$ where chemically feasible;

q is an integer from 0 to the maximum number of substitutable positions on Cy$^2$;

$R^8$ is independently selected from the group consisting of:
(a) cyano, oxo, halo, nitro, hydroxy, amino, mercapto, alkyl, aryl, cycloalkyl, heterocyclyl, and heterocyclylalkyl;
(b) $R^{10}$—C(O)—X$^3$—, $R^{10}$—O—C(O)—X$^3$— and $R^{10}$—S(O)$_3$—X$^3$—, wherein X$^3$ is selected from the group consisting of a bond, —NH—$C_{1-6}$ alkylene, —O—$C_{1-6}$ alkylene, $C_{1-6}$ alkylene, $C_{2-6}$ akenylene, $C_{2-6}$ alkynylene, $C_{3-6}$ cycloalkylene, arylene, and heterocyclylene; and $R^{10}$ is selected from the group consisting of H, amino, hydroxy, alkyl, haloalkoxy, alkylamino, N,N-di alkylamino, cycloalkyl, heterocyclyl, heterocyclylalkyl, and aryl; and a is 0, 1 or 2, wherein $R^8$ is optionally substituted with one or more D where such an optional substitution is chemically feasible; or when m is 2, the two $R^8$ groups can be substituted on the same carbon ring atom of Cy and together with the carbon ring atom of Cy form a ring situated on Cy in a spiro configuration, wherein the spiro ring is cycloalkyl or heterocycloalkyl;

D is independently selected from the group consisting of halo, amino, carboxy, carbamoyl, alkyl, $C_{1-10}$ alkoxy, N—$(C_{1-10}$ alkyl)amino, N,N—$(C_{1-10}$ dialkyl)amino, N—$(C_{1-10}$ alkyl)carbamoyl, N,N—$(C_{1-10}$ dialkyl)carbamoyl, $C_{1-10}$ haloalkyl, $C_{3-10}$ cycloalkyl, $C_{3-10}$ heterocycloalkyl, $C_{3-10}$ aryl, heteroaryl, $(C_{1-10}$ alkyl)$C_{3-10}$ cycloalkyl and R(R')(R")silyl wherein R, R' and R" are independently alkyl or aryl; and m, n, o, Cy$^1$, $R^3$, $R^4$, $R^5$, $R^6$ and $R^7$ are as defined above.

In yet another embodiment, there is provided a pharmaceutical composition comprise an HDAC-inhibitory effective amount of one or more compounds described herein and a pharmaceutically-acceptable carrier.

In yet another embodiment, there is provided a method of inhibiting or treating diseases arising from abnormal cell proliferation and differentiation comprise administering to a subject a therapeutically effective amount of one or more compounds described herein. Other methods involve co-therapies by administering one or more of the compounds together with other anti-cancer agents.

The compounds above are more fully described in the detailed description that follows.

DETAILED DESCRIPTION

The following description is merely exemplary in nature and is not intended to limit the present disclosure, application, or uses.

Definitions

"Alkenyl" refers to a straight or branched hydrocarbyl group with at least one site of unsaturation, i.e. a carbon-carbon, sp$^2$ double bond. In an embodiment, alkenyl has from 2 to 12 carbon atoms. In some embodiments, alkenyl is a $C_2$-$C_{10}$ alkenyl group or a $C_2$-$C_6$ alkenyl group. Examples of alkenyl group include, but are not limited to, ethylene or vinyl (—CH═CH$_2$), allyl (—CH$_2$CH═CH$_2$), cyclopentenyl (—C$_5$H$_7$), and 5-hexenyl (—CH$_2$CH$_2$CH$_2$CH$_2$CH═CH$_2$).

"Alkanoyl" is the group RC(O)—; "alkanoyloxy" is RC(O) O—; and "alkanoylamino" is RC(O)NR'—; where R is an alkyl group as defined herein, and R' is hydrogen or alkyl. In various embodiments, R is a $C_1$-$C_{10}$ alkyl group or a $C_1$-$C_6$ alkyl group.

"Alkanoylalkyl" is the group RC(O)R'—, wherein R and R' are independently selected alkyl.

"Alkanoyloxyalkyl" is the group RC(O)OR'—, wherein R and R' are independently selected alkyl.

"Alkoxy" is RO— where R is alkyl. Non-limiting examples of alkoxy groups include methoxy, ethoxy and propoxy.

"Alkoxyalkyl" refers to an alkyl moiety substituted with an alkoxy group. Examples of alkoxyalkyl groups include methoxymethyl, methoxyethyl, methoxypropyl and ethoxyethyl.

"Alkoxycarbonyl" is ROC(O)—, where R is an alkyl group as defined herein. In various embodiments, R is a $C_1$-$C_{10}$ alkyl group or a $C_1$-$C_6$ alkyl group.

"Alkoxycarbonylalkyl" is the group ROC(O)R'—, wherein R and R' are independently selected alkyl.

"Alkyl" refers to a straight or branched chain hydrocarbyl group. In an embodiment, alkyl has from 1 to 12 carbon atoms. In some embodiments, alkyl is a $C_1$-$C_{10}$ alkyl group or a $C_1$-$C_6$ alkyl group. Examples of alkyl groups include, but are not limited to, methyl, ethyl, propyl, isopropyl, butyl, isobutyl, t-butyl, pentyl, hexyl, heptyl, octyl, nonyl and decyl.

"Alkylamino" refers to an amino group substituted with one or more alkyl groups. "N-(alkyl)amino" is RHN— and "N,N-(alkyl)$_2$amino" is $R_2$N—, where the R groups are alkyl as defined herein and are the same or different. In various embodiments, R is a $C_1$-$C_{10}$ alkyl group or a $C_1$-$C_6$ alkyl group. Examples of alkylamino groups include methylamino, ethylamino, propylamino, butylamino, N,N-dimethylamino, N,N-diethylamino, and methylethylamino.

"Alkylaminoalkyl" refers to an alkyl moiety substituted with an alkylamino group, wherein alkylamino is as defined herein. Examples of alkylaminoakyl groups include methylaminomethyl and ethylaminomethyl.

"Alkylcycloalkyl" is an alkyl group, as defined herein, substituted with a cycloalkyl group, also as defined herein.

"N-(alkyl)carbamoyl" is the group R—NH—C(O), wherein R is alkyl as defined herein. In various embodiments, R is a $C_1$-$C_{10}$ alkyl group or a $C_1$-$C_6$ alkyl. Examples of alkylcarbamoylalkyl groups include, but are not limited to, N-methylcarbamoyl, N-ethylcarbamoyl, N-propylcarbamoyl and N-butylcarbamoyl. "N,N-(Alkyl)$_2$-carbamoyl" and "N,N-dialkylcarbamoyl" is the group (R)R'N—C(O)—, wherein R and R' are independently selected alkyl as defined herein. In various embodiments, R and R' are $C_1$-$C_{10}$ alkyl groups or $C_1$-$C_6$ alkyl groups. Examples of N,N-dialkylcarbamoyl groups include, but are not limited to, N,N-dimethylcarbamoyl, N,N-methylethylcarbamoyl, N,N-diethylcarbamoyl, N,N-dipropylcarbamoyl and N,N-dibutylcarbamoyl, "Alkylcarbamoylalkyl" is the group R—NH—C(O)—R', wherein R and R' are independently selected alkyl as defined herein. In various embodiments, R and R' are $C_1$-$C_{10}$ alkyl groups or $C_1$-$C_6$ alkyl groups. Examples of alkylcarbamoylalkyl groups include, but are not limited to, N-methylcarbamoylmethyl, N-methylcarbamoylethyl, N-ethylcarbamoylmethyl, N-ethylcarbamoylethyl, N-propylcarbamoylethyl and N-butylcarbamoylethyl.

"Alkylsulfinyl" is the group RS(O)—, wherein R is alkyl as defined herein. In various embodiments, R is $C_1$-$C_{10}$ alkyl group or $C_1$-$C_6$ alkyl group. Examples of alkylsulfinyl groups include, but are not limited to, methylsulfinyl, ethylsulfinyl, propylsulfinyl and butylsulfinyl.

"Alkylsulfonyl" is the group RS(O)$_2$—, wherein R is alkyl as defined herein. In various embodiments, R is $C_1$-$C_{10}$ alkyl group or a $C_1$-$C_6$ alkyl group. Examples of alkylsulfonyl groups include, but are not limited to, methylsulfonyl, ethylsulfonyl, propylsulfonyl and butylsulfonyl.

"Alkylthio" is the group RS—, wherein R is alkyl as defined herein. In various embodiments, R is $C_1$-$C_{10}$ alkyl group or a $C_1$-$C_6$ alkyl group. Examples of alkylthio groups include, but are not limited to, methylthio, ethylthio, propylthio and butylthio.

"Alkynyl" refers to a straight or branched carbon-chain group with at least one site of unsaturation, i.e. a carbon-carbon, sp triple bond. In an embodiment, alkynyl has from 2 to 12 carbon atoms. In some embodiments, alkynyl is a $C_2$-$C_{10}$ alkynyl group or a $C_2$-$C_6$ alkynyl group. Examples of alkynyl groups include acetylenic (—C≡CH) and propargyl (—$CH_2$C≡CH).

"Aminoalkyl" is the group $H_2$NR—, wherein R is alkyl as defined herein. Examples of aminoalkyl groups include, but are not limited to, aminomethyl, 1-aminoethyl, 2-aminoethyl, 1-aminopropyl, 2-aminopropyl and 3-aminopropyl.

"Aminosulfonylalkyl" is the group $H_2$NS(O)$_2$R—, wherein R is alkyl as defined herein. Examples of aminosulfonylalkyl groups include, but are not limited to aminosulfonylmethyl, aminosulfonylethyl, aminosulfonylpropyl and aminosulfonylbutyl.

"Aryl" refers to any monocyclic or bicyclic carbon ring of up to 7 atoms in each ring, wherein at least one ring is aromatic. Aryl encompasses a ring system of up to 14 carbons atoms that includes a carbocyclic aromatic group fused with a 5- or 6-membered cycloalkyl group. Examples of aryl groups include, but are not limited to, phenyl, naphthyl, tetrahydronaphthyl and indanyl.

"Arylalkyl" and "Aralkyl" refer to any alkyl group, as defined herein, substituted with any aryl group, also as defined herein. Examples of aralkyl groups include, but are not limited to, benzyl, phenylethyl, naphthylmethyl, tetrahydronaphtylmethyl and indanylmethyl.

"Arylamino" is the group RHN—, wherein R is aryl as defined herein. Examples of arylamino groups include, but are not limited to, phenylamine, naphthylamine, tetrahydronaphthylamino and indanylamino.

"Aryloxy" is RO—, where R is aryl. "Arylthio" is RS—, where R is aryl.

"Arylsulfonyl" is the group RS(O)$_2$—, wherein R is aryl as defined herein. Examples of arylsulfonyl groups include, but are not limited to, phenylsulfonyl, naphthylsulfonyl, tetrahydronaphthylsulfonyl and indanyl sulfonyl.

"Arylthio" is the group RS—, wherein R is aryl as defined herein. Examples of arylthio groups include, but are not limited to, phenylthio, naphthylthio, tetrahydronaphthylthio and indanylthio.

"Arylthioalkyl" refers to any alkyl group, as defined herein, substituted with any arylthio group, as also defined herein. Examples of arylthioalkyl groups include, but are not limited to, phenylthiomethyl, naphthylthiomethyl, tetrahydronaphthylthiomethyl, indanylthiomethyl, phenylthioethyl, naphthylthioethyl, tetrahydronaphthylthioethyl and indanylthioethyl.

"Carbonyl" is the group —C(O)—, which can also be written as —(C═O)—. The carbonyl group can be found in several chemical moieties, such as acids, aldehydes, amides, cabamates, carboxylates, esters, and ketone; and functional groups, such as carbamoyl, alkanoyl, cycloalkanoyl, and heterocycloalkanoyl.

"Carbamoyloxy" refers to the group $H_2$NC(O)O—.

"Carbamoyl" is the group $NH_2$—C(O)—; the nitrogen can be substituted with alkyl groups. N-(alkyl)carbamoyl is RNH—C(O)— and N,N-(alkyl)$_2$ carbamoyl is $R_2$N—C(O)—, where the R groups are alkyl as defined herein and are the same or different. In various embodiments, R is a $C_1$-$C_{10}$ alkyl group or a $C_1$-$C_6$ alkyl group.

"Carbamoylalkyl" refer to the group $NH_2$C(O)R—, wherein R is alkyl as defined herein. Examples of carbamoylalkyl groups include, but are not limited to, carbamoylmethyl, carbamoylethyl, carbamoylpropyl and carbamoylbutyl.

"Carboxy" is the group HOC(O)—, and can also be referred to as a carboxylic acid.

"Cycloalkanoyl" is the group RC(O)—, wherein R is cycloalkyl as defined herein. Examples include, but are not limited to, cyclopropanoyl, cyclobutanoyl, cyclopentanoyl and cyclohexanoyl.

"Cycloalkylalkanoyl" is the group RC(O)—, wherein R is cycloalkyl as defined herein. Examples include, but are not limited to, cyclopropanoyl, cyclobutanoyl, cyclopentanoyl and cyclohexanoyl.

"Cycloalkylaminosulfonyl" is the group R—NH—S(O)$_2$—, wherein R is cycloalkyl as defined herein. Examples of cylcoalkylaminosulfonyl groups include, but are not limited to, cyclopropylaminosulfonyl, cyclobutylaminosulfonyl, cyclopentylaminosulfonyl and cyclohexylaminosulfonyl.

"Cycloalkylaminosulfinyl" is the group R—NH—S(O)—, wherein R is cycloalkyl as defined herein. Examples of cylcoalkylaminosulfinyl groups include, but are not limited to, cyclopropylaminosulfinyl, cyclobutylaminosulfinyl, cyclopentylaminosulfinyl and cyclohexylaminosulfinyl.

"Cycloalkylcarbonyl" and "cycloalkanoyl" refer to the group RC(O)—, wherein are is cycloalkyl as defined herein. Examples of cycloalkylcarbonyl groups include, but are not limited to, cyclopropylcarbonyl, cyclobutylcarbonyl, cyclopentylcarbonyl and cyclohexylcarbonyl.

"Cycloalkyl" is a saturated or partially unsaturated, mono-, bi- or tri-cyclic hydrocarbon group. In various embodiments, it refers to a saturated or a partially unsaturated $C_3$-$C_{12}$ cyclic moiety, examples of which include cyclopropyl, cyclobutyl, cyclopentyl, cyclopentenyl, cyclohexyl, cyclohexenyl, cycloheptyl and cyclooctyl.

In various embodiment, the term, cycloalkyl, is a bridged cycloalkyl group and examples of which include:

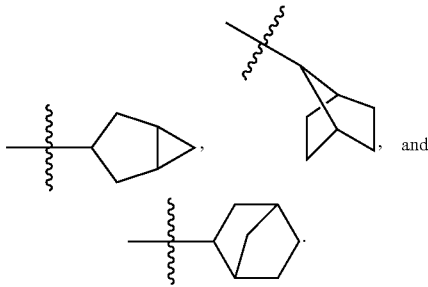

"Cycloalkylamino" is the group R—NH—, wherein R is cycloalkyl as defined herein. Examples include, but are not limited to, cyclopropylamino, cyclobutylamino, cyclopentylamino and cyclohexylamino.

"Cycloalkyloxy" is RO—, where R is cycloalkyl.

"Cycloalkyloxysulfonyl" and "cycloalkoxysulfonyl" refer to the group ROS(O)$_2$—, wherein R is cycloalkyl as defined herein. Examples of cycloalkyloxysulfonyl groups include, but are not limited to, cyclopropyloxysulfonyl, cyclobutyloxysulfonyl, cyclopentyloxysulfonyl and cyclohexyloxysulfonyl.

"Cycloalkyloxysulfinyl" and "cylcoalkoxysulfinyl" refer to the group ROS(O)—, wherein R is cycloalkyl as defined herein. Examples of cycloalkyloxysulfinyl groups include, but are not limited to, cyclopropyloxysulfinyl, cyclobutyloxysulfinyl, cyclopentyloxysulfinyl and cyclohexyloxysuilinyl.

"Cycloalkylalkyl" refers to an alkyl moiety substituted with a cycloalkyl group, wherein cycloalkyl is as defined herein. Examples of cycloalkylalkyl groups include, but are not limited to, cyclopropylmethyl, cyclobutylmethyl, cyclopentylethyl and cyclohexylmethyl.

"Cycloalkylalkyl-S(O)$_2$—" and "cycloalkylalkylsulfonyl" refer to the group R—R'—S(O)$_2$, wherein R is a cycloalkyl as defined herein, and R' is an alkyl as also defined herein. Examples of cycloalkylalkyl-S(O)$_2$— include, but are not limited to, cyclopropylmethyl-S(O)$_2$—, cyclobutylmethyl-S(O)$_2$—, cyclopentylmethyl-S(O)$_2$—, cyclopenylethyl-S(O)$_2$— and cyclohexylmethyl-S(O)$_2$—.

"Cycloalkylsulfonyl" is the group RS(O)$_2$—, wherein the R is cycloalkyl as defined herein. Examples of cycloalkylsulfonyl groups include, but are not limited to, cyclopropylsulfonyl, cyclobutylsulfonyl, cyclopentylsulfonyl and cyclohexylsulfonyl.

"Cycloalkylidene" refers to a divalent group formed from cycloalkane having two substituents on a single carbon of the cycloalkane. It can be represented in illustrative fashion by the following formula,

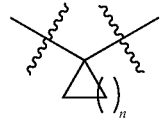

wherein n determines the size of the ring and is one or greater. For example, n=2 makes cyclobutylidene. In various embodiments, cycloalkylidene is a divalent $C_3$-$C_{12}$ cyclic moiety. Examples of cycloalkylidene groups include cyclopropylidene, cyclobutylidene, cyclopentylidene and cyclohexylidene.

"Dialkylamino" refers to an RR'N— group where R and R' are independently selected alkyl as defined herein. Examples of dialkylamino groups include, but are not limited to, N,N-dimethylamino, N,N-diethylamino, methylethylamino and methylpropylamino. In various embodiments, R and R' are independently a $C_1$-$C_{10}$ alkyl group or a $C_1$-$C_6$ alkyl group.

"Dialkylaminoalkyl" refers to an alkyl moiety substituted with a dialkylamino group, wherein dialkylamino is as defined herein. Examples of dialkylaminoalkyl groups include, but are not limited to, N,N-dimethylaminomethyl and N,N-diethylaminomethyl.

"Dialkylcarbamoyl" is the group RR'N—C(O)—, wherein R and R' are independently selected alkyl as defined herein. In various embodiments, R and R' are $C_1$-$C_{10}$alkyl groups or $C_1$-$C_6$ alkyl groups. Examples of N,N-dialkylcarbamoyl groups include, but are not limited to, N,N-dimethylcarbamoyl, N,N-methylethylcarbamoyl, N,N-diethylcarbamoyl, N,N-dipropylcarbamoyl and N,N-dibutylcarbamoyl.

"Dialkylheterocycloalkyl-S(O)$_2$-" and "dialkylheterocycloalkylsulfonyl" refer to the group RS(O)$_2$—, wherein R is a heterocycloalkyl, as defined herein, substituted with two independently selected alkyl, as also defined herein.

The suffix "-ene" on a the name of a chemical moiety refers to any divalent, carbon-containing species, including, but not limited to, alkylene, alkenylene, alkynylene, cycloalkylene, heterocycloalkylene, arylene, heteroarylene, cyclylene, and heterocyclylene. The two attachments to the divalent moiety can occur on the same atom or on different atoms, when chemically feasible.

In various embodiments, examples of "Alkylene" include, but are not limited to, methylene, ethylene, propylene, isopropylene, butylene, isobutylene, sec-butylene, and tert-butylene. For alkylenes greater than one carbon in length, attachment can occur on the same carbon or on different carbons. For example, butylene can be attached as follows:

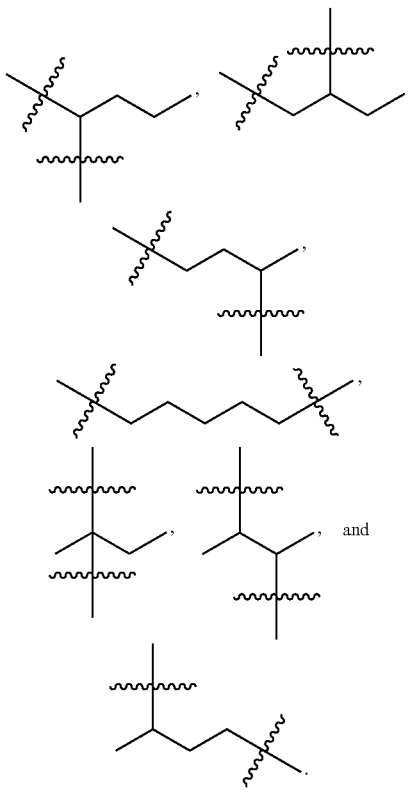

In various embodiments, "Arylene" refers to a divalent aryl substituent, as defined herein. The attachments can be in an ortho, meta, or para configuration.

"Feasible" refers to a structure or process which is capable of being accomplished, possible, suitable, or logical. When a structure or process is "chemically feasible", that structure or process is synthetically attainable, chemically stable to the typical ambient conditions and/or contributes to favorable biological properties such as efficacy, bioavailability and minimal toxicity for the intended use. Chemically feasible structures are bound by the rules of electron bonding, whereby bonds can only be formed between atoms that are capable of forming bonds with one another. Likewise, chemically feasible processes can only produce structures which are themselves chemically feasible. Explosive, touch-sensitive, and pyrophoric substance or substances which undergo exothermic unimolar decompositions at high rates are typically not considered chemically feasible.

"Halo" refers to chloro (—Cl), bromo (—Br), fluoro (—F) or iodo (—I).

"Haloalkoxy" refers to an alkoxy group substituted with one or more halo groups and examples of haloalkoxy groups include, but are not limited to, —OCF$_3$, —OCHF$_2$ and —OCH$_2$F.

"Haloalkoxyalkyl" refers to an alkyl moiety substituted with a haloalkoxy group, wherein haloalkoxy is as defined herein. Examples of haloalkoxyalkyl groups include trifluoromethoxymethyl, trifluoroethoxymethyl and trifluoromethoxyethyl.

"Haloalkyl" refers to an alkyl moiety substituted with one or more halo groups. Examples of haloalkyl groups include —CF$_3$ and —CHF$_2$.

"Haloaryl" refers to any aryl group which is substituted with one or more independently selected halo group.

"Heteroaryl" is a heterocyclyl where at least one ring is aromatic. In various embodiments, it refers to a monocyclic, bicyclic or tricyclic ring having up to 7 atoms in each ring, wherein at least one ring is aromatic and contains from 1 to 4 heteroatoms in the ring selected from the group consisting of N, O and S, Non-limiting examples of heteroaryl include pyridyl, thienyl, furanyl, pyrimidyl, imidazolyl, pyranyl, pyrazolyl, thiazolyl, thiadiazolyl, isothiazolyl, oxazolyl, isoxazoyl, pyrrolyl, pyridazinyl, pyrazinyl, quinolinyl, isoquinolinyl, benzofuranyl, dibenzofuranyl, dibenzothiophenyl, benzothienyl, indolyl, benzothiazolyl, benzooxazolyl, benzimidazolyl, isoindolyl, benzotriazolyl, purinyl, thianaphthenyl and pyrazinyl. Attachment of heteroaryl can occur via an aromatic ring, or, if heteroaryl is bicyclic or tricyclic and one of the rings is not aromatic or contains no heteroatoms, through a non-aromatic ring or a ring containing no heteroatoms. "Heteroaryl" is also understood to include the N-oxide derivative of any nitrogen containing heteroaryl.

"Heteroarylalkyl" refers to an alkyl group, as defined herein, substituted with a heteroaryl group, also as defined herein. Examples of heteroarylalkyl groups include, but are not limited to, pyridylmethyl, pyridylethyl, thienylpropyl and furanylbutyl.

"Heteroaryloxy" is RO—, where R is heteroaryl.

"Heteroarylsulfonyl" is the group RS(O)$_2$—, wherein the R is heteroaryl as defined herein. Examples of heteroarylsulfonyl groups include, but are not limited to, pyridylsulfonyl, thienylsulfonyl, furanylsulfonyl, pyrimidylsulfonyl and imidazolylsulfonyl.

"Heterocycloalkyl" refers to a saturated, or partially unsaturated monocyclic, bicyclic or tricyclic group of 2 to 14 ring-carbon atoms containing one or more heteroatoms selected from P, N, O and S, in addition to ring-carbon atoms. In various embodiments the heterocyclic group is attached to another moiety through carbon or through a heteroatom, and is optionally substituted on carbon or a heteroatom. Examples of heterocycloalkyl include morpholinyl, thiomorpholinyl, and

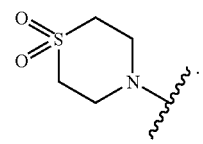

In various embodiment, the term, "heterocycloalkyl," is a bridged cycloalkyl group and examples of which include:

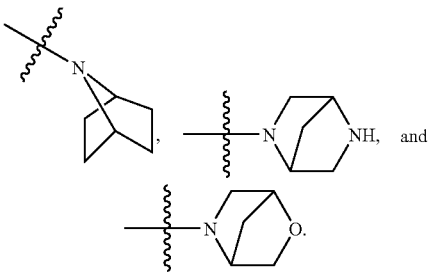

"Heterocycloalkylalkyl" refers to any alkyl group, as defined herein, substituted with any heterocycloalkyl group, as also defined herein.

"Heterocycloalkylamino" is the group RHN—, wherein R is a heterocycloalkyl, as defined herein. Examples of heterocycloalkylamino groups include, but are not limited to, azetidinylamino, benzoimidazolylamino, benzofuranylamino, benxopyrazolyl and benzotriazoylamino.

"Heterocycloalkyl-S(O)$_2$-" and "heterocycloalkylsulfonyl" refer to the group RS(O)$_2$, wherein R is heterocycloalkyl as defined herein.

"Heterocycloalkyl (C=O)" "heterocycloalkylcarbonyl" and "heterocycloalkanoyl" refer to the group RC(O)—, wherein R is heterocycloalkyl as defined herein.

"Heterocyclyl" includes the heteroaryls and the heterocycloclkyls defined herein and refers to a saturated or partially unsaturated monocyclic, bicyclic or tricyclic group of 2 to 14 ring-carbon atoms and, in addition to ring-carbon atoms, 1 to 4 heteroatoms selected from P, N, O and S. In various embodiments the heterocyclic group is attached to another moiety through carbon or through a heteroatom, and is optionally substituted on carbon or a heteroatom. Examples of heterocyclyl include azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

"Heterocyclylalkyl" is an alkyl group substituted with a heterocyclyl.

"Heterocycloalkyloxy" is RO—, where R is heterocycloalkyl.

"Heterocycloalkylthio" is RS—, where R is heterocycloalkyl.

"Heterocycloalkylidene" refers to a divalent group formed from a heterocyclyl with two substituents on a single ring carbon. It can be represented in illustrative fashion by the formula

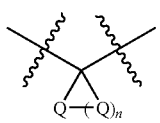

where n determines the size of the ring and is one or greater. Each Q is independently —CH$_2$— or a heteroatom selected from —NH—, —O— and —S—, and when Q is methylene (—CH$_2$—) or imino (—NH—), Q is optionally substituted with a group as defined herein.

"Hydroxyalkoxy" refers to an alkoxy group substituted with a hydroxy group (—OH), wherein alkoxy is as defined herein. An example of hydroxyalkoxy is hydroxyethoxy.

"Hydroxyalkyl" refers to a linear or branched monovalent $C_1$-$C_{10}$ hydrocarbon group substituted with at least one hydroxy group and examples of hydroxyalkyl groups include, but are not limited to, hydroxymethyl, hydroxyethyl, hydroxypropyl and hydroxybutyl.

"Mercapto" refers to the sulfhydryl group HS—.

"Sulphamoyl" is NH$_2$—S(O)$_2$—; "N-(alkyl)sulphamoyl" is R—NH—S(O)$_2$—; and "N,N-(alkyl)$_2$ sulphamoyl" is R$_2$N—S(O)$_2$—, where the R groups are alkyl as defined herein and are the same or different. In various embodiments, R is a $C_1$-$C_{10}$ alkyl group or a $C_1$-$C_6$ alkyl group.

"Trialkylsilyl" is the group R(R')(R")Si—, wherein R, R' and R" are each independently selected alkyl. Examples include, but are not limited to, trimethylsilyl, triethylsilyl, triisopropylsilyl, and t-butyldimethylsilyl.

"Pharmaceutically-acceptable" means suitable for use in pharmaceutical preparations, generally considered as safe for such use, officially approved by a regulatory agency of a national or state government for such use, or being listed in the U.S. Pharmacopoeia or other generally recognized pharmacopoeia for use in animals, and more particularly in humans.

"Pharmaceutically-acceptable carrier" refers to a diluent, adjuvant, excipient, or carrier, or other ingredient which is pharmaceutically-acceptable and with which a compound of the invention is administered.

"Pharmaceutically-acceptable salt" refers to a salt which may enhance desired pharmacological activity. Examples of pharmaceutically-acceptable salts include acid addition salts formed with inorganic or organic acids, metal salts and amine salts. Examples of acid addition salts formed with inorganic acids include salts with hydrochloric acid, hydrobromic acid, sulfuric acid, nitric acid and phosphoric acid. Examples of acid addition salts formed with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methyl-bicyclo[2.2.2]oct-2-en-1-carboxylic acid, glucoheptonic acid, 4,4'-methylen-bis(3-hydroxy-2-naphthoic) acid, 3-phenylpropionic acid, trimethylacetic acid, tert-butylacetic acid, lauryl sulfuric acid, gluconic acid, glutamic acid, hydroxynaphthoic acids, salicylic acid, stearic acid and muconic acid. Examples of metal salts include salts with sodium, potassium, calcium, magnesium, aluminum, iron, and zinc ions. Examples of amine salts include salts with ammonia and organic nitrogenous bases strong enough to form salts with carboxylic acids.

"Therapeutically-effective amount" refers to an amount of a compound that, when administered to a subject for treating a disease, is sufficient to effect treatment for the disease. "Therapeutically effective amount" can vary depending on the compound, the disease and its severity, the age, the weight, etc. of the subject to be treated.

Embraced herein, where applicable, are permissible isomers such as tautomers, racemates, enantiomers, diastereomers, atropisomers, configurational isomers of double bonds (E- and/or Z-), cis- and trans-configurations in ring substitution patterns, and isotopic variants.

In one embodiment, there is provided a compound selected from those of Formula (I) and pharmaceutically acceptable salts thereof:

Formula (I)

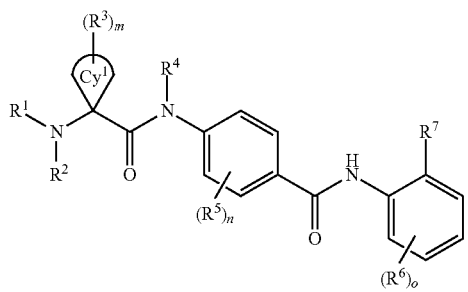

wherein $Cy^1$, $R^1$, $R^2$, $R^3$, $R^4$, $R^5$, $R^6$, m, n and o are as defined above.

In an embodiment, $Cy^1$ is $C_{3-7}$ cycloalkylidene, where $R^1R^2N$— and the amido containing group are substituted in a 1,1-configuration on the $C_{3-7}$ ring. The ring of cycloalkylidene is optionally substituted with one or more groups $R^3$ as further defined herein. In various embodiments, the ring is completely saturated with hydrogen so that the variable m in Formula I is zero. In particular embodiments, $Cy^1$ is cyclopropylidene, cyclobutylidene, cyclopentylidene, or hexylidene.

In an embodiment, $Cy^1$ is a heterocyclic ring with 1,1-disubstitution by $R^1R^2N$— and the amido containing group. Examples include 5- to 7-membered rings containing at least one heteroatom selected from N, O, and S. In particular embodiments, there is no heteroatom substitution in $Cy^1$ adjacent the 1,1-attachment of $R^1R^2N$— and the amido containing group. Carbon atoms in the 1,1-disubstituted heterocyclic ring are optionally substituted with oxo groups, and substitutable positions on the ring are optionally substituted with 1 or more groups $R^3$. In various embodiments, the only substituent $R^3$ is an oxo group on carbon. In other embodiments, all substitutable positions contain hydrogen, so that the variable n in Formula (I) is zero. A non-limiting example of $Cy^1$ is tetrahydropyran-4-yl, where Ar and $Cy^2$ are attached to the 4-position of tetrahydropyran, with the oxygen position taken as position 1.

In various embodiments, $R^1$ and $R^2$ are independently selected from the group consisting of H, alkyl, carboxy, haloalkyl, alkynyl, carbamoyl, alkanoyl, arylcarbonyl, cycloalkylcarbonyl, heteroarylcarbonyl, heterocycloalkylcarbonyl, alkylsulfonyl, arylsulfonyl, cycloalkylsulfonyl, heteroarylsulfonyl, heterocycloalkylsulfonyl, and sulfamoyl, wherein $R^1$ and $R^2$ are optionally substituted by one or more A where such an optional substitution is chemically feasible, wherein A is selected from chloro, hydroxy, oxo, methyl, ethyl, propyl, methoxy, ethoxy, methoxymethyl, ethoxyethyl, propoxyethyl, methoxyethoxy, trifluoromethyl, hydroxyethoxy, dimethylamino, diethylamino, dimethylaminomethyl, diethylaminomethyl, dimethylaminoethoxy, trifluoromethoxymethyl, trifluoroethoxymethyl, benzyl, phenylethyl, trifluoromethylphenylethyl, phenoxymethyl, fluorophenoxymethyl, phenyl ethylaminomethyl, benzylaminomethyl, triazinylmethyl, piperidinylmethyl, piperidinyloxy, trifluoromethylpiperidinylmethyl, pyridinyloxymethyl, pyridinylmethoxy, tetrahydropyrazinyloxy, methylpiperazinylmethyl, pyrrolidin-1-yl, pyrrolidin-2-yl, pyrrolidin-3-yl, pyrrolidin-1-ylmethyl, pyrrolidin-2-ylmethyl, pyrrolidin-3-ylmethyl, pyrrolidin-1-ylethoxy, pyrrolidin-2-ylethoxy, pyrrolidin-3-ylethoxy, imidazol-1-ylmethyl, imidazol-2-ylmethyl, imidazol-4-ylmethyl, imidazolidin-1-yl, imidazolidin-2-yl, imidazolidin-4-yl, imidazolidin-1-ylmethyl, imidazolidin-2-ylmethyl, imidazolidin 4 ylmethyl, imidazolin-1-yl, imidazolin-2-yl, pyrazolidin-1-yl, pyrazolidin-3-yl, pyrazolidin-4-yl, pyrazolin-1-yl, pyrazolin-3-yl, pyrazolin-4-yl, piperidin-1-yl, piperidin-2-yl, piperidin-3-yl, piperidin-4-yl, piperidin-1-ylmethyl, piperidin-2-ylmethyl, piperidin-3-ylmethyl, piperidin-4-ylmethyl, piperazin-1-yl, piperazin-2-yl, piperazin-3-yl, morpholin-2-yl, morpholin-3-yl, morpholin-4-yl, morpholin-2-ylmethyl, morpholin-3-ylmethyl, morpholin-4-ylmethyl, morpholin-2-ylethoxy, morpholin-3-ylethoxy and morpholin-4-ylethoxy, or when $R^1$ or $R^2$ is a saturated or unsaturated cyclic group, two A groups can be substituted at adjacent positions of $R^1$ or $R^2$ and form a 5- or 6-membered, saturated or unsaturated cyclic moiety to make a fused ring with $R^1$ or $R^2$, wherein the cyclic moiety can contain one or more heteroatoms selected from N, O and S;

In various embodiments, $R^4$ is selected from methyl, cyclopropyl, cyclopropylmethyl, trifluoroethyl, dimethylaminoethyl, pyrrolidinylethyl, benzyl, pyridinylmethyl, ethylpyridinylmethyl, acetylpiperazinylethyl, methylsulfonamidoethyl, methoxyethyl, methoxycarbonylaminoethyl, pyrazinylaminoethyl, chlorofluorobenzyl, trifluoromethylpyridinylmethyl, imidazolylethyl, imidazolylmethyl, methyldioxopiperidinylmethyl, dioxopyrrolidinylethyl, dimethylcarbamoylmethyl, morpholinocarbonylethyl, hydroxymethylpropyl, fluorophenyl, and tetrahydropyranyl.

In various embodiments, $R^6$ and $R^7$ are substitutions on the phenyl ring attached to the -phenyl-C(O)—NH— linker; and $R^6$ and $R^7$ are selected to make any of the following substitutions:

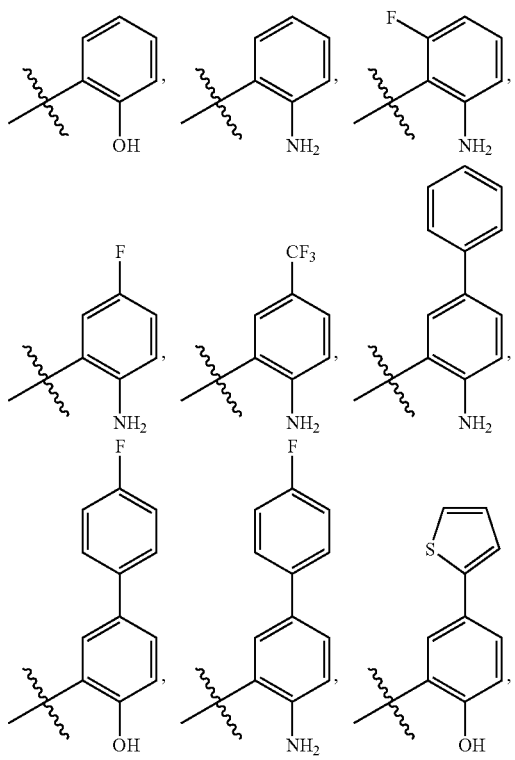

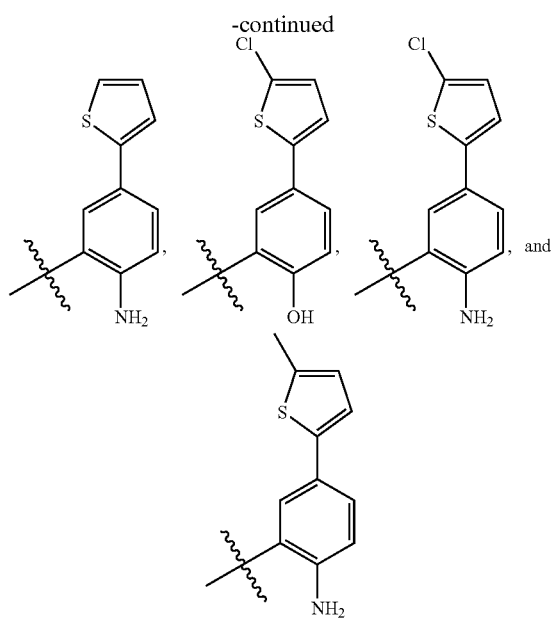

wherein the wavy line shows an attachment position to the -phenyl-C(O)—NH— linker %

In particular embodiments, compounds are selected from those of Formula (I-a) and Formula (I-b) with substituents defined as in Formula (I):

Formula (I-a)

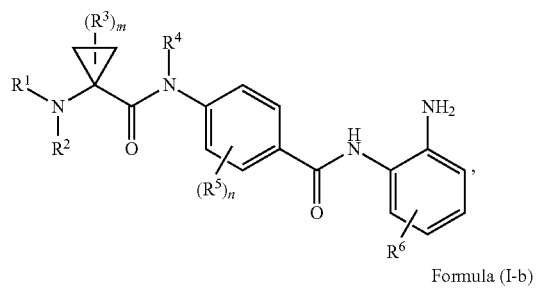

Formula (I-b)

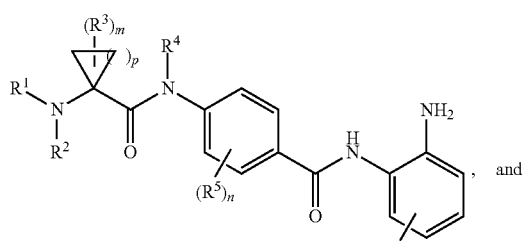
and

Formula (I-c)

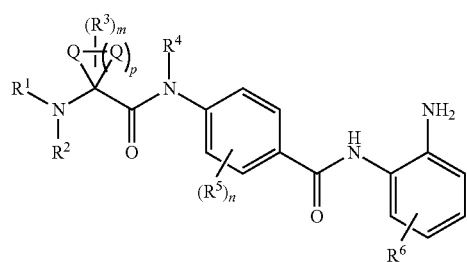

wherein m, n, p, $R^1$, $R^2$, $R^3$, $R^4$, $R^5$ and $R^6$ are as defined above; and each Q is a ring atom which is independently selected from C, N, O and S.

Compounds defined above are useful to inhibit HDACs. In one embodiment, therefore, a compound of the invention is used in inhibiting HDAC enzymes such as, for example, mammalian HDAC. More specifically, a compound of the invention can be used to treat or inhibit MAC-mediated diseases or abnormalities.

In an embodiment of the compounds of Formula (I), (I-a), (I-b) and (I-c), one or more (including all) of the substituents $R^1$, $R^2$, $R^3$, $R^4$, $R^5$ and $R^6$ are further limited as follows:

$R^1$ and $R^2$, which are optionally substituted with one or more A, are independently selected from the group consisting of H, methyl, butyl, tetrahydrofuranylmethyl, alkylazetidinyl, alkylpiperidinyl, alkylpyrrolidinyl, cyclopentyl, oxoimidazolidinylethyl, alkyloxopiperidinyl, trifluorophenylethyl, trifluoropyridinylethyl, alkylphenylcyclopropyl, hydroxy, trifluoromethylpentynyl, cyclopropylpropynyl, hydroxybutynyl, methylcyclopropoxycarbonyl, tert-butoxycarbonyl, trifluoromethylpropoxycarbonyl, benzoxycarbonyl, pyridinylmethoxycarbonyl, trifluoromethylpyridinylmethoxycarbonyl, cyclopropylpyridinylmethoxycarbonyl, phenylethoxycarbonyl, quinolinylmethoxycarbonyl, morpholinoethoxycarbonyl, N,N-dimethylcarbamoyl, morpholinylcarbonyl, N-t-butylcarbamoyl, benzenoyl, nicotinoyl, quinolinoyl, cyclopropanoyl, propanoyl, isobutanoyl, methoxypropanoyl, dimethylaminopropanoyl, trifluoroethyl, trifluoropropyl, trifluoromethylcyclopropyl, methylsulfonyl, trifluoroethylsulfonyl, cyclopropylsulfonyl, phenylsulfonyl, pyridinylsulfonyl, trifluoromethylpyridinylsulfonyl, quinolinylsulfonyl, sulfalmoyl, dimethylsulfamoyl, morpholinylsulfonyl, aminothiadiazolylethyl, tetrahydropyranylethyl, thiophenylethyl,

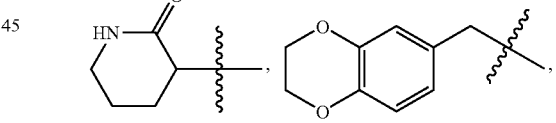

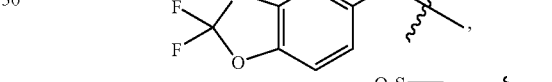

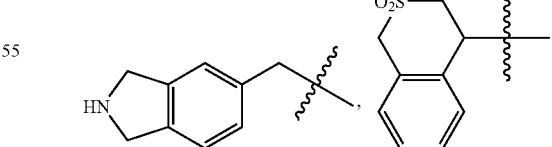

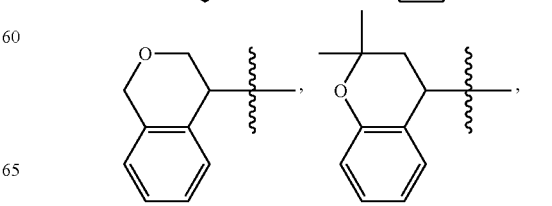

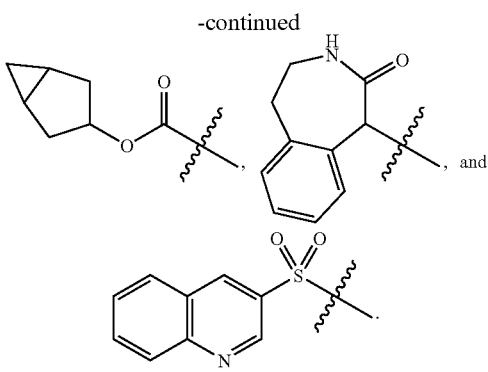, and

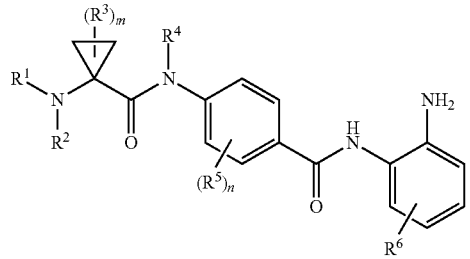.

m is 0, 1, 2, 3 or 4; and R³ is selected from oxo, halo, nitro, cyano, hydroxy, hydroxyalkyl, haloalkyl, haloalkoxy, amino, azido, carboxy, carbamoyl, mercapto, sulphamoyl, $C_{1-10}$ alkyl, $C_{2-10}$ alkenyl, $C_{2-10}$ alkynyl, $C_{1-10}$ alkoxy, $C_{1-10}$ alkanoyl, $C_{3-8}$ cycloalkanoyl, $C_{1-10}$ alkanoyloxy, N—($C_{1-10}$ alkyl)amino, N,N—($C_{1-10}$ alkyl)₂amino, $C_{1-10}$ alkanoylamino, N—($C_{1-10}$ alkyl)carbamoyl, N,N—($C_{1-10}$ alkyl)₂carbamoyl, $C_{1-10}$ alkyl-S(O)ₐ—, wherein a is 0, 1 or 2, $C_{1-10}$ alkoxycarbonyl, NH₂—S(O)₂NH—, N—($C_{1-10}$ alkyl)sulphamoyl, N,N—($C_{1-10}$ alkyl)₂sulphamoyl, cycloalkyl, heterocycloalkyl, aryl, heteroaryl, cycloalkylamino, heterocycloalkylamino or arylamino, wherein R³ is optionally substituted by one or more B where such an optional substitution is chemically feasible, and wherein each B is selected from chloro, hydroxy, oxo, methyl, ethyl, propyl, methoxy, ethoxy, methoxymethyl, ethoxyethyl, propoxyethyl, methoxyethoxy, trifluoromethyl, hydroxyethoxy, dimethylamino, diethylamino, N,N-dimethylaminomethyl, diethylaminomethyl, N,N-dimethylaminoethoxy, trifluoromethoxymethyl, trifluoroethoxymethyl, benzyl, phenylethyl, trifluoromethylphenylethyl, phenoxymethyl, fluorophenoxymethyl, phenylethylaminomethyl, benzylaminomethyl, triazinylmethyl, piperidinylmethyl, piperidinyloxy, trifluoromethylpiperidinylmethyl, pyridinyloxymethyl, pyridinylmethoxy, tetrahydropyrazinyloxy, methylpiperazinylmethyl, pyrrolidin-1-yl, pyrrolidin-2-yl, pyrrolidin-3-yl, pyrrolidin-1-ylmethyl, pyrrolidin-2-ylmethyl, pyrrolidin-3-ylmethyl, pyrrolidin-1-ylethoxy, pyrrolidin-2-ylethoxy, pyrrolidin-3-ylethoxy, imidazol-1-ylmethyl, imidazol-2-ylmethyl, imidazol-4-ylmethyl, imidazolidin-1-yl, imidazolidin-2-yl, imidazolidin-4-yl, imidazolidin-2-ylmethyl, imidazolidin-4-ylmethyl, imidazolin-1-yl, imidazolin-2-yl, imidazolin-4-yl, pyrazolidin-1-yl, pyrazolidin-3-yl, pyrazolidin-4-yl, pyrazolin-1-yl, pyrazolin-3-yl, pyrazolin-4-yl, piperidin-1-yl, piperidin-2-yl, piperidin-3-yl, piperidin-4-yl, piperidin-1-ylmethyl, piperidin-2-ylmethyl, piperidin-3-ylmethyl, piperidin-4-ylmethyl, piperazin-1-yl, piperazin-2-yl, piperazin-3-yl, morpholin-2-yl, morpholin-3-yl, morpholin-4-yl, morpholin-2-ylmethyl, morpholin-3-ylmethyl, morpholin-4-ylmethyl, morpholin-2-ylethoxy, morpholin-3-ylethoxy and morpholin-4-ylethoxy;

when m is 2 and two R³ groups can be substituted at adjacent positions of Cy¹ and form a 5- or 6-membered cyclic moiety to make a fused ring with Cy¹, wherein the cyclic moiety can contain one or more heteroatoms selected from N, O and S;

R⁴ is selected from methyl, cyclopropyl, cyclopropylmethyl, trifluoroethyl, N,N-dimethylaminoethyl, pyrrolidinylethyl, benzyl, pyridinylmethyl, ethylpyridinylmethyl, acetylpiperazinylethyl, methylsulfonamidoethyl, methoxyethyl, methoxycarbonylaminoethyl, pyrazinylaminoethyl, 2-chloro-4-fluorobenzyl, trifluoromethylpyridinylmethyl, imidazolylethyl, imidazolylmethyl, (1-methyl-2,6-dioxopiperidin-4-yl)methyl, 2,5-dioxopyrrolidin-1-ylethyl, N,N-dimethylaminocarbonylmethyl, morpholinocarbonylmethyl, hydroxybutyl, fluorophenyl, and tetrahydro-2H-pyranyl; and
n is 0, 1, 2, 3 or 4; and R⁵ is fluoro or haloalkyl.

In one embodiment, this disclosure provides a compound of Formula (I-a) and a pharmaceutically acceptable salt thereof:

Formula (I-a)

wherein R¹, R², R³, R⁴, R⁵ and R⁶ are as defined above for various aspects of Formula (I).

In an embodiment of Formula (I-a), R¹ and R² are independently selected from the group consisting of H, methyl, tert-butyl, tetrahydrofuran-2-ylmethyl, 2-alkylisoindolin-5-ylmethyl, 1-alkylazetidin-3-yl, 1-alkylpiperidin-3-yl, 1-alkylpyrrolidin-2-yl, cyclopentyl, 2-oxoimidazolidin-1-ylethyl, isochroman-4-yl, 2,2-dimethylchroman-4-yl, 1-alkyl-2-oxopiperidin-3-yl, 2,2,2-trifluoro-1-phenylethyl, 2,2,2-trifluoro-1-(pyridin-2-yl)ethyl, 1-alkylphenylcyclopropyl, 5,5,5-trifluoro-4-hydroxy-4-(trifluoromethyl)pent-2-ynyl, 3-cyclopropylprop-2-ynyl, 4-hydroxy-4-methylpent-2-ynyl, 1-methylcyclopropoxycarbonyl, tert-butoxycarbonyl, 1,1,1-trifluoro-2-methylprop-2-oxycarbonyl, benzoxycarbonyl, pyridin-3-ylmethoxycarbonyl, 5-trifluoromethylpyridin-3-ylmethoxycarbonyl, 5-cyclopropylpyridin-3-ylmethoxycarbonyl, 1-phenylethoxycarbonyl, ylmethoxycarbonyl, 2-morpholinoethoxycarbonyl, N,N-dimethylcarbamoyl, morpholin-4-ylcarbonyl, N-t-butylcarbamoyl, benzenoyl, nicotinoyl, quinolinoyl, cyclopropanoyl, propanoyl, isobutanoyl, methoxypropanoyl, N,N-dimethylaminopropanoyl, 2,2,2-trifluoroethyl, 1,1,1-trifluoroprop-2-yl, 1-trifluoromethylcyclopropyl, methylsulfonyl, 2,2,2-trifluoroethylsulfonyl, cyclopropylsulfonyl, phenylsulfonyl, pyridin-3-ylsulfonyl, 5-trifluoromethylpyridin-3-ylsulfonyl, quinoline-3-sulfonyl, sulfalmoyl, dimethylsulfamoyl, morpholin-4-ylsulfonyl, 1-(carboxymethyl)-2-oxo-piperidin-3-yl, 2-(5-amino-1,3,4-thiadiazol-2-yl)ethyl, and 2-(thiophen-2-yl) ethyl; m is 0, 1 or 2 and each R³ is independently selected from methyl, ethyl, bromo, and trifluoromethyl; R⁴ is selected from the group consisting of methyl, cyclopropyl, cyclopropylmethyl, trifluoroethyl, N,N-dimethylaminoethyl, pyrrolidin-1-ylethyl, benzyl, pyridin-2-ylmethyl, (1-ethylpyridin-4-yl)methyl, 4-acetylpiperazin-1-ylethyl, methylsulfonamidoethyl, methoxyethyl, methoxycarbonylaminoethyl, pyrazin-2-ylaminoethyl, 2-chloro-4-fluorobenzyl, (5-(trifluoromethyl)pyridin-2-yl)methyl, (1H-imidazol-1-yl)ethyl, (1H-imidazol-2-yl)methyl, (1-methyl-2,6-dioxopiperidin-4-yl)methyl, 2,5-dioxopyrrolidin-1-ylethyl, N,N-dimethylcarbamoyl, 2-morpholino-2-oxoethyl, 2-hydroxy-2-methylpropyl, 4-fluorophenyl, and tetrahydro-2H-pyran-4-yl; n is 0, 1, 2, 3 or 4 and each R⁵ is independently selected from halo, hydroxy, alkyl and haloalkyl; and R⁶ is selected from fluoro, trifluoromethyl, phenyl, fluorophenyl, thiophenyl, chlorothiophenyl, and methylthiophenyl.

Non-limiting examples of such compounds include compounds of Formula (I-a1) and pharmaceutically acceptable salts thereof:

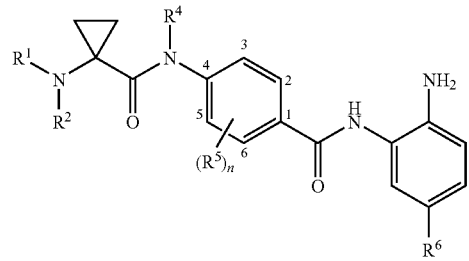

Formula (I-a1)

| Comp. No. | R$^1$ | R$^2$ | R$^4$ | R$^5$ | R$^6$ |
|---|---|---|---|---|---|
| a1-1 | H | H | H | H | H |
| a1-2 | H | H | —CH$_3$ | H | H |
| a1-3 | H | H | H | —F (position 3) | H |
| a1-4 | H | H | —CH$_3$ | —F (position 3) | H |
| a1-5 | H | H | H | H | 2-thienyl |
| a1-6 | H | H | —CH$_3$ | H | 2-thienyl |
| a1-7 | H | H | H | —F (position 3) | 2-thienyl |
| a1-8 | H | H | —CH$_3$ | —F (position 3) | 2-thienyl |
| a1-9 | H | H | H | H | 4-phenyl |
| a1-10 | H | H | —CH$_3$ | H | 4-phenyl |
| a1-11 | H | H | H | —F (position 3) | 4-phenyl |
| a1-12 | H | H | —CH$_3$ | —F (position 3) | 4-phenyl |
| a1-13 | H | H | H | H | 5-chloro-2-thienyl |

-continued

Formula (I-a1)

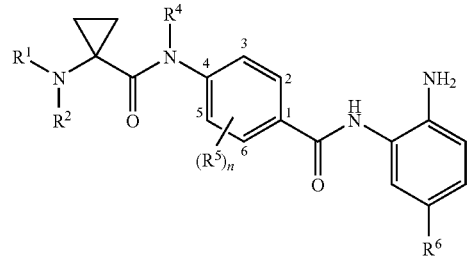

| Comp. No. | R¹ | R² | R⁴ | R⁵ | R⁶ |
|---|---|---|---|---|---|
| a1-14 | H | H | —CH₃ | H | 5-chlorothien-2-yl |
| a1-15 | H | H | H | —F (position 3) | 5-chlorothien-2-yl |
| a1-16 | H | H | —CH₃ | —F (position 3) | 5-chlorothien-2-yl |
| a1-17 | H | tert-butoxycarbonyl-methyl | H | H | H |
| a1-18 | H | tert-butoxycarbonyl-methyl | —CH₃ | H | H |
| a1-19 | H | tert-butoxycarbonyl-methyl | H | —F (position 3) | H |
| a1-20 | H | tert-butoxycarbonyl-methyl | —CH₃ | —F (position 3) | H |
| a1-21 | H | tert-butoxycarbonyl-methyl | H | H | thien-2-yl |
| a1-22 | H | tert-butoxycarbonyl-methyl | —CH₃ | H | thien-2-yl |
| a1-23 | H | tert-butoxycarbonyl-methyl | H | —F (position 3) | thien-2-yl |

-continued

Formula (I-a1)

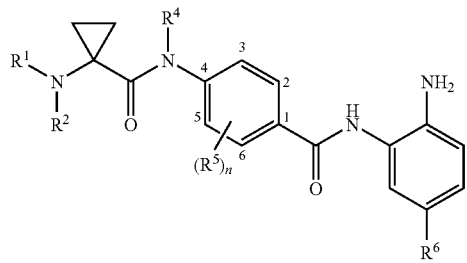

| Comp. No. | R¹ | R² | R⁴ | R⁵ | R⁶ |
|---|---|---|---|---|---|
| a1-24 | H | tert-butyl ester group | —CH₃ | —F (position 3) | 2-thienyl |
| a1-25 | H | tert-butyl ester group | H | H | phenyl |
| a1-26 | H | tert-butyl ester group | —CH₃ | H | phenyl |
| a1-27 | H | tert-butyl ester group | H | —F (position 3) | phenyl |
| a1-28 | H | tert-butyl ester group | —CH₃ | —F (position 3) | phenyl |
| a1-29 | H | tert-butyl ester group | H | H | 5-chloro-2-thienyl |
| a1-30 | H | tert-butyl ester group | —CH₃ | H | 5-chloro-2-thienyl |
| a1-31 | H | tert-butyl ester group | H | —F (position 3) | 5-chloro-2-thienyl |
| a1-32 | H | tert-butyl ester group | —CH₃ | —F (position 3) | 5-chloro-2-thienyl |

-continued
Formula (I-a1)
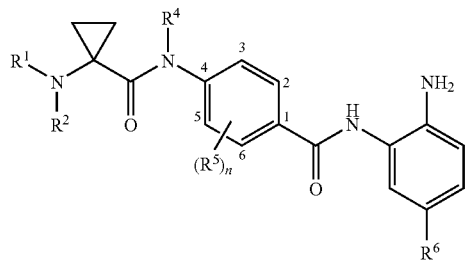
| Comp. No. | R¹ | R² | R⁴ | R⁵ | R⁶ |
|---|---|---|---|---|---|
| a1-33 | H | benzyl ester (PhCH₂OC(O)-) | H | H | H |
| a1-34 | H | benzyl ester | —CH₃ | H | H |
| a1-35 | H | benzyl ester | H | —F (position 3) | H |
| a1-36 | H | benzyl ester | —CH₃ | —F (position 3) | H |
| a1-37 | H | benzyl ester | H | H | 2-thienyl |
| a1-38 | H | benzyl ester | —CH₃ | H | 2-thienyl |
| a1-39 | H | benzyl ester | H | —F (position 3) | 2-thienyl |
| a1-40 | H | benzyl ester | —CH₃ | —F (position 3) | 2-thienyl |

-continued
Formula (I-a1)
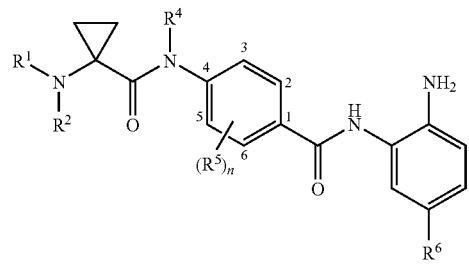
| Comp. No. | R¹ | R² | R⁴ | R⁵ | R⁶ |
|---|---|---|---|---|---|
| a1-41 | H | benzyl ester | H | H | 4-phenyl |
| a1-42 | H | benzyl ester | —CH₃ | H | 4-phenyl |
| a1-43 | H | benzyl ester | H | —F (position 3) | 4-phenyl |
| a1-44 | H | benzyl ester | —CH₃ | —F (position 3) | 4-phenyl |
| a1-45 | H | benzyl ester | H | H | 5-chlorothiophen-2-yl |
| a1-46 | H | benzyl ester | —CH₃ | H | 5-chlorothiophen-2-yl |
| a1-47 | H | benzyl ester | H | —F (position 3) | 5-chlorothiophen-2-yl |
| a1-48 | H | benzyl ester | —CH₃ | —F (position 3) | 5-chlorothiophen-2-yl |

-continued
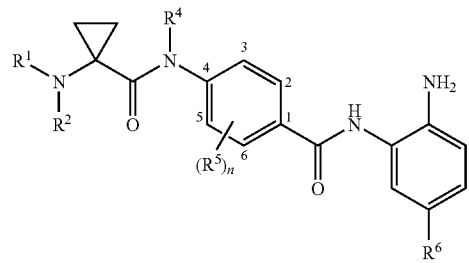
Formula (I-a1)
| Comp. No. | R¹ | R² | R⁴ | R⁵ | R⁶ |
|---|---|---|---|---|---|
| a1-49 | H | t-Bu-NH-C(O)-C(CH₃)- | H | H | H |
| a1-50 | H | t-Bu-NH-C(O)-C(CH₃)- | —CH₃ | H | H |
| a1-51 | H | t-Bu-NH-C(O)-C(CH₃)- | H | —F (position 3) | H |
| a1-52 | H | t-Bu-NH-C(O)-C(CH₃)- | —CH₃ | —F (position 3) | H |
| a1-53 | H | t-Bu-NH-C(O)-C(CH₃)- | H | H | 2-thienyl |
| a1-54 | H | t-Bu-NH-C(O)-C(CH₃)- | —CH₃ | H | 2-thienyl |
| a1-55 | H | t-Bu-NH-C(O)-C(CH₃)- | H | —F (position 3) | 2-thienyl |
| a1-56 | H | t-Bu-NH-C(O)-C(CH₃)- | —CH₃ | —F (position 3) | 2-thienyl |
| a1-57 | H | t-Bu-NH-C(O)-C(CH₃)- | H | H | 4-methylphenyl |

Formula (I-a1)
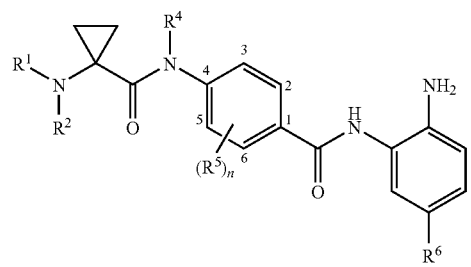
| Comp. No. | R¹ | R² | R⁴ | R⁵ | R⁶ |
|---|---|---|---|---|---|
| a1-58 | H | 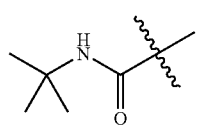 | —CH₃ | H | 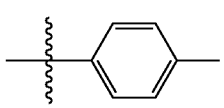 |
| a1-59 | H | 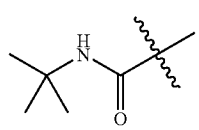 | H | —F (position 3) | 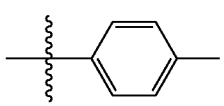 |
| a1-60 | H | 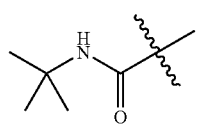 | —CH₃ | —F (position 3) | 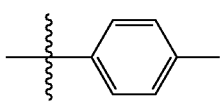 |
| a1-61 | H | 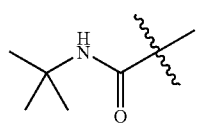 | H | H | 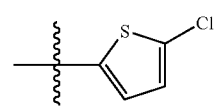 |
| a1-62 | H | 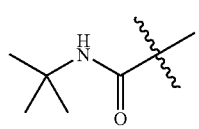 | —CH₃ | H | 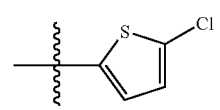 |
| a1-63 | H | 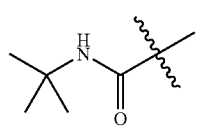 | H | —F (position 3) | 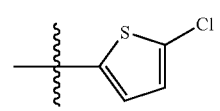 |
| a1-64 | H | 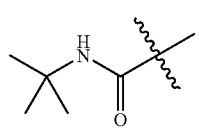 | —CH₃ | —F (position 3) | 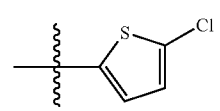 |

In one embodiment, the invention provides a compound of Formula (I-b) and a pharmaceutically acceptable salt thereof:

Formula (I-b)

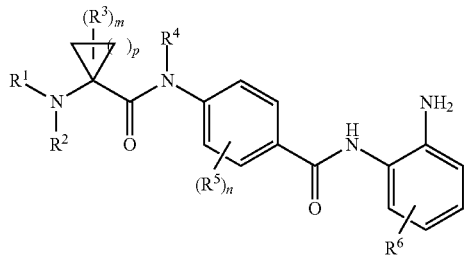

wherein $R^1$, $R^2$, $R^3$, $R^4$, $R^5$ and $R^6$ are as defined above for various aspects of Formula (I); p is 2, 3, 4, 5, or 6. Therefore, $Cy^1$ of Formula (I-b) includes cyclobutylidene, cyclopentylidene, cyclohexylidene, cycloheptylidene and cyclooctylidene.

In an embodiment of Formula (I-b), p is 3; and $R^1$, $R^2$, $R^3$, $R^4$, $R^5$ and $R^6$ are as defined above for various aspects of Formula (I-a). Non-limiting examples of such compounds include compounds of Formula (I-b1) and pharmaceutically acceptable salts thereof:

Formula (I-b1)

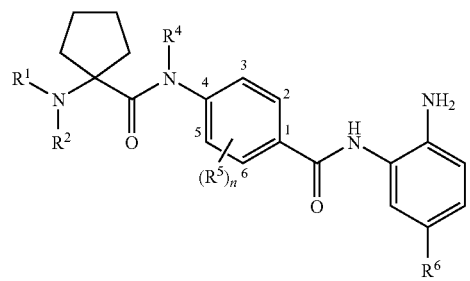

| Comp. No. | $R^1$ | $R^2$ | $R^4$ | $R^5$ | $R^6$ |
|---|---|---|---|---|---|
| b1-1 | H | H | H | H | H |
| b1-2 | H | H | —CH₃ | H | H |
| b1-3 | H | H | H | —F (position 3) | H |
| b1-4 | H | H | —CH₃ | —F (position 3) | H |
| b1-5 | H | H | H | H | 2-thienyl |
| b1-6 | H | H | —CH₃ | H | 2-thienyl |
| b1-7 | H | H | H | —F (position 3) | 2-thienyl |
| b1-8 | H | H | —CH₃ | —F (position 3) | 2-thienyl |
| b1-9 | H | H | H | H | 4-fluorophenyl |
| b1-10 | H | H | —CH₃ | H | 4-fluorophenyl |

-continued
| | | | | | |
|---|---|---|---|---|---|
| b1-11 | H | H | H | —F (position 3) | 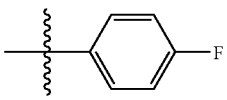 |
| b1-12 | H | H | —CH$_3$ | —F (position 3) | 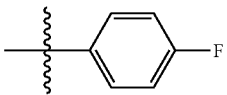 |
| b1-13 | H | H | H | H | 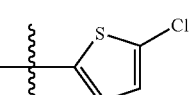 |
| b1-14 | H | H | —CH$_3$ | H | 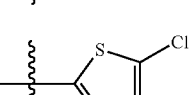 |
| b1-15 | H | H | H | —F (position 3) | 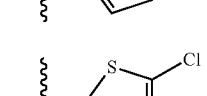 |
| b1-16 | H | H | —CH$_3$ | —F (position 3) | 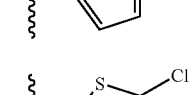 |
| b1-17 | H | 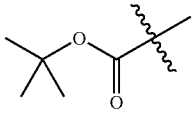 | H | H | H |
| b1-18 | H | 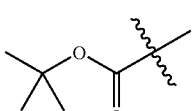 | —CH$_3$ | H | H |
| b1-19 | H | 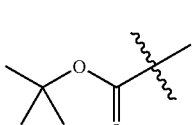 | H | —F (position 3) | H |
| b1-20 | H | 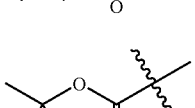 | —CH$_3$ | —F (position 3) | H |
| b1-21 | H | 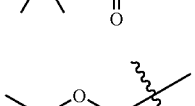 | H | H | 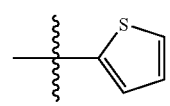 |
| b1-22 | H | 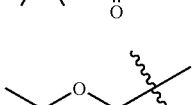 | —CH$_3$ | H | 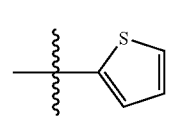 |
| b1-23 | H | 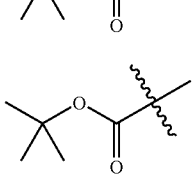 | H | —F (position 3) | 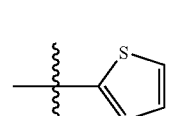 |

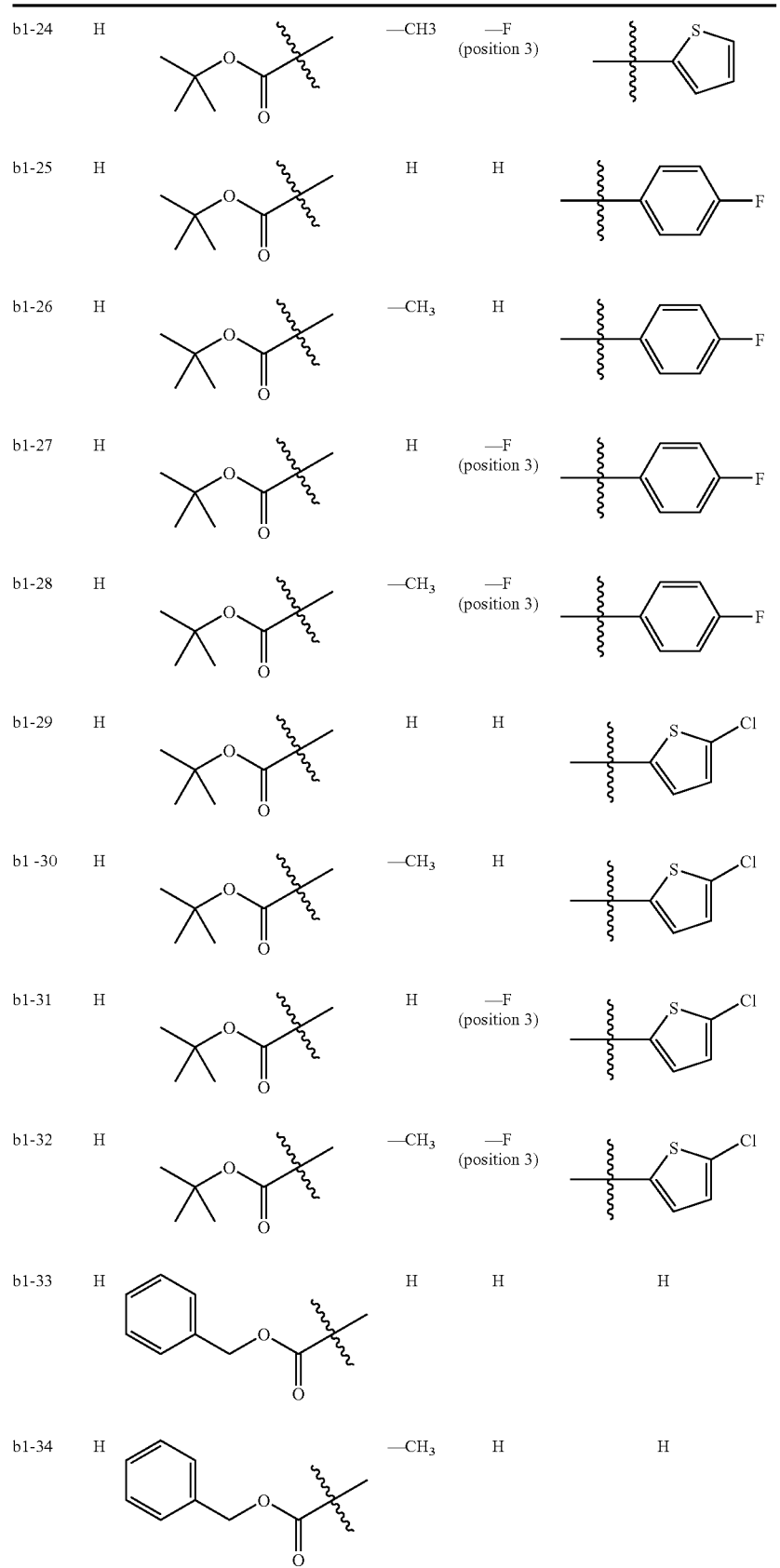

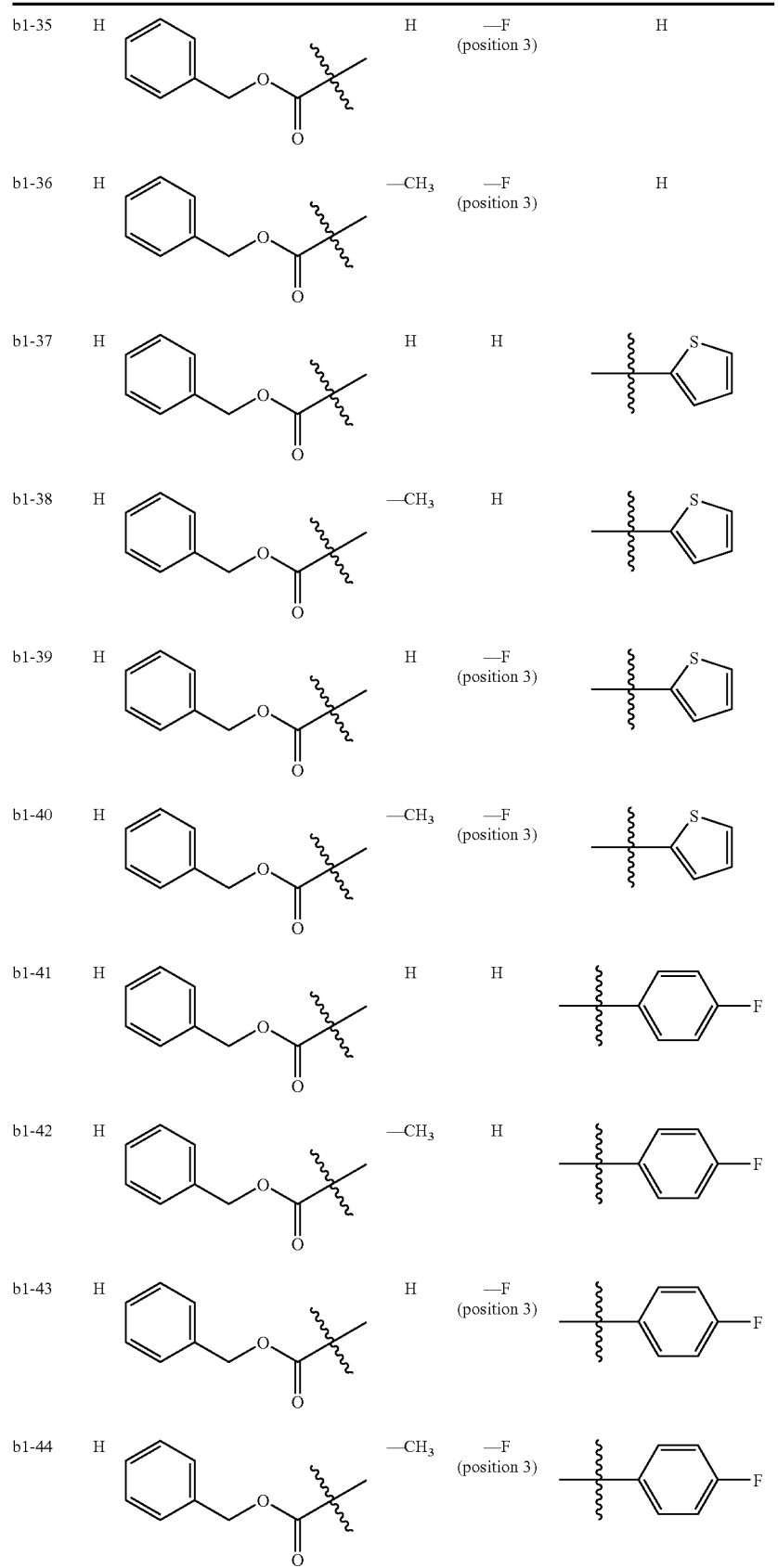

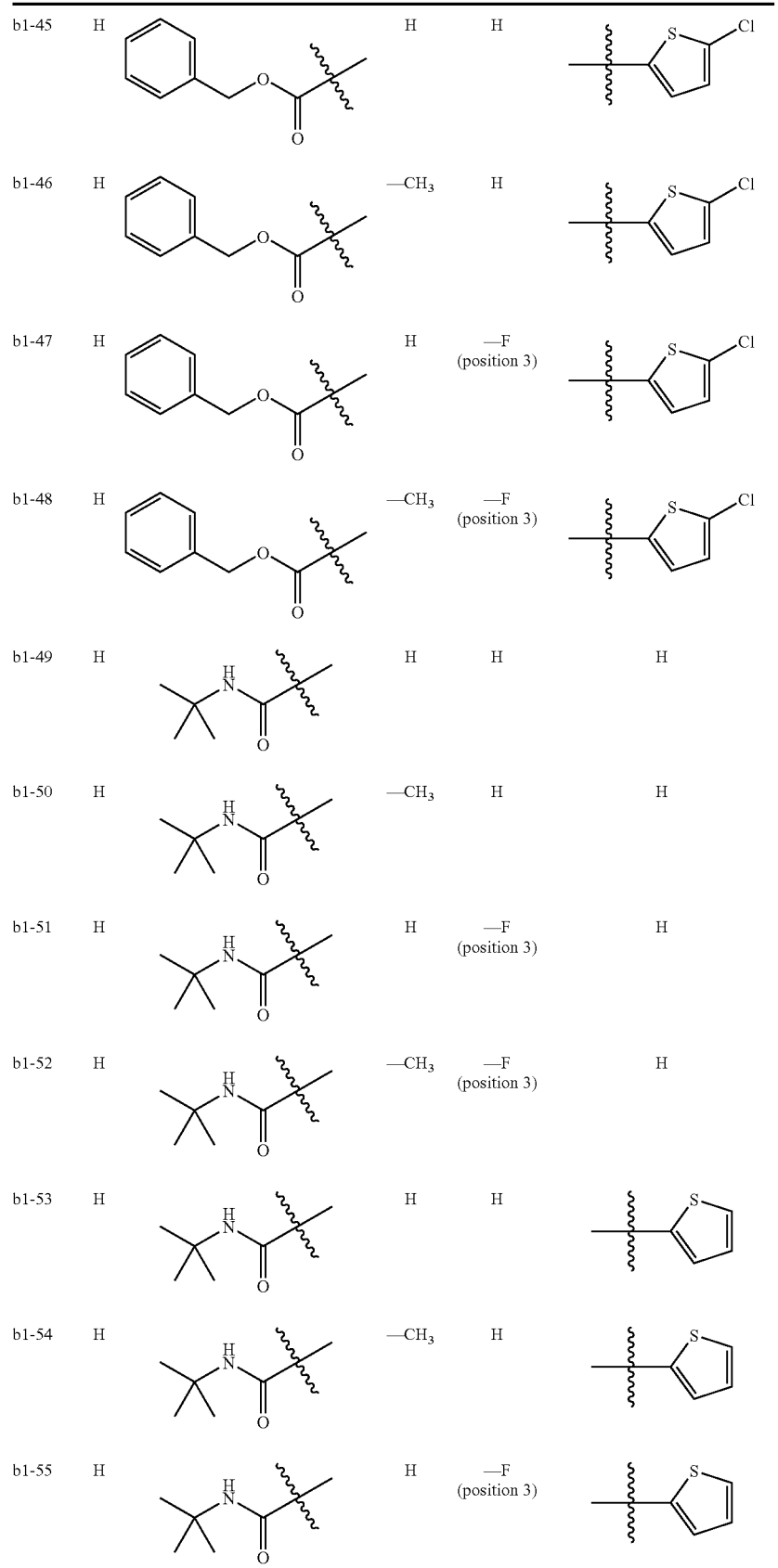

-continued
| | | | | | |
|---|---|---|---|---|---|
| b1-56 | H | 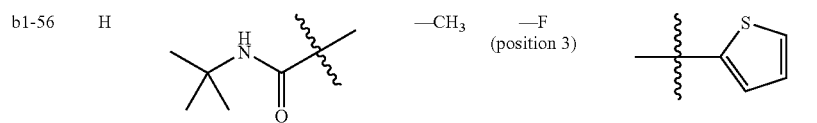 | —CH₃ | —F (position 3) | |
| b1-57 | H | 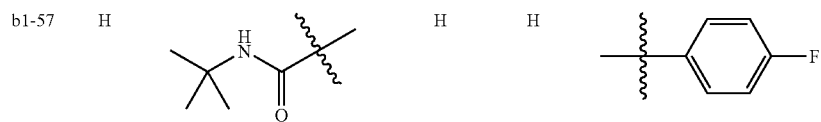 | H | H | |
| b1-58 | H | 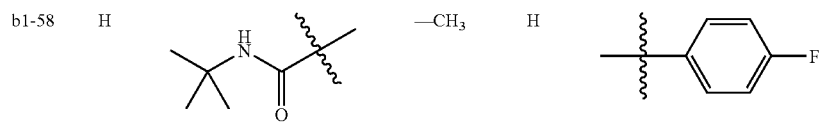 | —CH₃ | H | |
| b1-59 | H | 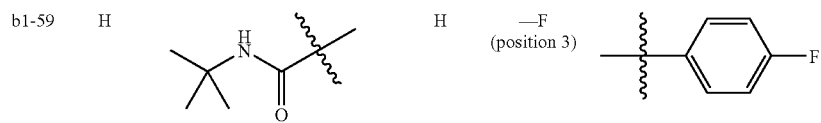 | H | —F (position 3) | |
| b1-60 | H | 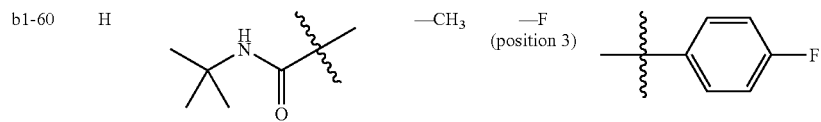 | —CH₃ | —F (position 3) | |
| b1-61 | H | 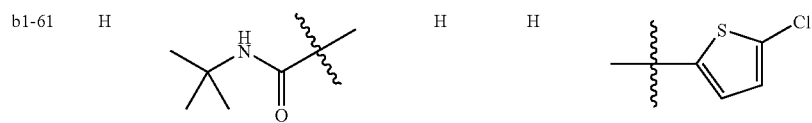 | H | H | |
| b1-62 | H | 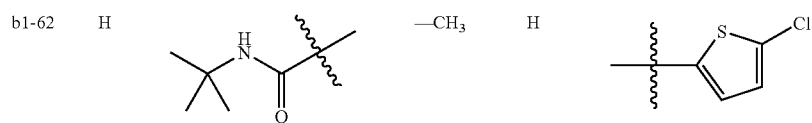 | —CH₃ | H | |
| b1-63 | H | 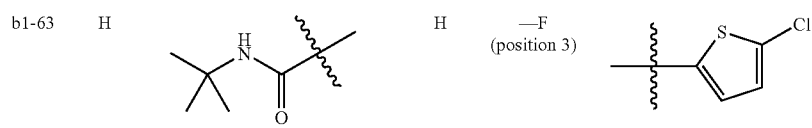 | H | —F (position 3) | |
| b1-64 | H | 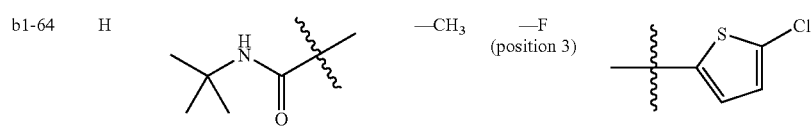 | —CH₃ | —F (position 3) | |

In an embodiment of Formula (I-b), p is 4; and $R^1$, $R^2$, $R^3$, $R^4$, $R^5$ and $R^6$ are as defined above for various aspects of Formula (I-a). Non-limiting examples of such compounds include compounds of Formula (I-b2) and pharmaceutically acceptable salts thereof:

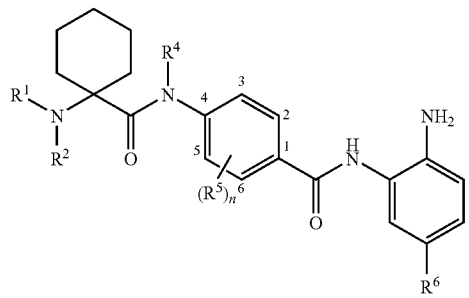

Formula (I-b2)

| Comp. No. | $R^1$ | $R^2$ | $R^4$ | $R^5$ | $R^6$ |
|---|---|---|---|---|---|
| b2-1 | H | H | H | H | H |
| b2-2 | H | H | —CH$_3$ | H | H |
| b2-3 | H | H | H | —F (position 3) | H |
| b2-4 | H | H | —CH$_3$ | —F (position 3) | H |
| b2-5 | H | H | H | H | thiophene |
| b2-6 | H | H | —CH$_3$ | H | thiophene |
| b2-7 | H | H | H | —F (position 3) | thiophene |
| b2-8 | H | H | —CH$_3$ | —F (position 3) | thiophene |
| b2-9 | H | H | H | H | 4-F-phenyl |
| b2-10 | H | H | —CH$_3$ | H | 4-F-phenyl |
| b2-11 | H | H | H | —F (position 3) | 4-F-phenyl |
| b2-12 | H | H | —CH$_3$ | —F (position 3) | 4-F-phenyl |

-continued
| | | | | | |
|---|---|---|---|---|---|
| b2-13 | H | H | H | H | 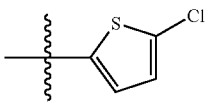 |
| b2-14 | H | H | —CH₃ | H | 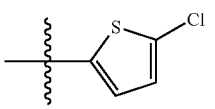 |
| b2-15 | H | H | H | —F (position 3) | 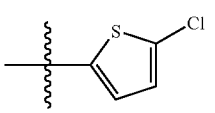 |
| b2-16 | H | H | —CH₃ | —F (position 3) | 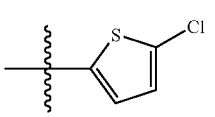 |
| b2-17 | H | 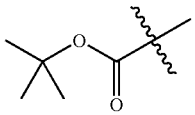 | H | H | H |
| b2-18 | H | 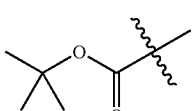 | —CH₃ | H | H |
| b2-19 | H | 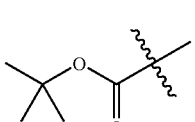 | H | —F (position 3) | H |
| b2-20 | H | 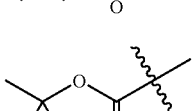 | —CH₃ | —F (position 3) | H |
| b2-21 | H | 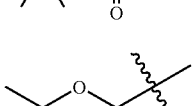 | H | H | 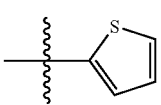 |
| b2-22 | H | 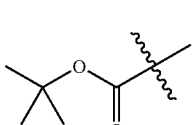 | —CH₃ | H | 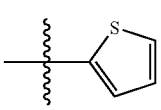 |
| b2-23 | H | 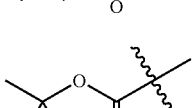 | H | —F (position 3) | 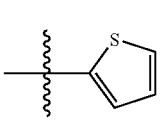 |
| b2-24 | H | 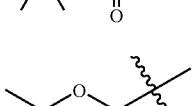 | —CH₃ | —F (position 3) | 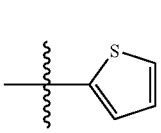 |
| b2-25 | H | 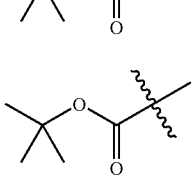 | H | H | 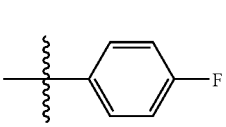 |

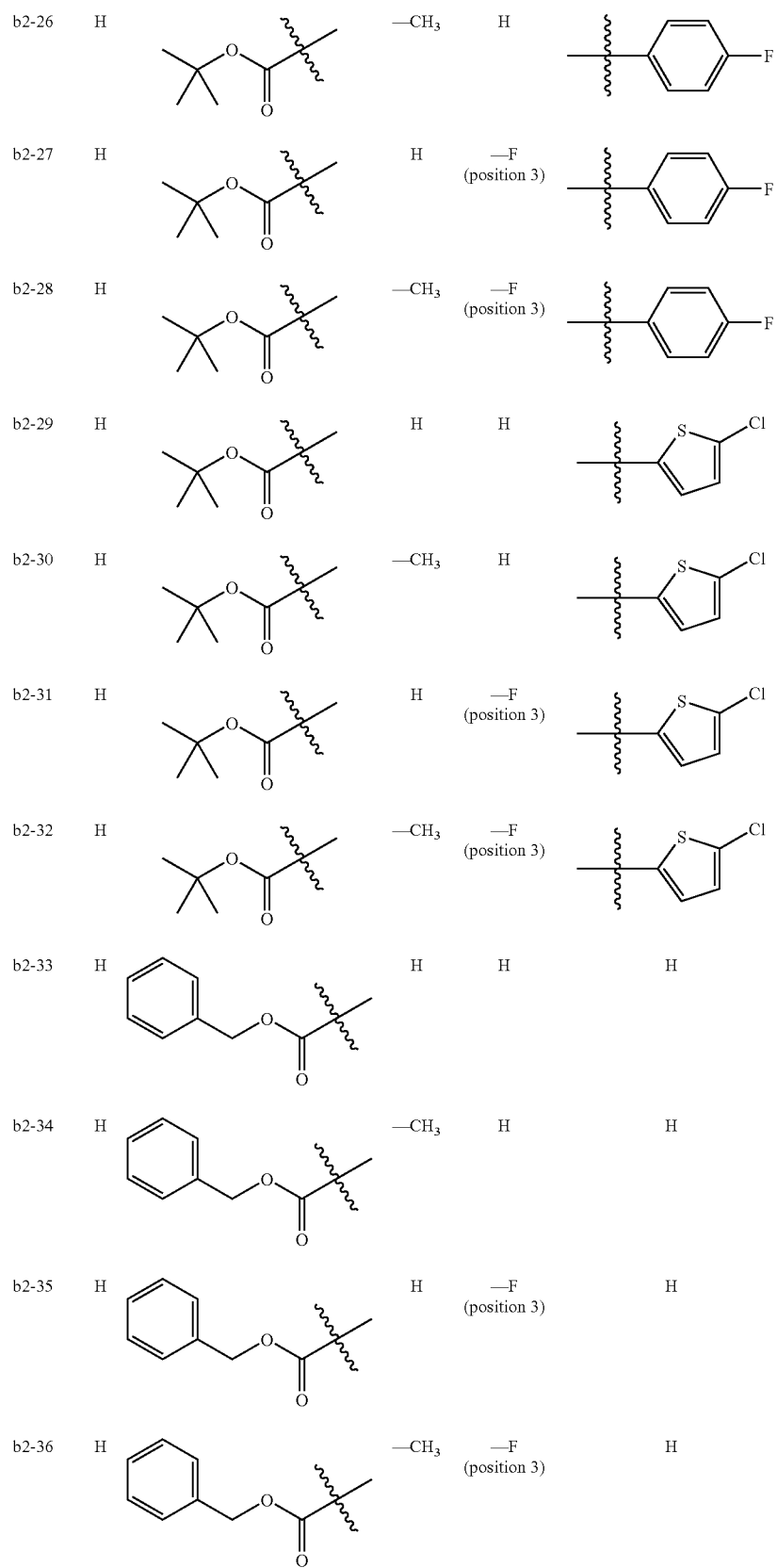

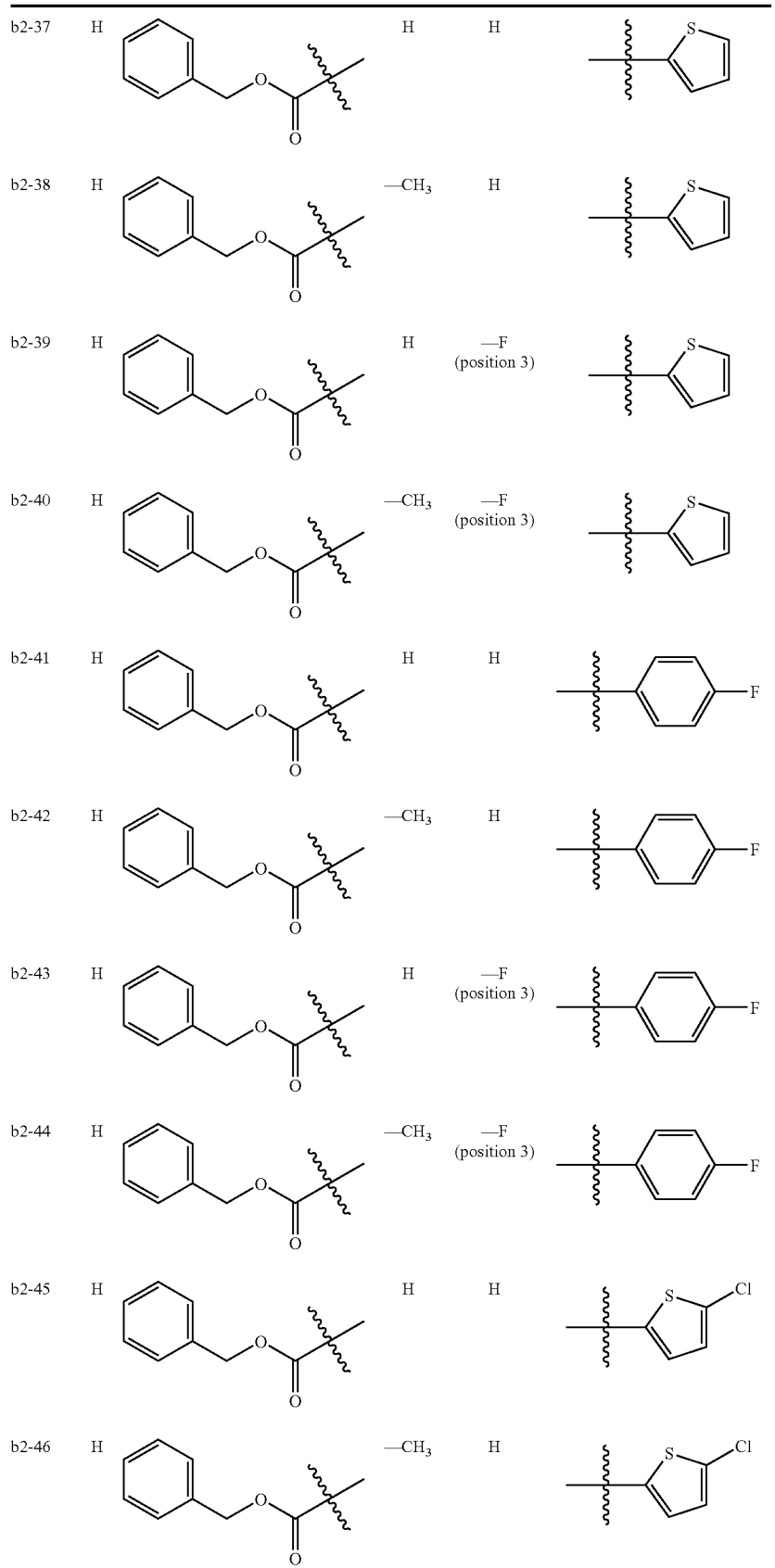

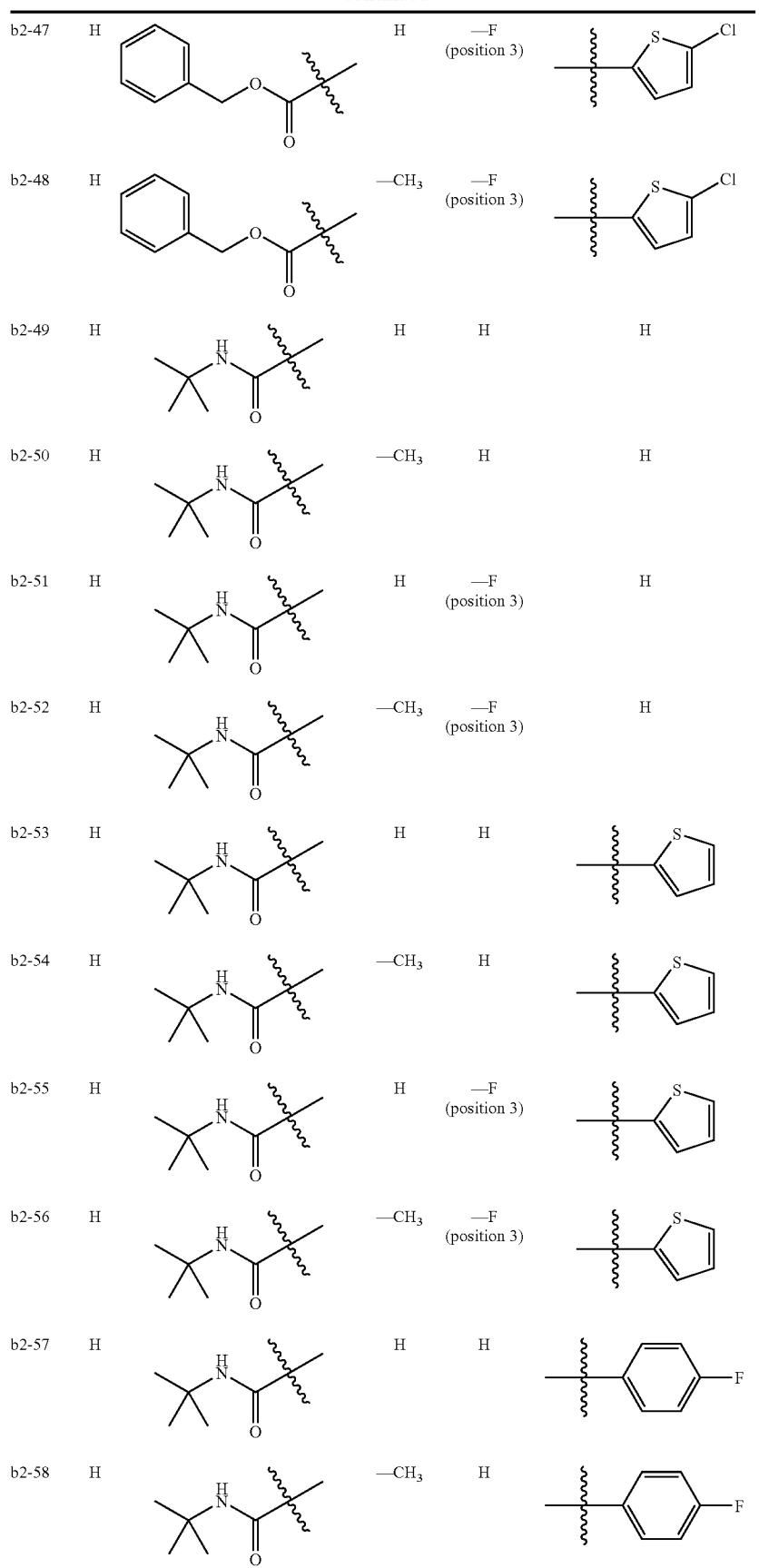

-continued

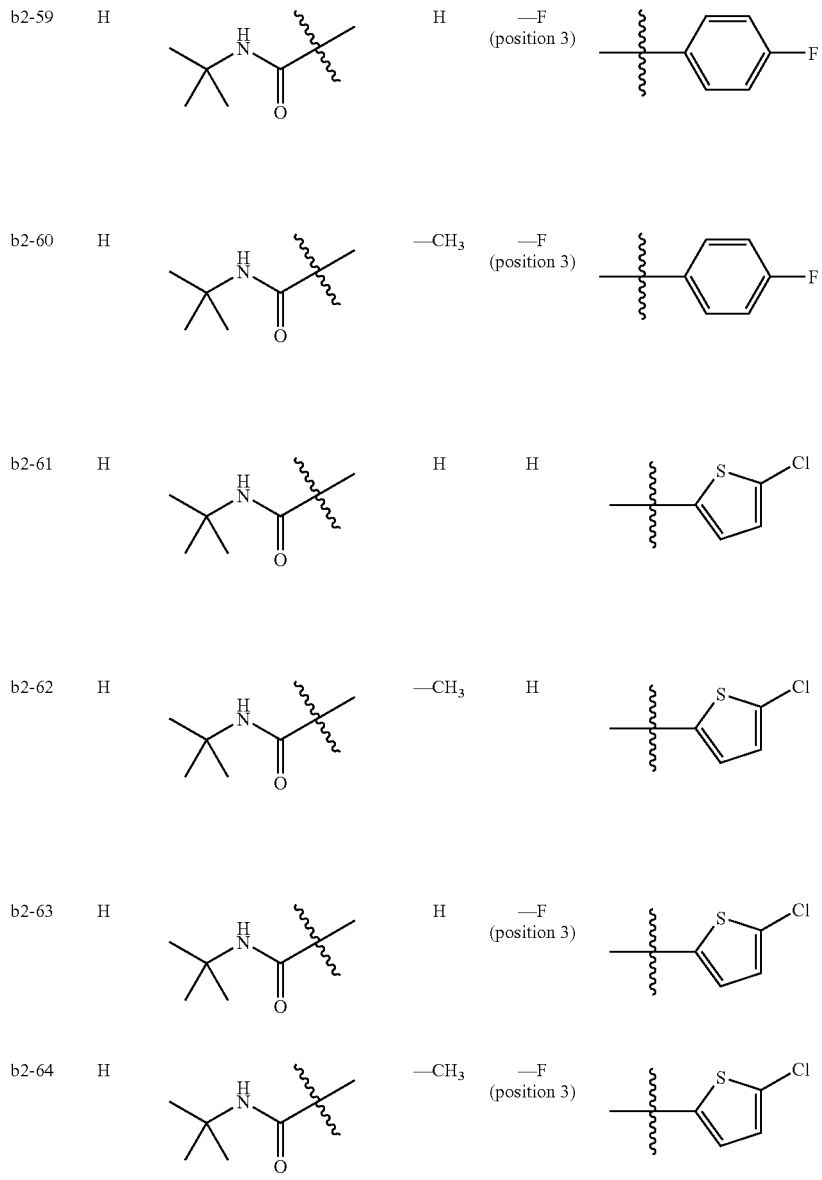

In one embodiment, the invention provides a compound of Formula (I-c) and a pharmaceutically acceptable salt thereof:

Formula (I-c)

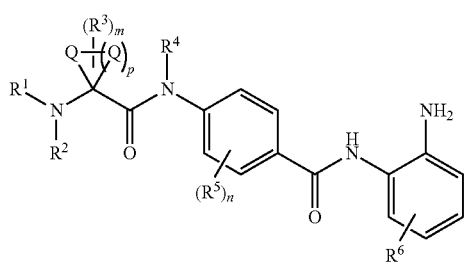

wherein $R^1$, $R^2$, $R^3$, $R^4$, $R^5$ and $R^6$ are as defined above for various aspects of Formula (I); p is 1, 2, 3, 4 or 5; and each Q ring atom is independently selected from C, N, O and S, and wherein at least one Q is non-carbon ring atom. Therefore, $Cy^1$ of Formula (I-c) embraces 3- to 7-membered heterocycloalkylidenes.

In an embodiment of Formula (I-c), p is 5; and $R^1$, $R^2$, $R^3$, $R^4$, $R^5$ and $R^6$ are as defined above for various aspects of Formula (I-a). Non-limiting examples of such compounds include compounds of Formula (I-c1) and pharmaceutically acceptable salts thereof:

Formula (I-c1)
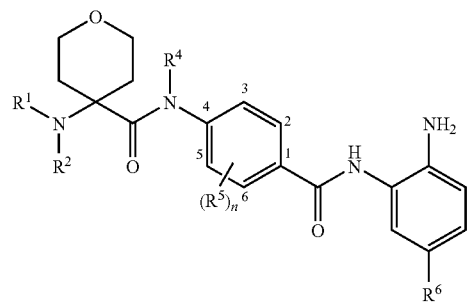
| Comp. No. | R¹ | R² | R⁴ | R⁵ | R⁶ |
|---|---|---|---|---|---|
| c1-1 | H | H | H | H | H |
| c1-2 | H | H | —CH₃ | H | H |
| c1-3 | H | H | H | —F (position 3) | H |
| c1-4 | H | H | —CH₃ | —F (position 3) | H |
| c1-5 | H | H | H | H | ![thiophene] |
| c1-6 | H | H | —CH₃ | H | ![thiophene] |
| c1-7 | H | H | H | —F (position 3) | ![thiophene] |
| c1-8 | H | H | —CH₃ | —F (position 3) | ![thiophene] |
| c1-9 | H | H | H | H | ![4-F-phenyl] |
| c1-10 | H | H | —CH₃ | H | ![4-F-phenyl] |
| c1-11 | H | H | H | —F (position 3) | ![4-F-phenyl] |
| c1-12 | H | H | —CH₃ | —F (position 3) | ![4-F-phenyl] |
| c1-13 | H | H | H | H | ![5-Cl-thiophene] |

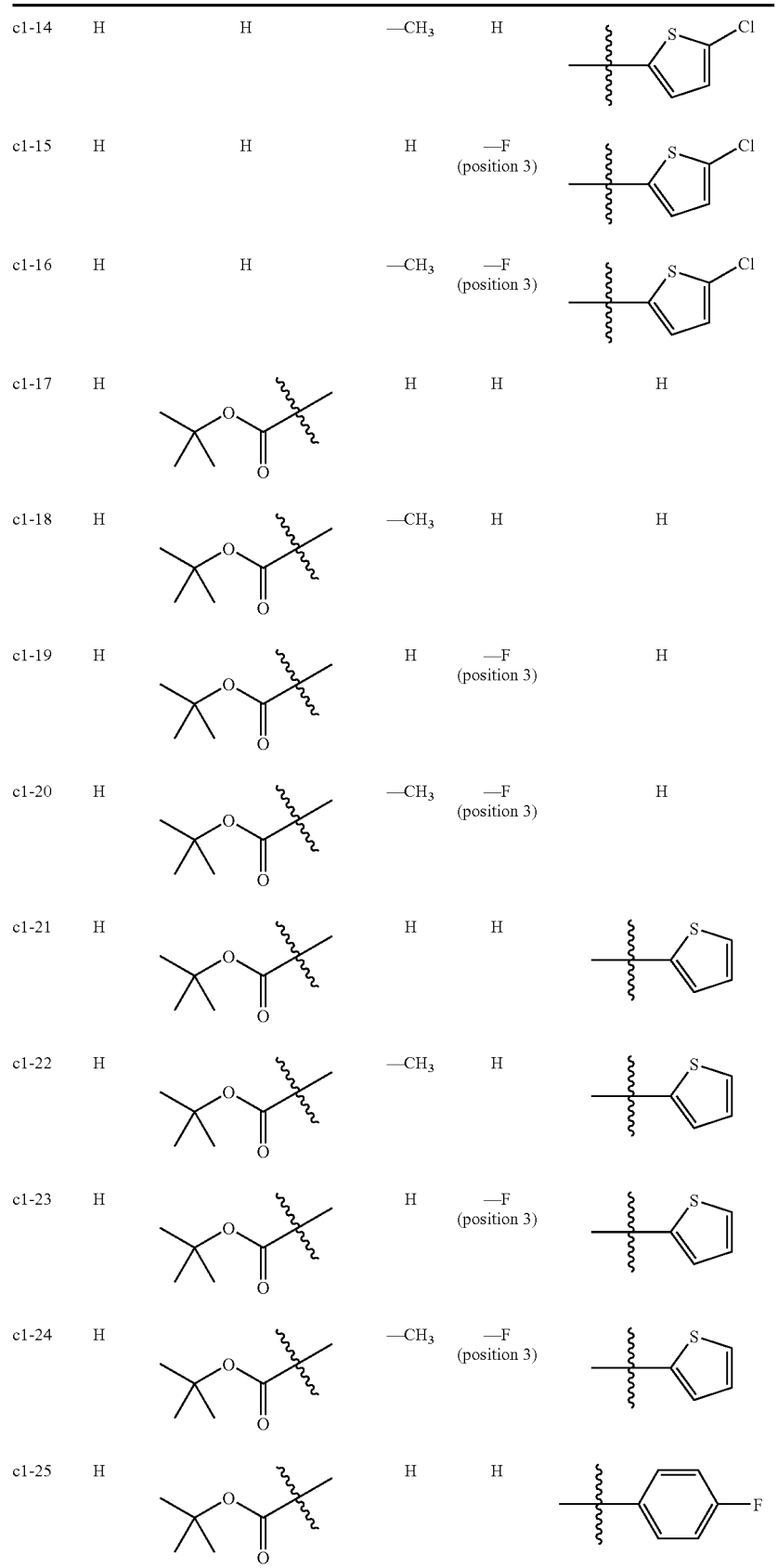

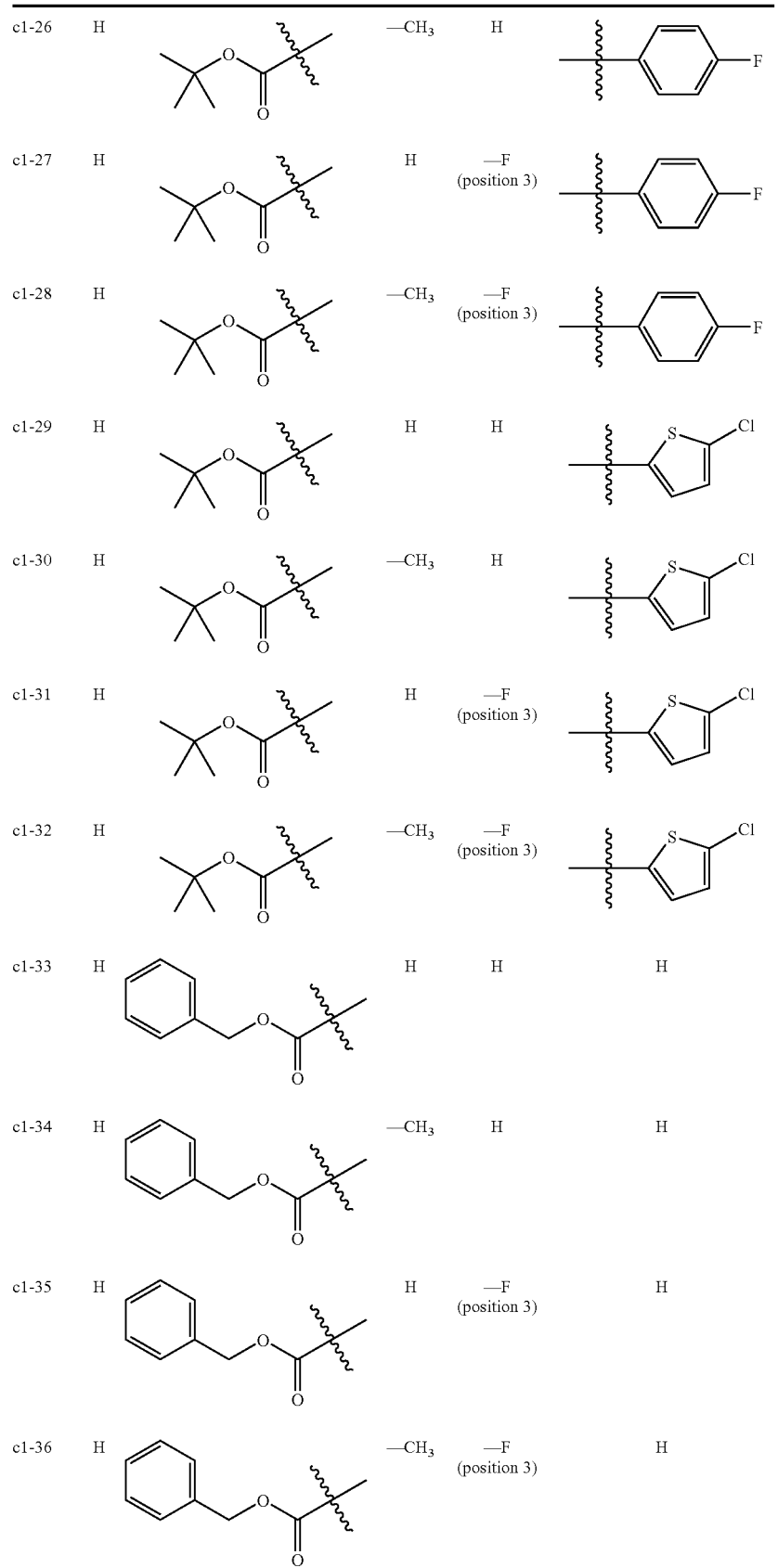

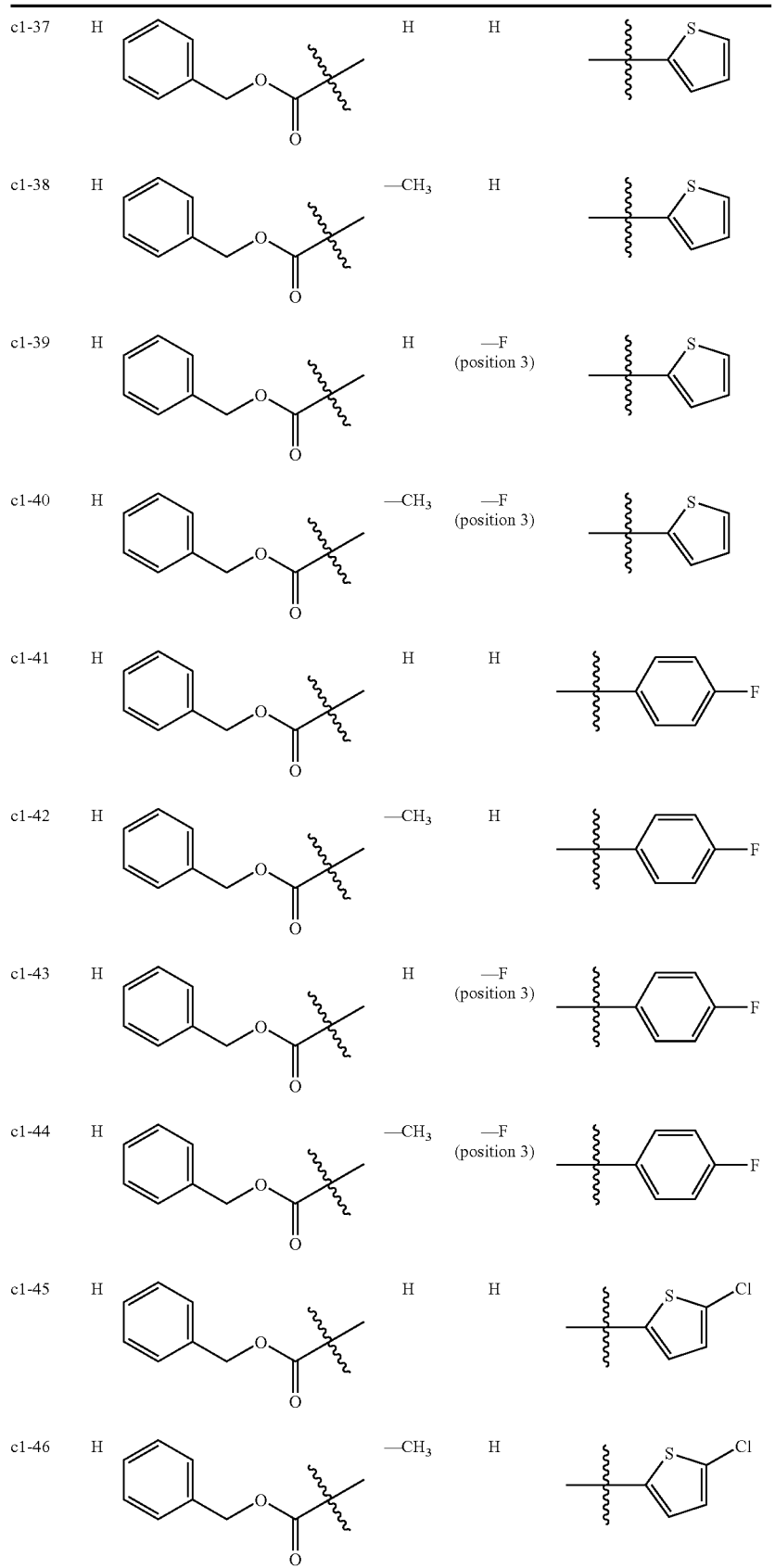

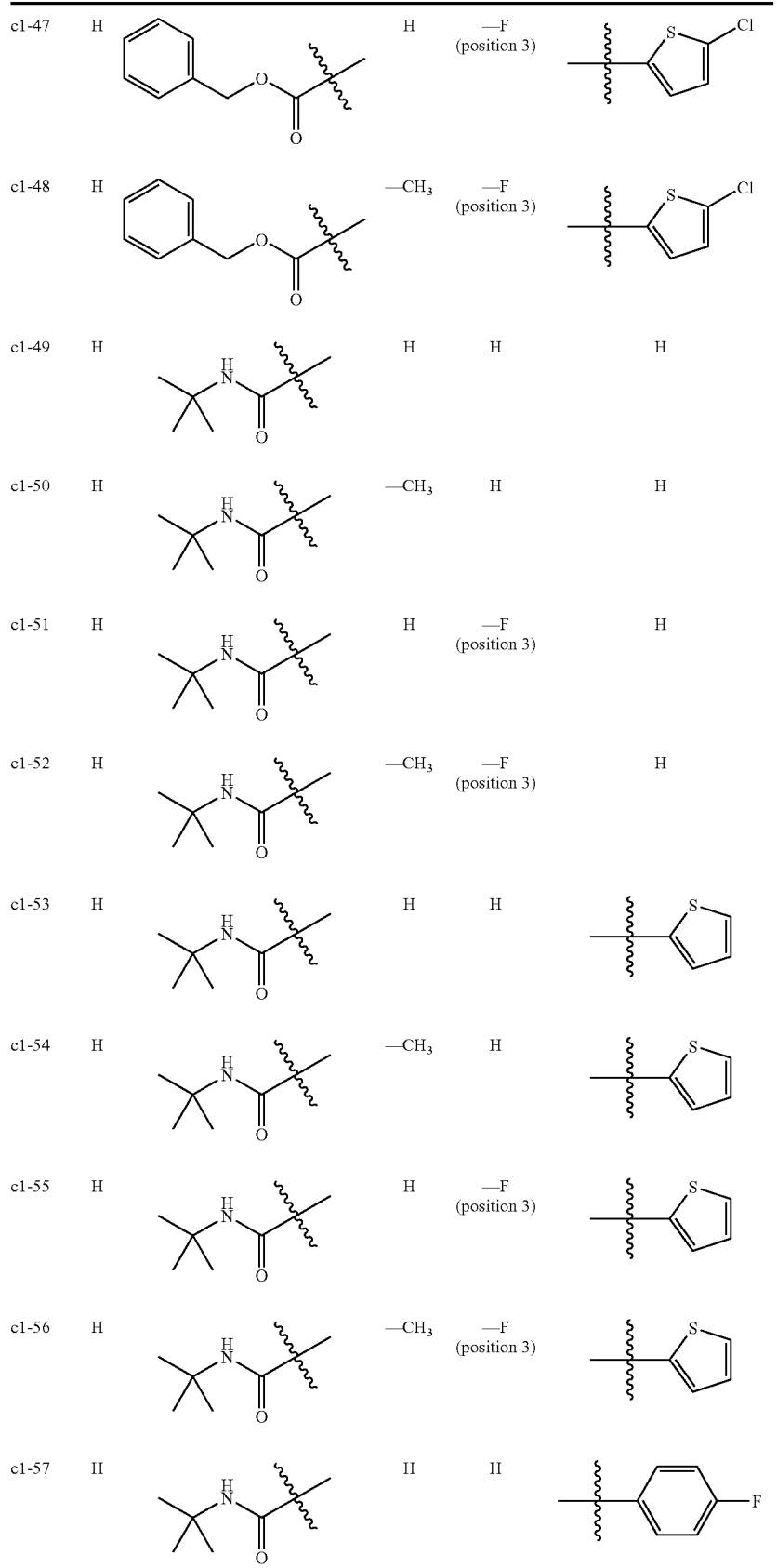

-continued

| | | | | |
|---|---|---|---|---|
| c1-58 | H | ![structure: tBuNHC(O)C(CH3)-] | —CH₃ | H | ![4-F-phenyl] |
| c1-59 | H | ![structure: tBuNHC(O)C(CH3)-] | H | —F (position 3) | ![4-F-phenyl] |
| c1-60 | H | ![structure: tBuNHC(O)C(CH3)-] | —CH₃ | —F (position 3) | ![4-F-phenyl] |
| c1-61 | H | ![structure: tBuNHC(O)C(CH3)-] | H | H | ![5-Cl-thienyl] |
| c1-62 | H | ![structure: tBuNHC(O)C(CH3)-] | —CH₃ | H | ![5-Cl-thienyl] |
| c1-63 | H | ![structure: tBuNHC(O)C(CH3)-] | H | —F (position 3) | ![5-Cl-thienyl] |
| c1-64 | H | ![structure: tBuNHC(O)C(CH3)-] | —CH₃ | —F (position 3) | ![5-Cl-thienyl] |

In yet another embodiment, there is provided a compound selected from those of Formula (II) and pharmaceutically accepted salts thereof:

Formula (II)

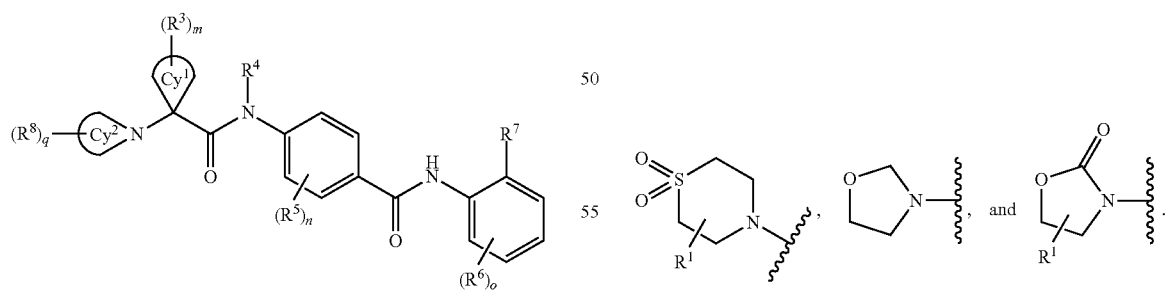

wherein m, n, o, q Cy¹, Cy², R³, R⁴, R⁵, R⁶, R⁷, and R⁸ are as defined above.

In an embodiment, Cy² is heterocyclyl containing 4, 5 or 6 ring atoms, one of which is a nitrogen ring atom attached to the remaining molecule, wherein the heterocyclyl is optionally substituted with one or more R⁷. Non-limiting examples of such heterocyclyls include pyrrolidinyl, oxopyrrolidinyl, morpholinyl, piperazinyl, piperidinyl, azetidinyl,

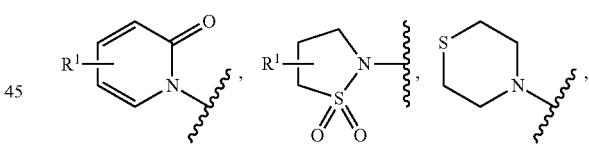

In a particular embodiment, Cy² is pyrrolidinyl or pyrrolidinyl fused with a saturated or unsaturated ring structure, wherein Cy is optionally substituted with one or more R⁷.

In one embodiment, Cy is pyrrolidinyl fused with a saturated or unsaturated ring structure having 5 or 6 ring members, wherein the cyclic moiety can contain one or more heteroatoms selected from N, O and S. Non-limiting examples of such fused rings include:

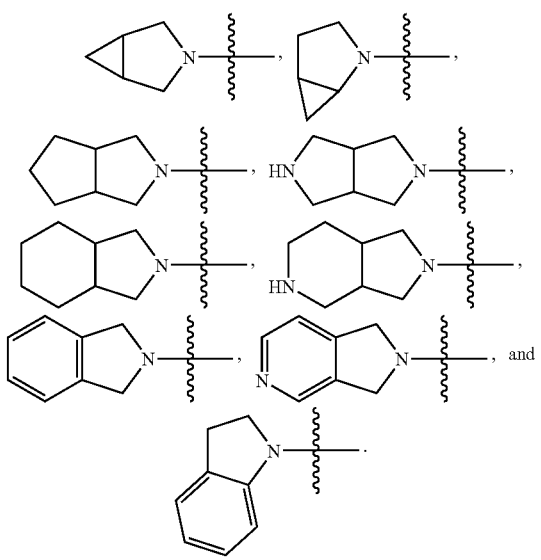

In one embodiment, substituted or unsubstituted pyrrolidinyl described herein is optionally substituted with $R^7$ which is selected from 2-oxo, 2-hydroxy, 2-methyl, 2,5-dioxo, 4-hydroxy-2-oxo, 2-dialkylamino, 2-carboxy, 2-(N,N-dialkyl)carbamoyl, 5-oxo-2-(N,N-dialkyl)carbamoyl, 2-hydroxymethyl, 2-(1-hydroxycyclopropyl), 3-fluoro, 2-methyl-2-carboxy, 3-trifluoromethyl, and 4-trifluoromethyl-2-carboxy.

In another particular embodiment, $Cy^2$ is piperidinyl or piperidinyl fused with a saturated or unsaturated ring structure, wherein Cy is substituted with one or more $R^7$. In one embodiment, Cy is piperidinyl fused with a saturated or unsaturated ring structure having 5 or 6 ring members, wherein the cyclic moiety can contain one or more heteroatoms selected from N, O and S. Non-limiting examples of such fused rings include:

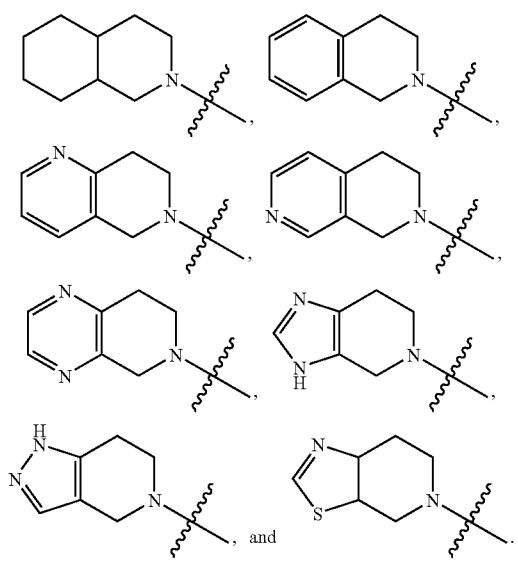

In one embodiment, substituted or unsubstituted piperidinyl described herein is substituted with $R^7$ which is selected from 4-hydroxy-4-methyl, 4-hydroxy-4-trifluoromethyl, 4-hydroxy-4-cyclopropyl, 4-(2,2,2-trifluoroethylamino), 4-(5-oxo-1,4-diazepan-1-yl), 4-acetamido, 4-(1-methylcyclopropylamino), 4-cyano, 4-carboxymethyl, 4-(N,N-dimethylcarbamoyl)methyl, 4-oxo, 4-phenyl, 4-pyridin-3-yl, 4-(5-trifluoromethylpyridin-3-yl), 2-(N,N-dimethylcarbamoyl), 2-aminomethyl, 3-hydroxy, 2-cyclobutyl, 2-carboxy, 4-(1-alkylpiperidin-4-yl), and 3-cyclobutylamino.

In yet another particular embodiment, $Cy^2$ is piperazinyl or piperazinyl fused with a saturated or unsaturated ring structure, wherein Cy is optionally substituted with one or more $R^7$. In one embodiment, Cy is piperazinyl fused with a saturated or unsaturated ring structure having 5 or 6 ring members, wherein the cyclic moiety can contain one or more heteroatoms selected from N, O and S. Non-limiting examples of such fused rings include:

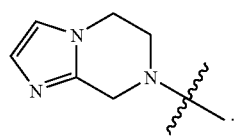

In one embodiment, substituted or unsubstituted piperazinyl described herein is optionally substituted with $R^7$ which is selected from methyl, 1-methylcyclopropyl, trifluoroethyl, methoxypropyl, N,N-dimethylaminopropyl, 1-(carboxy)cyclopropyl, N,N-dimethylcarbamoylcyclopropyl, pyridin-2-ylmethyl, 5-trifluoromethylpyridin-2-ylmethyl, N,N-dimethylcarbamoyl, morpholin-4-ylcarbonyl, t-butylcarbamoyl, morpholinoethoxycarbonyl, benzoyl, picolinoyl, quinoxalin-6-ylcarbonyl, cyclopropylcarbonyl, propionyl, methoxypropanoyl, N,N-dimethylaminopropanoyl, 5-trifluoromethylpyridin-2-yl, 5-chloropyridin-2-yl, 5-cyclopropylpyridin-2-yl, 5-chloropyrimidin-2-yl, 2-methoxyphenyl, 4-carboxyphenyl, 4-(N,N-dimethylcarbamoyl)phenyl, 2-chlorophenyl, 1-methylcyclopropoxycarbonyl, t-butoxycarbonyl, 2-trifluoromethylprop-2-oxycarbonyl, methylsulfonyl, trifluoroethylsulfonyl, 5-trifluoromethylpyridin-3-ylsulfonyl, pyridin-3-ylsulfonyl, phenylsulfonyl, cyclopropylsulfonyl, pyridin-2-yl, 5-trifluoromethylpyridin-2-yl, phenyl, cyclopropyl, ethyl, and

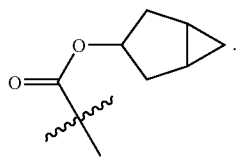

In yet another embodiment, $Cy^2$ is heterocyclyl containing 4, 5 or 6 ring atoms which contain a nitrogen ring atom attached to the remaining molecule and an additional heteroatom, wherein the heterocyclyl is optionally substituted with one or more $R^7$. Non-limiting examples of such heterocyclyls include:

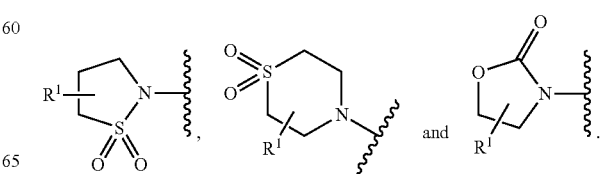

In another embodiment, Cy² is heterocyclyl containing a bridge which connects two carbon ring atoms of the heterocyclyl, wherein the bridge is a direct bond or a divalent chain containing one or more carbons or heteroatoms selected from N, O and S, and wherein the heterocyclyl containing a bridge is optionally substituted with one or more R⁷. Non-limiting examples of such bridged ring moieties include:

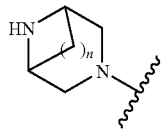

such as, for example,

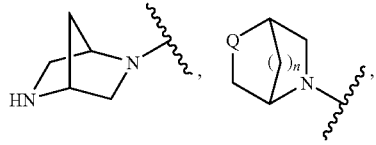

such as, for example,

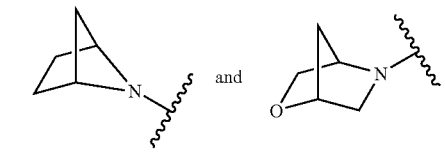

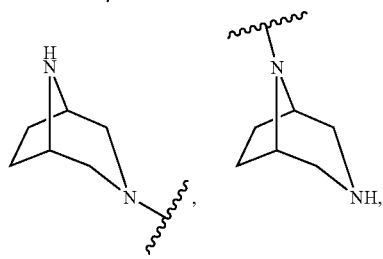

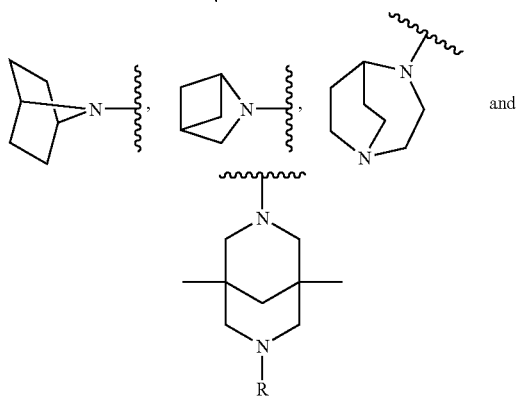

wherein n is 0, 1, 2 or 3; and Q is —NH—, —CH₂—, or —O—.

In various embodiments, a bridged ring as described herein is optionally substituted with one or more R⁸, and non-limiting examples of such substituted bridged rings include:

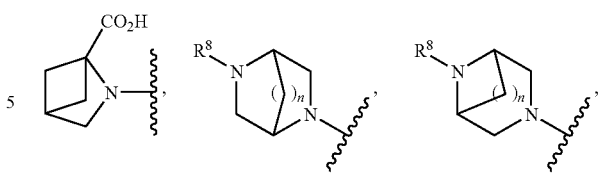

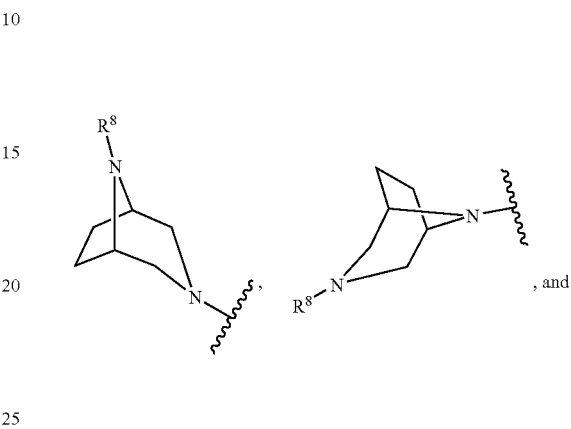

wherein n and R⁸ are as defined above.

In another embodiment, two groups R⁷ are substituted on the same carbon ring atom of Cy² and together with the carbon ring atom of Cy² form a ring situated on Cy² in a spiro configuration, wherein the spiro ring is cycloalkyl or heterocycloalkyl. Non-limiting examples of such spiro rings include:

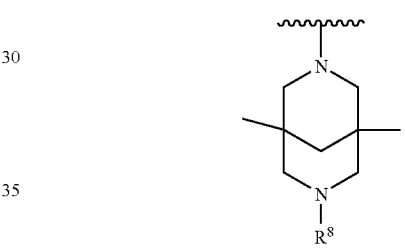

In a particular embodiment of Formula (II), R³, R⁴, R⁵ and R⁶ are as defined above for various aspects of Formula (I); Cy¹ is propylidene; Cy² is 5-membered heterocyclic group such as pyrrolidinyl; q is 0, 1, 2, 3, or 4; and R⁷ is selected from oxo, hydroxy, methyl, hydroxy, dialkylamino, carboxy, (N,N-dialkyl)carbamoyl, hydroxymethyl, hydroxycyclopropyl, fluoro, carboxy, and trifluoromethyl.

Non-limiting examples of such compounds include compounds of Formula (II-d1) and pharmaceutically acceptable salts thereof:

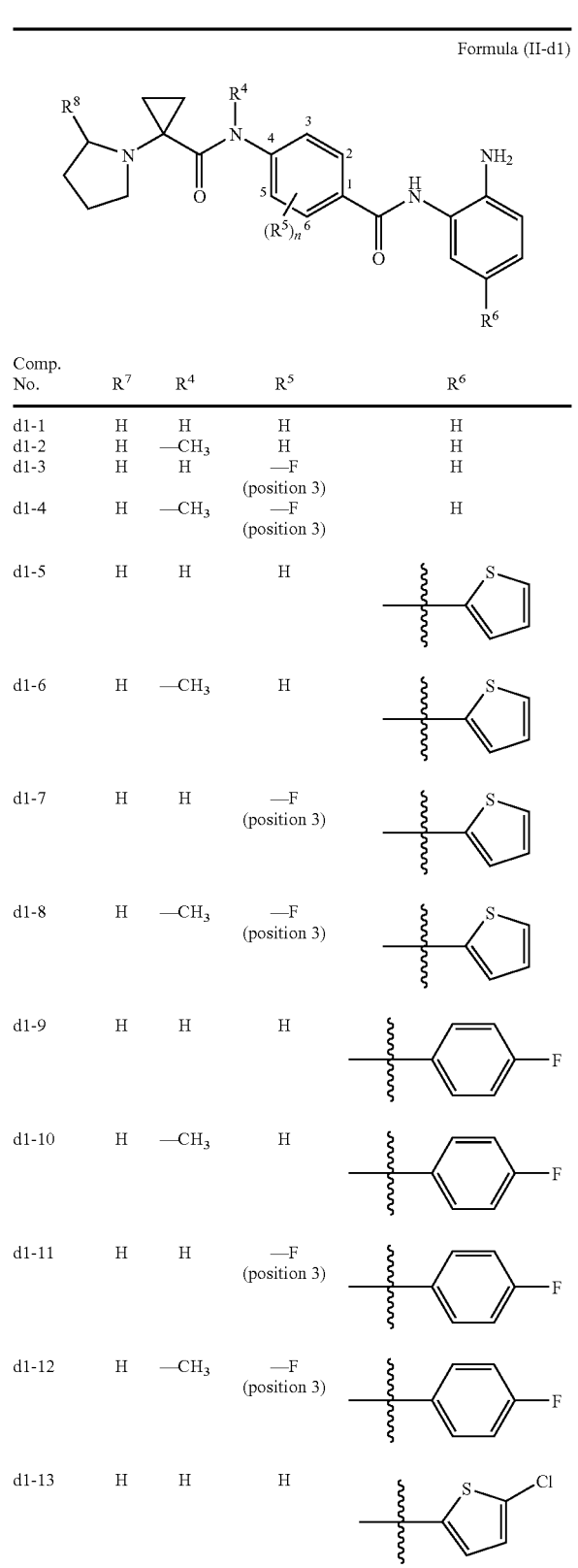

Formula (II-d1)

| Comp. No. | R[7] | R[4] | R[5] | R[6] |
|---|---|---|---|---|
| d1-1 | H | H | H | H |
| d1-2 | H | —CH₃ | H | H |
| d1-3 | H | H | —F (position 3) | H |
| d1-4 | H | —CH₃ | —F (position 3) | H |
| d1-5 | H | H | H | thiophen-2-yl |
| d1-6 | H | —CH₃ | H | thiophen-2-yl |
| d1-7 | H | H | —F (position 3) | thiophen-2-yl |
| d1-8 | H | —CH₃ | —F (position 3) | thiophen-2-yl |
| d1-9 | H | H | H | 4-F-phenyl |
| d1-10 | H | —CH₃ | H | 4-F-phenyl |
| d1-11 | H | H | —F (position 3) | 4-F-phenyl |
| d1-12 | H | —CH₃ | —F (position 3) | 4-F-phenyl |
| d1-13 | H | H | H | 5-Cl-thiophen-2-yl |
| d1-14 | H | —CH₃ | H | 5-Cl-thiophen-2-yl |
| d1-15 | H | H | —F (position 3) | 5-Cl-thiophen-2-yl |
| d1-16 | H | —CH₃ | —F (position 3) | 5-Cl-thiophen-2-yl |
| d1-17 | oxo | H | H | H |
| d1-18 | oxo | —CH₃ | H | H |
| d1-19 | oxo | H | —F (position 3) | H |
| d1-20 | oxo | —CH₃ | —F (position 3) | H |
| d1-21 | oxo | H | H | thiophen-2-yl |
| d1-22 | oxo | —CH₃ | H | thiophen-2-yl |
| d1-23 | oxo | H | —F (position 3) | thiophen-2-yl |
| d1-24 | oxo | —CH₃ | —F (position 3) | thiophen-2-yl |
| d1-25 | oxo | H | H | 4-F-phenyl |
| d1-26 | oxo | —CH₃ | H | 4-F-phenyl |
| d1-27 | oxo | H | —F (position 3) | 4-F-phenyl |
| d1-28 | oxo | —CH₃ | —F (position 3) | 4-F-phenyl |
| d1-29 | oxo | H | H | 5-Cl-thiophen-2-yl |
| d1-30 | oxo | —CH₃ | H | 5-Cl-thiophen-2-yl |

| | | | | |
|---|---|---|---|---|
| d1-31 | oxo | H | —F (position 3) | 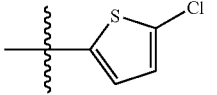 |
| d1-32 | oxo | —CH₃ | —F (position 3) | 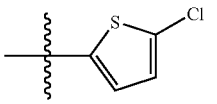 |

In an embodiment of Formula (II), $R^3$, $R^4$, $R^5$ and $R^6$ are as defined above for various aspects of Formula (I); $Cy^1$ is propylidene; $Cy^2$ is 6-membered heterocyclic moiety selected from morpholinyl, piperidinyl and piperazinyl; q is 0, 1, 2, 3 or 4; and $R^8$ is selected from methyl, methylcyclopropyl, trifluoroethyl, methoxypropyl, N,N-dimethylaminopropyl, carboxycyclopropyl, N,N-dimethylcarbamoylcyclopropyl, pyridinylmethyl, trifluoromethylpyridinylmethyl, N,N-dimethylcarbamoyl, morpholineocarbonyl, N-t-butylcarbamoyl, morpholinoethoxycarbonyl, benzoyl, picolinoyl, quinoxalinecarbonyl, cyclopropylcarbonyl, propionyl, methoxypropanoyl, N,N-dimethylaminopropanoyl, trifluoromethylpyridinyl, chloropyridinyl, cyclopropylpyridinyl, chloropyrimidinyl, methoxyphenyl, carboxyphenyl, N,N-dimethylcarbamoylphenyl, chlorophenyl, methylcyclopropoxycarbonyl, t-butoxycarbonyl, trifluoromethylpropoxycarbonyl, methylsulfonyl, trifluoroethylsulfonyl, trifluoromethylpyridinylsulfonyl, pyridinylsulfonyl, phenylsulfonyl, cyclopropylsulfonyl, pyridinyl, trifluoromethylpyridinyl, phenyl, cyclopropyl, hydroxypropyl, hydroxy, trifluoromethyl, hydroxycyclopropyl, trifluoroethylamino, oxo, diazepanyl, acetamido, methylcyclopropylamino, cyano, carboxymethyl, N,N-dimethylcarbamoylmethyl, pyridinyl, trifluoromethylpyridinyl, N,N-dimethylcarbamoyl, aminomethyl, hydroxy, cyclobutyl, carboxy, alkylpiperidinyl, cyclobutylamino, and

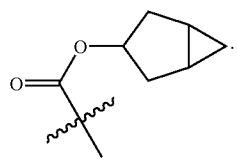

Non-limiting examples of such compounds include compounds of Formula (II-d2) and pharmaceutically acceptable salts thereof:

Formula (II-d2)

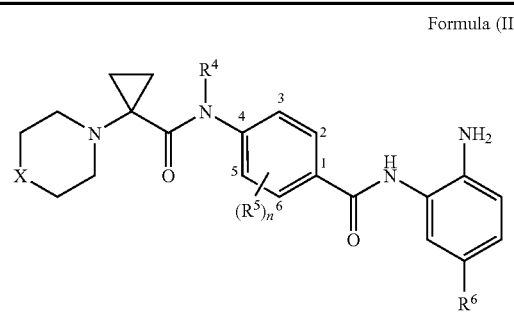

| Comp. No. | X | $R^4$ | $R^5$ | $R^6$ |
|---|---|---|---|---|
| d2-1 | —O— | H | H | H |
| d2-2 | —O— | —CH₃ | H | H |
| d2-3 | —O— | H | —F (position 3) | H |
| d2-4 | —O— | —CH₃ | —F (position 3) | H |
| d2-5 | —O— | H | H | 2-thienyl |
| d2-6 | —O— | —CH₃ | H | 2-thienyl |
| d2-7 | —O— | H | —F (position 3) | 2-thienyl |
| d2-8 | —O— | —CH₃ | —F (position 3) | 2-thienyl |
| d2-9 | —O— | H | H | 4-F-phenyl |
| d2-10 | —O— | —CH₃ | H | 4-F-phenyl |
| d2-11 | —O— | H | —F (position 3) | 4-F-phenyl |
| d2-12 | —O— | —CH₃ | —F (position 3) | 4-F-phenyl |
| d2-13 | —O— | H | H | 5-Cl-2-thienyl |
| d2-14 | —O— | —CH₃ | H | 5-Cl-2-thienyl |
| d2-15 | —O— | H | —F (position 3) | 5-Cl-2-thienyl |
| d2-16 | —O— | —CH₃ | —F (position 3) | 5-Cl-2-thienyl |
| d2-17 | —CH₂— | H | H | H |
| d2-18 | —CH₂— | —CH₃ | H | H |
| d2-19 | —CH₂— | H | —F (position 3) | H |
| d2-20 | —CH₂— | —CH₃ | —F (position | H |

-continued

| | | | | |
|---|---|---|---|---|
| d2-21 | —CH₂— | H | H | 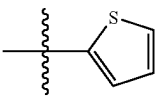 |
| d2-22 | —CH₂— | —CH₃ | H | 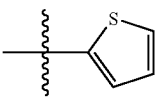 |
| d2-23 | —CH₂— | H | —F (position 3) | 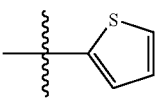 |
| d2-24 | —CH₂— | —CH₃ | —F (position 3) | 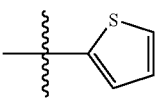 |
| d2-25 | —CH₂— | H | H | 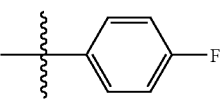 |
| d2-26 | —CH₂— | —CH₃ | H | 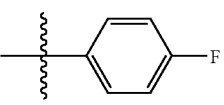 |
| d2-27 | —CH₂— | H | —F (position 3) | 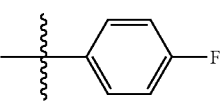 |
| d2-28 | —CH₂— | —CH₃ | —F (position 3) | 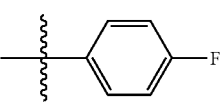 |
| d2-29 | —CH₂— | H | H | 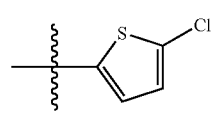 |
| d2-30 | —CH₂— | —CH₃ | H | 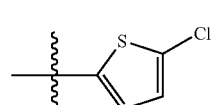 |
| d2-31 | —CH₂— | H | —F (position 3) | 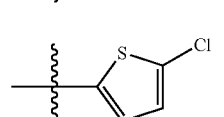 |
| d2-32 | —CH₂— | —CH₃ | —F (position 3) | 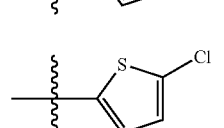 |
| d2-33 | —NH— | H | H | H |
| d2-34 | —NH— | —CH₃ | H | H |
| d2-35 | —NH— | H | —F (position 3) | H |
| d2-36 | —NH— | —CH₃ | —F (position 3) | H |

-continued

| | | | | |
|---|---|---|---|---|
| d2-37 | —NH— | H | H | 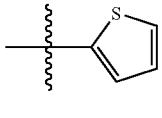 |
| d2-38 | —NH— | —CH₃ | H | 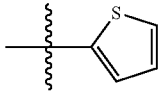 |
| d2-39 | —NH— | H | —F (position 3) | 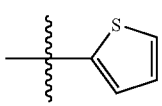 |
| d2-40 | —NH— | —CH₃ | —F (position 3) | 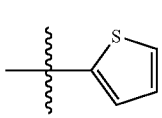 |
| d2-41 | —NH— | H | H | 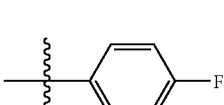 |
| d2-42 | —NH— | —CH₃ | H | 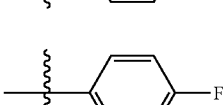 |
| d2-43 | —NH— | H | —F (position 3) | 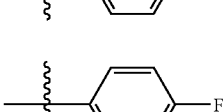 |
| d2-44 | —NH— | —CH₃ | —F (position 3) | 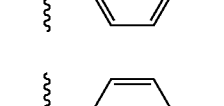 |
| d2-45 | —NH— | H | H | 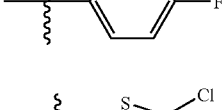 |
| d2-46 | —NH— | —CH₃ | H | 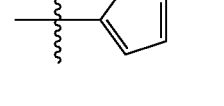 |
| d2-47 | —NH— | H | —F (position 3) | 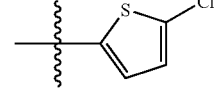 |
| d2-48 | —NH— | —CH₃ | —F (position 3) | 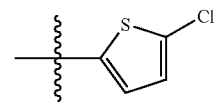 |

In an embodiment of Formula (II), $R^3$, $R^4$, $R^5$, $R^6$ and $R^7$ are as defined above for various aspects of Formula (I); $Cy^1$ is 6-membered heterocyclic group; $Cy^2$ is 5- or 6-membered heterocyclic moiety selected from pyrrolidinyl, morpholinyl, piperidinyl and piperazinyl; q is 0, 1, 2, 3 or 4.

Non-limiting examples of such compounds include compounds of Formulae (II-d3) and (II-d4) and pharmaceutically acceptable salts thereof:

Formula (II-d3)

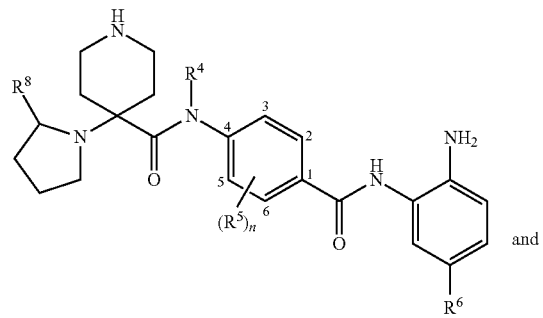

and

Formula (II-d4)

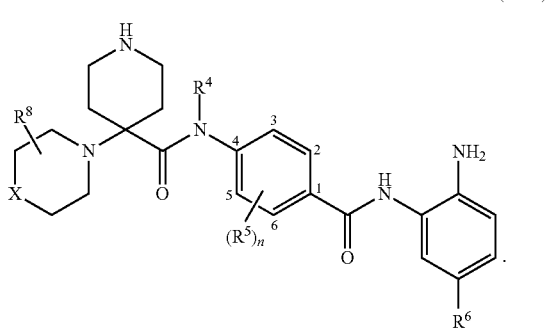

Non-limiting examples of Formulae (II-d3) and (II-d4) include:

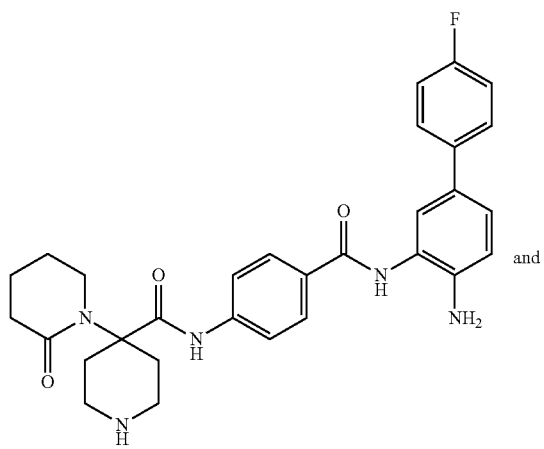

and

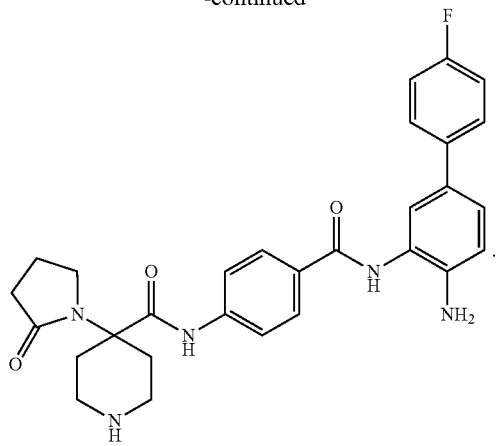

Compound Preparation

A compound of the present invention such as those of Formulae (I), (I-a), (I-b) and (I-c) can be prepared according to the schemes described below, but it shall be appreciated that modifications of the illustrated process or other processes can also be used.

Unless otherwise specified, the starting materials and intermediates of the invention such as compounds 1, 2 and 5 are either commercially available or readily prepared by synthetic modifications of the commercially available compounds, using methods known in the literature to those skilled in the art.

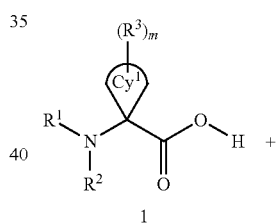

1

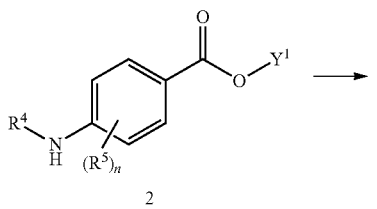

2

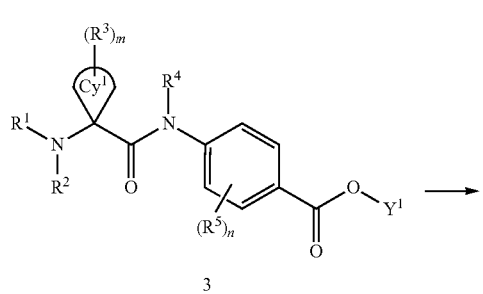

3

-continued

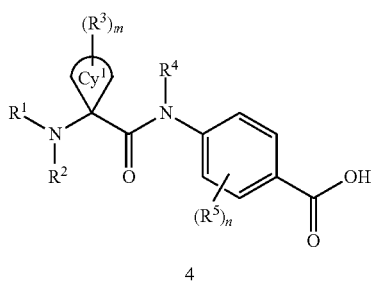

4 wherein $Cy^1$, $R^1$, $R^2$, $R^3$, $R^4$, $R^5$, m, and n are as defined above, and $Y^1$ is alkyl or H.

To Compound 1 dissolved in chloroform ($CHCl_3$) is added N-ethoxycarbonyl-2-ethoxy-1,2-dihydroquinoline (EEDQ), Compound 2, and triethylamine (TEA). The reaction mixture is stirred, diluted with ethyl acetate (EtOAc), washed with aqueous citric acid, water, and brine, and dried over magnesium sulfate ($MgSO_4$). Filtration and concentration yielded Compound 3, which could be used for the next step without further purification.

The $Y^1$ substituent is removed from Compound 3 by base or acid hydrolysis. In some instances, the $Y^1$ substituent is removed by base hydrolysis, wherein Compound 3 is dissolved in a mixture of methanol (MeOH), tetrahydrofuran (THF), and dioxane, stirred with sodium hydroxide (NaOH), diluted with water and diethyl ether, neutralized with hydrochloric acid (HCl), precipitated, filtered, washed with water, and dried. In other instances, the $Y^1$ substituent is removed by acid hydrolysis, wherein Compound 3 is dissolved in dichloromethane (DCM), reacted with trifluoroacetic acid (TFA), stirred, and concentrated. In each instance, Compound 4 is obtained and can be used for the next step without further purification.

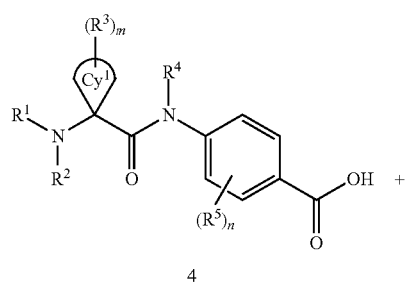

4

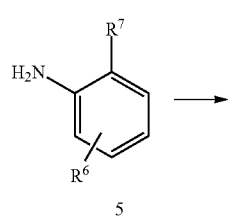

5

-continued

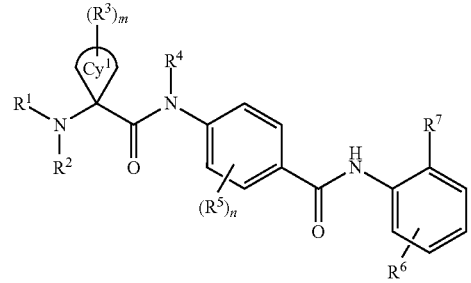

Formula (I)

wherein $R^6$ and $R^7$ are as defined above.

To Compound 4 dissolved in N-methylpyrrolidone (NMP) is added 2-(1H-7-azabenzotriazol-1-yl)-1,1,3,3-tetramethyl uronium hexafluorophosphate (HATU), Compound 5, and N-methylmorpholine (NMM). The reaction mixture is stirred, diluted with water and acetonitrile, directly purified by preparative high pressure liquid chromatography (HPLC), and lyophilized to yield a compound of Formula (I). Determining the suitability of the method (and any necessary routine adaptations) or making a particular intermediate is generally within the skill of those in the art after reading this patent.

The compounds of the present invention inhibit HDAC and are useful to treat or ameliorate diseases mediated directly or indirectly by HDAC. Therefore, another aspect of the present invention is to provide a pharmaceutical composition comprising an effective amount of one or more compounds as described above.

In one embodiment of the invention, a pharmaceutical composition is provided comprising, in addition to one or more compounds described herein, at least one pharmaceutically-acceptable diluent, adjuvant, excipient, or carrier. The composition can take any suitable form for the desired route of administration. Where the composition is to be administered orally, any suitable orally deliverable dosage form can be used, including without limitation tablets, capsules (solid- or liquid-filled), powders, granules, syrups and other liquids, elixirs, inhalants, troches, lozenges, and solutions. Injectable compositions or i.v. infusions are also provided in the form of solutions, suspensions, and emulsions.

A pharmaceutical composition according to the present invention may contain one or more additional therapeutic agents, for example, to increase the efficacy or decrease the side effects. In some embodiments, accordingly, a pharmaceutical composition further contains one or more additional therapeutic agents selected from active ingredients useful to treat or inhibit diseases mediated directly or indirectly by HDAC. Examples of such active ingredients are, without limitation, agents to treat or inhibit cancer, Huntington's disease, cystic fibrosis, liver fibrosis, renal fibrosis, pulmonary fibrosis, skin fibrosis, rheumatoid arthritis, diabetes, stroke, amyotrophic lateral sclerosis, cardiac hypertrophy, heart failure or Alzheimer's disease.

In an embodiment, an additional therapeutic agent to be included is an anti-cancer agent. Examples of an anti-cancer agent include, but are not limited to, alkylating agents such as cyclophosphamide, dacarbazine, and cisplatin; antimetabolites such as methotrexate, mercaptopurine, thioguanine, fluorouracil, and cytarabine; plant alkaloids such as vinblastine, and paclitaxel; antitumor antibiotics such as doxorubicin, bleomycin, and mitomycin; hormones/antihormones such as prednisone, tamoxifen, and flutamide; other types of anticancer agents such as asparaginase, rituximab, trastuzumab, imatinib, retinoic acid and derivatives, colony-stimulating factors, amifostine, camptothecin, topotecan, thalidomide analogs such as lenalidomide, CDK inhibitor and other HDAC inhibitors such as histone deacetylase 1 inhibitors, histone deacetylase 2 inhibitors, histone deacetylase 3 inhibitors, histone deacetylase 4 inhibitors, histone deacetylase 5 inhibitors, histone deacetylase 6 inhibitors, histone deacetylase 7 inhibitors, histone deacetylase 8 inhibitors, histone deacetylase 9 inhibitors, histone deacetylase 10 inhibitors, and histone deacetylase 11 inhibitors.

Yet another aspect of the present invention is to provide a method of inhibiting or treating diseases arising from abnormal cell proliferation and/or differentiation in animal, comprising administering to said animal a therapeutically effective amount of one or more compounds according to the present invention. In one embodiment, the method of inhibiting or treating disease comprises administering to an animal a composition comprising an effective amount of one or more compounds of the invention and a pharmaceutically-acceptable carrier. The composition to be administered may further contain a therapeutic agent such as anti-cancer agent.

A method of the present invention is particularly suitable for use with humans, but may be used with other animals, particularly mammals, such as, for example, non-human primates, companion animals, farm animals, laboratory animals, and wild and zoo animals.

A method of the present invention is particularly useful to treat diseases mediated directly or indirectly by HDAC since the compounds of the present invention have inhibitory activity against those molecules. In some embodiments, therefore, a method of the present invention is used in inhibiting or treating HDAC-mediated diseases. Examples of such disease include, but are not limited to, cell proliferative diseases such as cancer, autosomal dominant disorders such as Huntington's disease, genetic related metabolic disorder such as cystic fibrosis, fibrosis such as liver fibrosis, renal fibrosis, pulmonary fibrosis and skin fibrosis, autoimmune diseases such as rheumatoid arthritis, diabetes, acute and chronic neurological diseases such as stroke, hypertrophy such as cardiac hypertrophy, heart failure including congestive heart failure, amyotrophic lateral sclerosis, and Alzheimer's disease.

In an embodiment, a method according to the present invention is applied to a patient with cancer, cystic fibrosis, or pulmonary fibrosis. In some embodiments, a method using a compound according to the present invention is used to treat or inhibit a cancer selected from bladder cancer, breast cancer, colon and rectal cancer, endometrial cancer, kidney (renal cell) cancer, leukemia, lung cancer, melanoma, non-Hodgkin's lymphoma, pancreatic cancer, prostate cancer, skin cancer (non-melanoma), and thyroid cancer.

EXAMPLES

The following examples are merely illustrative, and do not limit this disclosure in any way.

Example 1 tert-Butyl-1-((4-((2-aminophenyl)carbamoyl)phenyl)carbamoyl)cyclohexyl carbamate

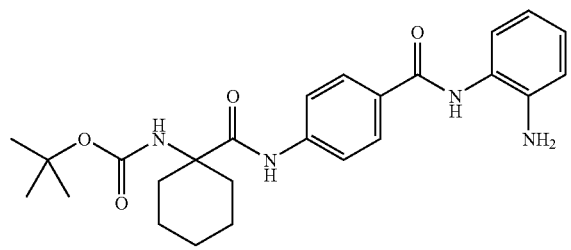

To 1-(tert-butoxycarbonylamino)cyclohexanecarboxylic acid (516 mg, 2.12 mmol) in chloroform (10 mL), was added EEDQ (629 mg, 2.54 mmol), 4-amino-benzoic acid methyl ester (320 mg, 2.12 mmol) and TEA (0.4 mL, 3.18 mmol) and stirred at 70° C. for 16 hours. The reaction mixture was diluted with ethyl acetate (100 mL), washed twice with 10% aq. citric acid, twice 1 N NaOH, water and brine, and dried over magnesium sulfate, filtered and concentrated to give the ester, which was used for the next step without purification.

To the above ester (2.1 mmol) in methanol/tetrahydrofuran/dioxane (6:2:5, 13 mL) was added 1 N NaOH (10 mL, 10 mmol) and stirred at room temperature. After 12 hours, the reaction mixture was concentrated, diluted with water and washed twice with diethyl ether. The aqueous phase was then neutralized with 1 N HCl (10 mmol) and the precipitated solid was filtered, washed with water and dried to give the acid which was used for the next step without purification.

To the above acid (100 mg, 0.27 mmol) in NMP (3 mL) was added HATU (157 mg, 0.41 mmol), 1,2-phenylenediamine (60 mg, 0.54 mmol), and NMM (0.1 mL, 0.83 mmol). The reaction mixture was stirred for room temperature for 48 hours. The reaction mixture was then diluted with water and acetonitrile, directly purified by preparative HPLC, and lyophilized to give the title compound. $C_{25}H_{32}N_4O_4$ 453.2 (M+1). $^1$H-NMR (400 MHz, DMSO-$d_6$): δ 9.55 (s, 1H); 9.50 (s, 1H); 7.90 (d, J=8.4 Hz, 2H); 7.69 (d, J=8.4 Hz, 2H); 7.13 (d, J=7.6 Hz, 1H); 6.94 (t, J=7.2 Hz, 1H); 6.75 (d, J=6.8 Hz, 1H); 6.58 (t, J=8 Hz, 1H); 4.83 (brs 1H); 2.13-1.74 (m, 7H); 1.49-1.22 (m, 14H).

Example 2 tert-Butyl-1-((4-((2-aminophenyl)carbamoyl)phenyl)carbamoyl)cyclopropyl carbamate

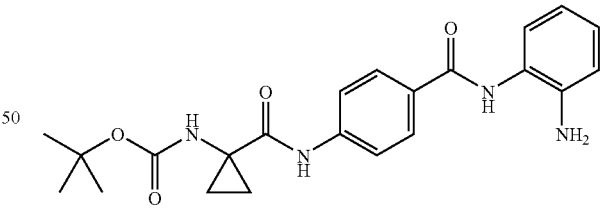

Similar procedure from Example 1 was followed to obtain the title compound using 1-(tert-butoxycarbonylamino)cyclopropanecarboxylic. $C_{22}H_{26}N_4O_4$ 411.2 (M+1). $^1$H-NMR (400 MHz, DMSO-$d_6$): δ 9.61 (s, 1H); 9.49 (s, 1H); 7.88 (d, J=8.8 Hz, 2H); 7.70 (d, J=8.8 Hz, 2H); 7.31 (brs, 1H); 7.10 (d, J=7.6 Hz, 1H); 6.91 (t, J=7.2 Hz, 1H); 6.72 (d, J=6.8 Hz, 1H); 6.54 (t, J=8 Hz, 1H); 4.83 (brs 2H); 1.34-0.1308 (m, 11H); 0.97 (m, 2H).

Example 3 tert-Butyl-1-((4-((2-aminophenyl)carbamoyl)phenyl)carbamoyl)cyclopentylcarbamate

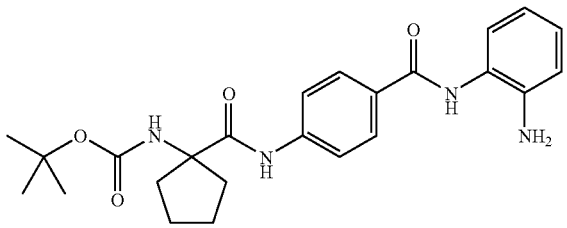

Similar procedure from Example 1 was followed to obtain the title compound using 1-(tert-butoxycarbonylamino)cyclopentanecarboxylic acid. $C_{24}H_{30}N_4O_4$ 439.2 (M+1). $^1$H-NMR (400 MHz, DMSO-$d_6$): δ 9.58 (s, 1H); 9.47 (s, 1H); 7.86 (d, J=8.8 Hz, 2H); 7.67 (d, J=8.8 Hz, 2H); 7.09 (d, J=7.6 Hz, 1H); 6.99 (brs, 1H); 6.91 (t, J=7.2 Hz, 1H); 6.72 (d, J=8 Hz, 1H); 6.54 (t, J=8 Hz, 1H); 4.80 (brs, 2H); 2.07 (m, 2H); 1.79-1.55 (m, 6H); 1.30 (s, 9H).

Example 4

Benzyl-1-((4-((2-aminophenyl)carbamoyl)phenyl)carbamoyl)cyclopropyl carbamate

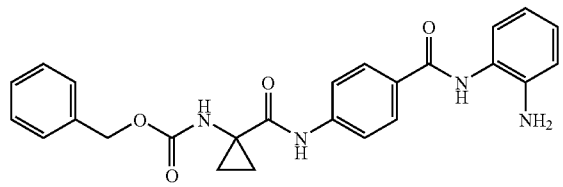

To the 1-(benzyloxycarbonylamino)cyclopropanecarboxylic acid (500 mg, 2.12 mmol) in CHCl$_3$ (8 mL) was added EEDQ (629 mg, 2.54 mmol), tert-butyl 4-aminobenzoate (411 mg, 2.12 mmol) and TEA (0.4 mL, 3.18 mmol). The reaction mixture was stirred at 70° C. for 16 hours and diluted with ethyl acetate (100 mL), washed twice with 10% aq. citric acid, twice with 1 N NaOH with water, and with brine, dried over magnesium sulfate, filtered and concentrated to give the ester which was used for the next step without purification.

To the above ester (2.1 mmol) in DCM (12 mL) was added TFA (1.6 mL) and stirred at room temperature. After 12 hours, the reaction mixture was concentrated, and used for the next step without purification.

To the above acid (50 mg, 0.14 mmol) in NMP (2 mL) was added HATU (80 mg, 0.41 mmol), 1,2-phenylenediamine (31 mg, 0.28 mmol) and NMM (0.05 mL, 0.42 mmol). The reaction mixture was stirred for room temperature for 60 hours, diluted with water and acetonitrile directly purified by preparative HPLC, and lyophilized to give the title compound. $C_{25}H_{24}N_4O_4$ 445.1 (M+1). $^1$H-NMR (400 MHz, DMSO-$d_6$): δ 9.76 (s, 1H); 9.54 (s, 1H); 7.92 (d, J=8.8 Hz, 2H); 7.75 (d, J=8.8 Hz, 2H); 7.36-7.29 (m, 5H); 7.13 (d, J=7.2 Hz, 1H); 6.95 (t, J=7.2 Hz, 1H); 6.76 (d, J=8 Hz, 1H); 6.54 (t, J=8 Hz, 1H); 5.05 (s, 2H); 1.14 (m, 2H); 1.04 (m, 2H).

Example 5

Benzyl-1-((4-((2-amino-5-(thiophen-2-yl)phenyl)carbamoyl)phenyl)carbamoyl)cyclopropyl carbamate

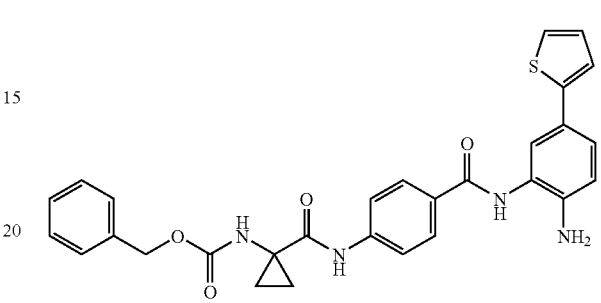

Similar procedure from Example 4 was followed to obtain the title compound using (2-amino-4-thiophen-2-yl-phenyl)-carbamic acid tert-butyl ester. $C_{29}H_{26}N_4O_4S$ 527.1 (M+1). $^1$H NMR (400 MHz, DMSO-$d_6$): δ 9.74 (s, 1H); 9.60 (s, 1H); 7.92 (d, J=8.8 Hz, 2H); 7.73 (d, J=8.8 Hz, 2H); 7.40-7.17 (m, 8H); 6.92 (m, 1H); 6.75 (d, J=8.0 Hz, 1H); 5.05 (brs, 2H); 5.02 (s, 2H); 1.36 (m, 2H); 1.01 (m, 2H).

Example 6

Benzyl-1-((4-((2-amino-5-(4-fluorophenyl)phenyl)carbamoyl)phenyl)carbamoyl)cyclopropyl carbamate

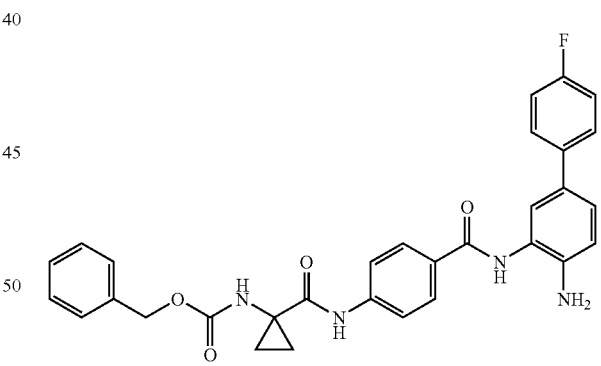

Similar procedure from Example 4 was followed to obtain the title compound using (3-amino-4'-fluoro-biphenyl-4-yl)carbamic acid tert-butyl ester. $C_{31}H_{27}N_4O_4F$ 539.1 (M+1). $^1$H-NMR (400 MHz, DMSO-$d_6$): δ 9.74 (s, 1H); 9.60 (s, 1H); 7.92 (d, J=8.8 Hz, 2H); 7.73 (d, J=8.8 Hz, 2H); 7.53-7.14 (m, 10H); 6.80 (d, J=8.4 Hz, 1H); 5.05 (brs, 2H); 5.02 (s, 2H); 1.36 (m, 2H); 1.01 (m, 2H).

Example 7

Benzyl-1-((4-((2-amino-5-(5-chlorothiophen-2-yl)phenyl)carbamoyl)phenyl)carbamoyl)cyclopropylcarbamate

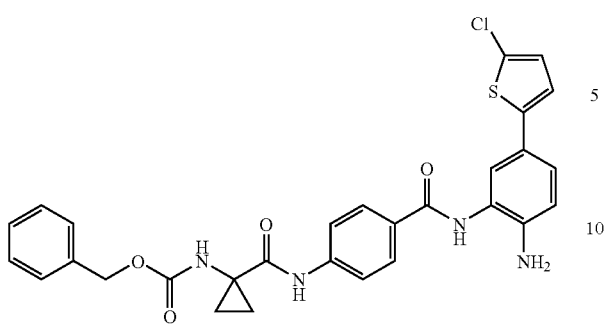

Similar procedure from Example 4 was followed to obtain the title compound using 2-amino-4-(5-chloro-thiophen-2-yl)-phenyl]-carbamic acid tert-butyl ester. $C_{29}H_{25}N_4O_4SCl$ 560.7 (M+1). $^1$H-NMR (400 MHz, DMSO-$d_6$): δ 9.76 (s, 1H); 9.61 (s, 1H); 7.94 (d, J=8.8 Hz, 2H); 7.76 (d, J=8.8 Hz, 2H); 7.380-7.02 (m, 9H); 6.78 (d, J=8.8 Hz, 1H); 5.19 (s, 2H); 5.05 (s, 2H); 1.41 (m, 2H); 1.04 (m, 2H).

Example 8

Benzyl-1-((4-((2-amino-5-(thiophen-2-yl)phenyl)carbamoyl)-2-fluorophenyl)carbamoyl)cyclopropyl-carbamate 7.81 (m, 3H); 7.43-7.21 (m, 8H); 7.02 (m, 1H); 6.79 (d, J=8.4 Hz, 1H); 5.2 (brs, 1H); 5.07 (s, 2H); 1.40 (m, 2H); 1.08 (m, 2H).

Example 9

Benzyl-1-((4-((2-amino-5-(4-Fluorophenyl)phenyl)carbamoyl)phenyl)(methyl)carbamoyl)cyclopropyl-carbamate

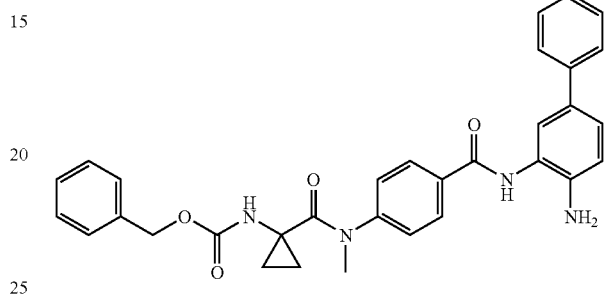

Similar procedure from Example 4 was followed to obtain the title compound using methyl-4-(methylamino)benzoate and (3-amino-4'-fluoro-biphenyl-4-yl)carbamic acid tert-butyl ester. $C_{32}H_{29}N_4O_4F$ 552.8 (M+1). $^1$H NMR (400 MHz, DMSO-$d_6$): δ 9.74 (s, 1H); 8.02 (d, J=8.8 Hz, 2H); 7.55-7.17 (m, 13H); 6.94-6.84 (m, 2H); 5.03 (brs, 2H); 4.83 (s, 2H); 3.16 (s, 3H); 1.41 (m, 2H); 0.81 (m, 2H).

Example 10

N-(4-Amino-4'-fluorobiphenyl-3-yl)-4-(1-aminocyclopropanecarboxamido)benzamide

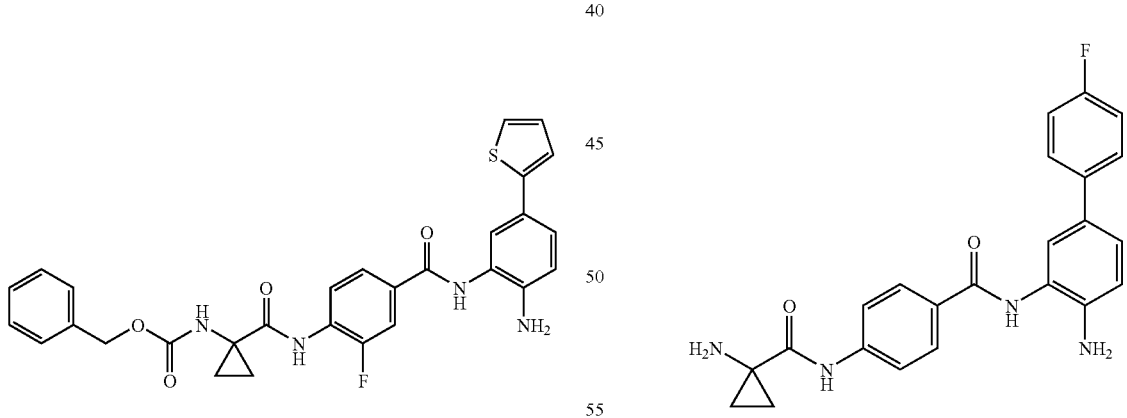

Similar procedure from Example 4 was followed to obtain the title compound using ethyl-4-amino-3-fluorobenzoate and (2-amino-4-thiophen-2-yl-phenyl)carbamic acid tert-butyl ester. $C_{29}H_{26}N_4O_4SF$ 544.8 (M+1). $^1$H-NMR (400 MHz, DMSO-$d_6$): δ 9.73 (s, 1H); 9.39 (s, 1H); 8.1 (9s, 1H); 7.89-

To 1-(tert-butoxycarbonylamino)cyclopropanecarboxylic acid (955 mg, 4.74 mmol) in DMF (12 mL), was added HATU (2.2 g, 5.7 mmol), 4-amino-benzoic acid ethyl ester (861 mgs, 5.22 mmol) and NMM (1.6 mL, 14.22 mmol) and stirred at 50° C. for 16 hours. The reaction mixture was diluted with ethylacetate (100 mL), washed twice with 1 N HCl, twice with 1 N NaOH, once each with water and brine, and dried over MgSO$_4$. Filtration and concentration gave the ester which was used for the next step.

To the above ester (1.62 g, 4.65 mmol) in ethanol/THF (2:1, 15 mL) was added 1 N NaOH (10 mL, 10 mmol) and stirred at room temperature. After 16 hours, the reaction mixture was concentrated, diluted with water and washed twice with ether. The aqueous phase was then neutralized with 6 N HCl and extracted thrice with ethyl acetate. The combined organic layers were washed with brine and dried over MgSO$_4$. Filtered and concentrated to give the acid which was used for the next step with out purification.

To the above acid (320 mg, 1.0 mmol) in DMF (3 mL), was added HATU (570 mg, 1.52 mmol), (3-amino-4'-fluoro-biphenyl-4-yl)-carbamic acid tert-butyl ester (302 mg, 1.0 mmol) and NMM (0.22 mL, 2.0 mmol) and stirred at 50° C. for 18 hours. The reaction mixture was then diluted with water and acetonitrile and the resulting solid was filtered and washed with water and dried to give (3-{4-[(1-tert-butoxycarbonylamino-cyclopropanecarbonyl)-amino]-benzoylamino}-4'-fluoro-biphenyl-4-yl)carbamic acid tert-butyl ester. To the above bis-BOC protected compound, 4.0 M HCl dioxane (5 mL) was added and stirred at room temperature for 1 hour. The reaction mixture was then diluted with ether and stirred. The resulting solid was filtered, washed with ether, and dried to give the title compound. C$_{23}$H$_{21}$N$_4$O$_2$F 404.84 (M+1). $^1$H-NMR (400 MHz, DMSO-d$_6$): δ 10.38 (s, 1H); 9.99 (s, 1H); 8.91 (brs, 3H); 8.10 (d, J=8.8 Hz, 2H); 7.82 (d, J=8.8 Hz, 2H); 7.76 (s, 1H); 7.66 (m, 2H); 7.51-7.24 (m, 4H); 1.66 (M, 2H); 1.40 (m, 2H).

Example 11

N-(4-amino-4'-fluorobiphenyl-3-yl)-4-(1-(3-tert-butylureido)cyclopropanecarboxamido)benzamide

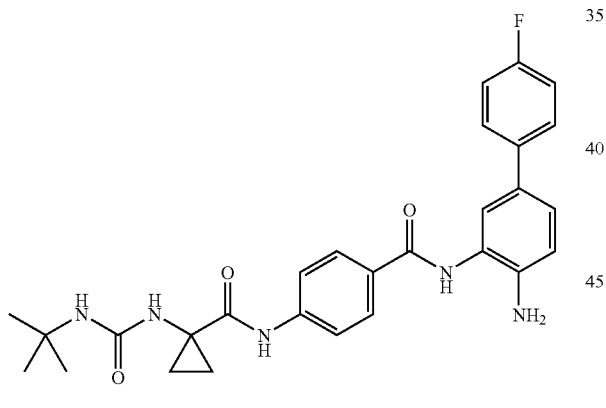

To 1-(benzyloxycarbonylamino)cyclopropanecarboxylic acid (500 mg, 2.12 mmol) in CHCl$_3$ (8 mL), was added EEDQ (629 mg, 2.54 mmol), tert-butyl 4-aminobenzoate (411 mg, 2.12 mmol) and TEA (0.4 mL, 3.18 mmol) and stirred at 70° C. for 16 hours. The reaction mixture was diluted with ethyl acetate (100 mL), washed twice with 10% aq. citric acid, twice with 1 N NaOH, once each with water and brine, and dried over MgSO$_4$. Filtration and concentration gave the ester which was used for the next step without purification.

To the above ester in DCM was added TFA and stirred at room temperature. After 12 hours, the reaction mixture was concentrated, and used for the next step with out purification. To the above acid in DMF was added HATU, 3-amino-4'-fluoro-biphenyl-4-ylcarbamic acid tert-butyl ester and NMM. The reaction mixture war stirred at 50° C. for 16 hours and diluted with water and acetonitrile. The resulting solid was filtered, washed with water, and dried to give (3-{4-[(1-benzyloxycarbonylamino-cyclopropanecarbonyl)-amino]-benzoylamino}-4'-fluoro-biphenyl-4-yl)carbamic acid tert-butyl ester.

To a solution of 3-{4-[(1-benzyloxycarbonylamino-cyclopropanecarbonyl)-amino]-benzoylamino}-4'-fluoro-biphenyl-4-yl)carbamic acid tert-butyl ester (200 mg, 0.313 mmol) in ethyl acetate (3 mL) was added 1,4-cyclohexadiene (0.35 mL) and 10% Pd on carbon (40 mg). The reaction mixture was heated by microwave (Biotage) at 100° C. for 30 minutes, diluted with ethyl acetate, filtered, and concentrated to give (3-{4-[(1-amino-cyclopropanecarbonyl)-amino]-benzoylamino}-4'-fluorobiphenyl-4-yl)carbamic acid tert-butyl ester, which was used further without purification.

The above crude compound was dissolved in DCM (4 mL), treated subsequently with triethylamine (0.06 mL, 0.46 mmol) and tert-butylisocyanate (0.04 mL, 0.34 mmol), and stirred at room temperature for 16 hours. The reaction mixture was then concentrated, treated with 4.0 M HCl in dioxane (8 mL), stirred at room temperature for 1 hour. The reaction mixture was concentrated again, diluted with water and acetonitrile, directly purified by preparative HPLC, and lyophilized to give the title compound. C$_{28}$H$_{30}$N$_5$O$_3$F 503.9 (M+1). $^1$H-NMR (400 MHz, DMSO-d$_6$): δ 9.72 (s, 1H); 9.60 (s, 1H); 7.95 (d, J=8.4 Hz, 2H); 7.70 (d, J=8.4 Hz, 2H); 7.56 (m, 2H); 7.45 (s, 1H); 7.27-7.15 (m, 3H); 6.83 (d, J=8.4 Hz, 1H); 6.41 (s, 1H); 5.05 (brs, 2H); 1.34 (m, 2H); 1.22 (s, 9H); 0.89 (m, 2H).

Example 12

N-(4-(4-amino-4'-fluorobiphenyl-3-ylcarbamoyl) phenyl)-4-(2-oxopyrrolidin-1-yl)piperidine-4-carboxamide

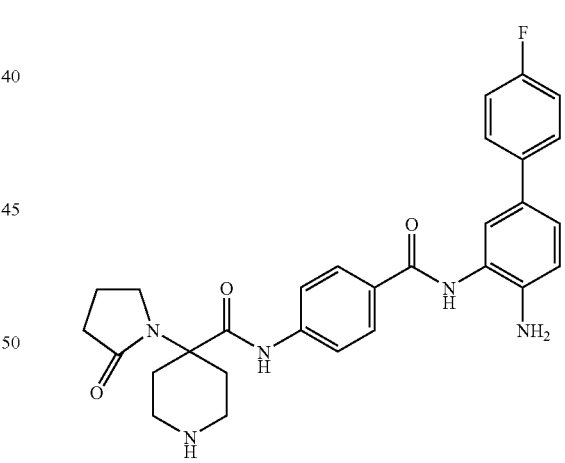

To a solution of methyl 4-amino-1-BOC-piperidine-4-carboxylate (2.0 g, 6.78 mmol) in DCM (15 mL) and pyridine (2.10 mL, 20.35 mmol), 4-chlorobutyryl chloride (0.84 mL, 7.5 mmol) in DCM (5 mL) was added slowly at 0° C. The reaction mixture was gradually warmed to room temperature and stirred for 16 hours. The reaction mixture was diluted with DCM (40 mL), and quenched with saturated NaHCO$_3$ (30 mL). The organic layer was separated and the aqueous layer was extracted twice with DCM. The combined organic layers were then washed with saturated aqueous NaHCO$_3$ and brine, dried over MgSO$_4$, filtered and concentrated to give 4-(4-chloro-butyrylamino)-piperidine-1,4-dicarboxylic acid 1-tert-butyl ester 4-methyl ester which was used further without purification.

The ester compound in dry THF (15 mL) was added to a suspension of NaH (352 mgs, 8.81 mmol) in dry THF (3 mL) and stirred at room temperature for 16 hours. The reaction mixture was then quenched with water (4 mL), diluted with ethyl acetate (60 mL), dried over MgSO$_4$, filtered, and purified by flash chromatography on silica gel with stepwise elution using 50% ethyl acetate/hexanes to 100% ethyl acetate/hexanes gave 4-(2-oxo-pyrrolidin-1-yl)-piperidine-1,4-dicarboxylic acid 1-tert-butyl ester 4-methyl ester (1.28 g, 58.0% yield).

To the ester (1.28 g, 3.92 mmol) in methanol (12 mL) was added 3 N NaOH (10 mL, 31.3 mmol) and stirred at room temperature. After 12 hours, the reaction mixture was concentrated, diluted with water and neutralized with 6 N HCl. The precipitate was filtered, washed with water and dried to give an acid which was used for the next step with out purification.

To the above acid (312 mg, 1.0 mmol) in DMF (2 mL), was added HATU (570 mg, 1.52 mmol), 3-(4-amino-benzoylamino)-4'-fluoro-biphenyl-4-ylcarbamic acid tert-butyl ester (421 mg, 1.00 mmol) and NMM (0.33 mL, 3.0 mmol) and stirred at 50° C. for 18 hours. The reaction mixture was then diluted with water and acetonitrile and the precipitate was filtered, washed with water and dried. The solid was then purified by column chromatography on silica gel with elution using 80% ethyl acetate/hexanes to give 4-[4-(4-tert-butoxycarbonylamino-4'-fluoro-biphenyl-3-ylcarbamoyl)-phenylcarbamoyl]-4-(2-oxo-pyrrolidin-1-yl)-piperidine-1-carboxylic acid tert-butyl ester.

To the above bis-BOC protected compound, 4.0 M HCl dioxane (10 mL) was added and stirred at room temperature for 1 hour. The reaction mixture was then diluted with ether and stirred. The resulting solid was filtered, washed with ether, and dried to give the title compound. $C_{29}H_{30}N_5O_3F$ 515.8 (M+1). $^1$H-NMR (400 MHz, DMSO-d$_6$): δ 10.12 (brs, 1H); 9.83 (s, 1H); 8.88 (brs, 2H); 8.02 (d, J=8.4 Hz, 2H); 7.73 (d, J=8.4 Hz, 2H); 7.64-7.61 (m, 3H); 7.45 (d, J=8.4 Hz, 1H); 7.26 (m, 3H); 3.53 (m, 2H); 3.51-3.10 (m, 4H); 2.39-1.99 (m, 6H).

Example 13

N-(4-(2-aminophenylcarbamoyl)phenyl)-4-(2-oxopyrrolidin-1-yl)piperidine-4-carboxamide

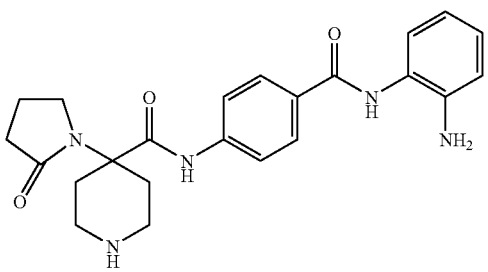

Similar procedure from Example 12 was followed to obtain the title compound using N-Boc-1,2-phenylenediamine instead of 3-(4-amino-benzoylamino)-4'-fluoro-biphenyl-4-ylcarbamic acid tert-butyl ester. $C_{23}H_{27}N_5O_3$ 422.0 (M+1). $^1$H-NMR (400 MHz, DMSO-d$_6$): δ 10.28 (s, 1H); 9.88 (s, 1H); 9.01 (brs, 1H); 8.89 (brs, 1H); 8.03 (d, J=8.8 Hz, 2H); 7.74 (d, J=8.8 Hz, 2H); 7.47-7.24 (m, 4H); 3.69 (m, 2H); 3.51-2.46 (m, 4H); 2.36-2.24 (m, 2H); 2.22-2.15 (m, 4H); 2.04-1.95 (m, 2H).

Example 14

N-(2-amino-5-(thiophen-3-yl)phenyl)-4-(1-aminocyclopropane carboxamido)benzamide

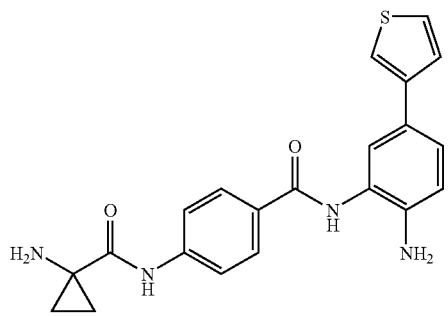

To the 1-(tert-butoxycarbonylamino)cyclopropanecarboxylic acid (955 mg, 4.74 mmol) in DMF (12 mL), was added HATU (2.2 g, 5.7 mmol), 4-Amino-benzoic acid ethyl ester (861 mgs, 5.22 mmol) and NMM (1.6 mL, 14.22 mmol) and stirred at 50° C. for 16 h. The reaction mixture was diluted with EtOAc (100 mL), washed with 1N HCl (2×), 1N NaOH (2×), water, brine and dried (MgSO$_4$). Filtration and concentration gave the ester which was used for the next step.

To the above ester (1.62 g, 4.65 mmol) in EteOH/THF (2:1, 15 mL) was added 1 N NaOH (10 mL, 10 mmol) and stirred at room temperature. After 16 h, the reaction mixture was concentrated, diluted with water and washed with ether (2×). The aqueous phase was then neutralized with 6N HCl and extracted with EtOAc (3×). The combined organic layers were washed with brine and dried (MgSO$_4$). Filtered and concentrated to give the acid which was used for the next step with out purification.

To the above acid (480 mg, 1.5 mmol) in DMF (3 mL), was added HATU (855 mg, 2.25 mmol), [2-Amino-4-(4,4,5,5-tetramethyl-[1,3,2]dioxaborolan-2-yl)-phenyl]-carbamic acid tert-butyl ester (500 mg, 1.5 mmol) and NMM (0.33 mL, 3.0 mmol) and stirred at 50° C. for 50 hours. The reaction mixture was then diluted with water and acetonitrile and the precipitate was filtered, washed with water and dried. The solid was then purified by column chromatography on silica gel with elution using 60% ethyl acetate/hexanes to give [2-{4-[(1-tert-Butoxycarbonylamino-cyclopropanecarbonyl)-amino]-benzoylamino}-4-(4,4,5,5-tetramethyl-[1,3,2]dioxaborolan-2-yl)-phenyl]-carbamic acid tert-butyl ester.

To the above boronate (288 mgs, 0.45 mmol), 3-bromothiophene (74 mgs, 0.45 mmol), PdCl$_2$(dppf) (66 mgs, 0.09 mmol), K$_2$CO$_3$ (125 mgs, 0.91 mmol) in toluene/EtOH/Water (2:1:1, 4 mL) was heated in microwave (Emry's Optimizer) at 110° C. After 20 min, the reaction mixture was concentrated and purified by column chromatography on silica gel with elution using 70% ethyl acetate/hexanes to give (2-{4-[(1-tert-Butoxycarbonylamino-cyclopropanecarbonyl)-amino]-benzoylamino}-4-thiophen-3-yl-phenyl)-carbamic acid tert-butyl ester.

To the above bis-BOC protected compound, 4.0 M HCl dioxane (6 mL) was added and stirred at room temperature for 1 hour. The reaction mixture was then diluted with water and acetonitrile and directly purified by preparative HPLC affording the title compound as tan solid, after lyophilization. $C_{21}H_{20}N_4O_2S$ 392.8 (M+1). $^1$H NMR (400 MHz, DMSO-$d_6$): δ 9.61 (s, 1H); 7.95 (d, J=8.8 Hz, 2H); 7.79 (d, J=8.8 Hz, 2H); 7.53-7.30 (m, 5H); 6.78 (d, J=8.4 Hz, 1H); 4.97 (s, 2H); 1.19 (m, 2H); 0.89 (m, 2H).

Example 15

N-(4-amino-4'-fluorobiphenyl-3-yl)-4-(1-(2-oxopyrrolidin-1-yl)cyclobutanecarboxamido)benzamide

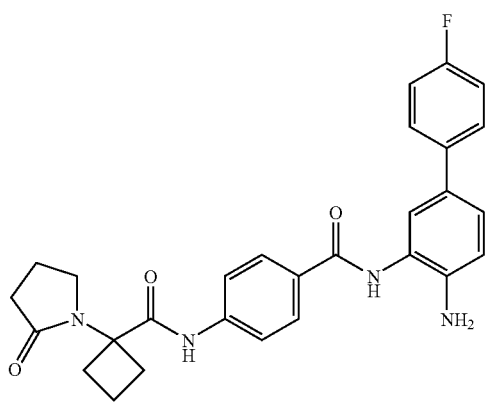

Similar procedure from Example 12 was followed to obtain the title compound using Ethyl 1-amino-1-cyclobutanecarboxylate monohydrochloride instead of methyl 4-amino-1-BOC-piperidine-4-carboxylate. $C_{28}H_{27}FN_4O_3$ 486.9 (M+1). $^1$H-NMR (400 MHz, DMSO-$d_6$): δ 9.64 (s, 1H); 9.48 (s, 1H); 7.96 (d, J=8.4 Hz, 2H); 7.70 (d, J=8.4 Hz, 2H); 7.56-7.45 (m, 3H); 7.27-7.17 (m, 3H); 6.84 (d, J=8.4 Hz, 1H); 5.04 (brs, 2H); 3.54 (m, 2H); 2.60-2.57 (m, 2H); 2.41-2.33 (m, 2H); 2.27 (m, 2H); 2.02-1.96 (m, 2H); 1.84-1.78 (m, 2H).

Example 16

N-(4-amino-4'-fluorobiphenyl-3-yl)-4-(1-aminocyclobutanecarboxamido)benzamide

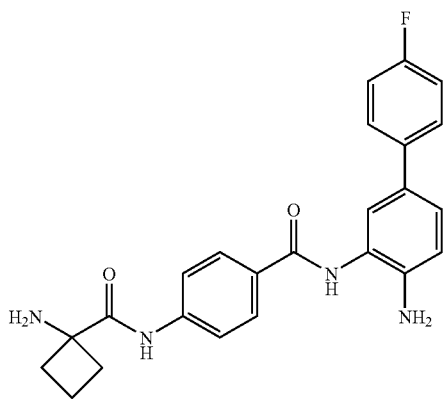

Similar procedure from Example 10 was followed to obtain the title compound using 1-tert-butoxycarbonylamino-cyclobutanecarboxylic acid and (3-amino-4'-fluoro-biphenyl-4-yl)carbamic acid tert-butyl ester. $C_{24}H_{23}N_4O_2F$ 418.8 (M+1). $^1$H NMR (400 MHz, DMSO-$d_6$); δ 10.74 (brs, 1H); 10.24 (brs, 1H); 8.87 (brs, 2H); 8.09 (d, J=8.4 Hz, 2H); 7.88 (d, J=8.4 Hz, 2H); 7.88-7.62 (m, 3H); 7.48-7.47 (m, 1H); 7.27 (m, 3H); 2.82-2.75 (m, 2H); 2.31-1.95 (m, 4H).

Example 17

N-(4-amino-4'-fluorobiphenyl-3-yl)-4-(1-aminocyclopentanecarboxamido)benzamide

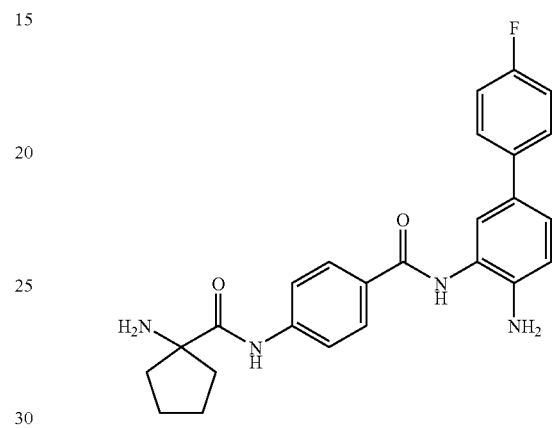

Similar procedure from Example 10 was followed to obtain the title compound using 1-tert-butoxycarbonylamino-cyclopentanecarboxylic acid and (3-amino-4'-fluoro-biphenyl-4-yl)carbamic acid tert-butyl ester. $C_{25}H_{25}N_4O_2F$ 432.9 (M+1). $^1$H NMR (400-MHz, DMSO-$d_6$): δ 9.59 (s, 1H); 7.93 (d, J=8.4 Hz, 2H); 7.76 (d, J=8.4 Hz, 2H); 7.52-7.42 (m, 3H); 7.24-7.14 (m, 3H); 6.80 (d, J=8.4 Hz, 1H); 4.97 (brs, 2H); 2.43-1.97 (m, 2H); 1.75-1.50 (m, 6H).

Example 18

4-[(1-Amino-cyclohexanecarbonyl)-amino]-N-4-amino-4'-fluoro-biphenyl-3-yl-benzamide

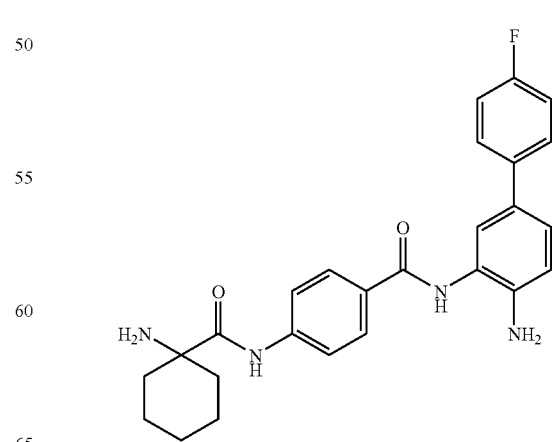

Similar procedure from Example 10 was followed to obtain the title compound using 1-tert-butoxycarbonylamino-cyclohexanecarboxylic acid and 3-amino-4'-fluorobiphenyl-4-yl-carbamic acid tert-butyl ester. $C_{26}H_{27}N_4O_2F$ 446.8 (M+1). $^1$H-NMR (400 MHz, DMSO-$d_6$): δ 9.61 (s, 1H); 7.95 (d, J=8.4 Hz, 2H); 7.78 (d, J=8.4 Hz, 2H); 7.56-7.52 (m, 2H); 7.45 (s, 1H); 7.27-7.17 (m, 3H); 6.83 (d, J=8.4 Hz, 1H); 5.04 (s, 2H); 1.83-1.77 (m, 2H); 1.57-1.45 (m, 7H); 1.21 (m, 1H).

Example 19

Biological Assays

HDAC inhibitory activity of the compound of Example 1 was measured by an assay in which HDAC-1 or -3 were used as a target molecule. The test compound was suspended in and titrated in DMSO. It was then spotted into a 384-well test plate. The enzyme, HDAC-1 or -3, was diluted in assay buffer containing 25 mM Tris-HCl (pH 8.0), 137 mM NaCl, 2.7 mM KCl, and 0.01% Tween-20 and added to the pre-spotted compound. The enzyme/compound mix was incubated at room temperature for 2 hours. The peptide substrate containing a fluorophore/quencher pair was diluted in the same assay buffer and added to the compound/enzyme mix initiating the reaction. The reaction incubated at room temperature for about 45 minutes. A concentrated developer solution was diluted in the assay buffer, and added to the reaction. The reaction was incubated at room temperature for about 15 minutes and relative fluorescence was read on an instrument reader.

The following table shows $IC_{50}$ data for the compound tested with the protocols described above.

TABLE 1

$IC_{50}$ of HDAC inhibitor compound

| Compound | HDAC-1 inhibitory activity ($IC_{50}$ [μM]) | HDAC-3 inhibitory activity ($IC_{50}$ [μM]) |
| --- | --- | --- |
| Example 1 | 0.0447 | 0.3780 |
| Example 2 | 0.0628 | 0.3780 |
| Example 3 | 0.0609 | 0.4820 |
| Example 4 | 0.0250 | 0.1710 |
| Example 5 | 0.0034 | >10.0 |
| Example 6 | 0.0074 | >10.0 |
| Example 7 | 0.0267 | >10.0 |
| Example 8 | 0.0056 | >10.0 |
| Example 9 | 0.0082 | 7.515 |
| Example 10 | 0.0052 | >10.0 |
| Example 11 | 0.0090 | >10.0 |

The assay results with HDAC-1 and -3 substrates indicate that the compounds have inhibitory activity against HDAC enzymes and thus can be useful to treat or inhibit diseases caused by abnormal activities of HDAC.

All patents and publications cited herein are incorporated by reference into this application in their entirety.

What is claimed is:

1. A compound selected from those of Formula (I) and pharmaceutically accepted salts thereof:

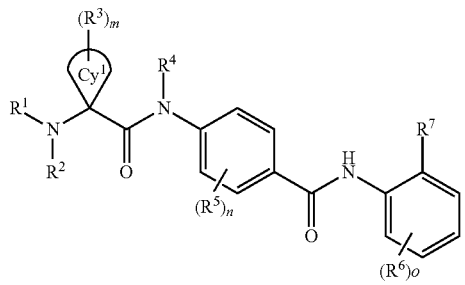

Formula (I)

wherein $Cy^1$ is cycloalkylidene or heterocycloalkylidene;

$R^1$ and $R^2$ are independently selected from the group consisting of:

(a) H, alkyl, alkenyl, alkynyl, cycloalkyl, cycloalkylalkyl, heterocyclyl, heterocyclylalkyl, aryl, and arylalkyl; and (b) $R^8$—C(O)—$X^1$—, $R^8$—O—C(O)—$X^1$— and $R^8$—S(O)$_a$—$X^1$—, wherein $X^1$ is selected from the group consisting of a bond, —NH—$C_{1-6}$ alkylene, —O—$C_{1-6}$ alkylene, $C_{1-6}$ alkylene, $C_{2-6}$ akenylene, $C_{2-6}$ alkynylene, $C_{3-6}$ cycloalkylene, arylene, and heterocyclylene;

$R^8$ is selected from the group consisting of H, hydroxy, amino, alkyl, alkoxy, N-alkylamino, N,N-dialkylamino, cycloalkyl, and heterocyclyl; and a is 0, 1 or 2;

wherein each $R^1$ and $R^2$ is optionally substituted with one or more A where such an optional substitution is chemically feasible;

$R^3$ is independently selected from the group consisting of:

(a) cyano, oxo, halo, nitro, hydroxy, amino, mercapto, alkyl, aryl, cycloalkyl, heterocyclyl, and heterocyclylalkyl;

(b) $R^9$—C(O)—$X^2$—, $R^9$—O—C(O)—$X^2$— and $R^9$—S(O)$_a$—$X^2$—, wherein $X^2$ is selected from the group consisting of a bond, —NH—$C_{1-6}$ alkylene, —O—$C_{1-6}$ alkylene, $C_{1-6}$ alkylene, $C_{2-6}$ akenylene, $C_{2-6}$ alkynylene, $C_{3-6}$ cycloalkylene, arylene, and heterocyclylene; and a is 0, 1 or 2, wherein $R^1$ is optionally substituted with one or more B where such an optional substitution is chemically feasible; or when m is 2, the two $R^1$ groups can be substituted on the same carbon ring atom of Cy and together with the carbon ring atom of Cy for in a ring situated on Cy in a spiro configuration, wherein the spiro ring is cycloalkyl or heterocycloalkyl;

two groups $R^3$ are substituted on the same carbon ring atom of $Cy^1$ and together with the carbon ring atom of $Cy^1$ form a ring situated on $Cy^1$ in a spiro configuration, wherein the spiro ring is cycloalkyl or heterocycloalkyl;

m is an integer from 0 to the maximum number of substitutable positions on $Cy^1$;

$R^4$ is selected from the group consisting of —H, alkyl, cycloalkyl, heterocycloalkyl, aryl, heteroaryl, cycloalkylalkyl, heterocycloalkylalkyl, aralkyl, heteroaralkyl, alkylamino, alkylaminoalkyl, cycloalkylamino, heterocycloalkylamino, and arylamino, wherein R⁴ is optionally substituted with one or more selected from halo, oxo, hydroxyl, amino, alkylamino, carbamoyloxy, carbamoyl, cycloalkyl, cycloalkenyl, heterocycloalkyl, aryl and heteroaryl where such an optional substitution is chemically feasible;

R⁵ is independently selected from the group consisting of halo, hydroxy, nitro, cyano, haloalkyl, haloalkoxy, amino, carboxy, carbamoyl, sulphamoyl, $C_{1-10}$ alkyl, $C_{2-10}$ alkenyl, $C_{2-10}$ alkynyl, $C_{1-10}$ alkoxy, $C_{1-10}$ alkanoyl, N—($C_{1-10}$ alkyl)amino, N,N—($C_{1-10}$ alkyl)₂ amino, $C_{1-10}$ alkanoylamino, N—($C_{1-10}$ alkyl)carbamoyl, N,N—($C_{1-10}$ alkyl)₂ carbamoyl, $C_{1-10}$ alkyl-S(O)ₐ wherein a is 0, 1 or 2, NH₂—S(O)₂NH—, N—($C_{1-10}$ alkyl)sulphamoyl, N,N—($C_{1-10}$ alkyl)₂sulphamoyl, cycloalkyl, heterocyclyl and aryl;

n is 0, 1, 2, 3 or 4;

R⁶ is independently selected from the group consisting of —H, halo, haloalkyl, aryl and heteroaryl wherein the aryl or heteroaryl is optionally substituted with one or more substituents selected from the group consisting of amino, halo, alkyl, haloalkyl, cycloalkyl, heterocycloalkyl, aryl and heteroaryl;

o is 0, 1, 2, 3 or 4;

R⁷ is NH₂— or OH—;

A is independently selected from the group consisting of oxo, halo, amino, hydroxyl, cyano, carbamoyl, $C_{1-10}$ alkyl, $C_{1-10}$ alkoxy, $C_{1-10}$ haloalkyl, $C_{1-10}$ alkanoylamino, N—($C_{1-10}$ alkyl)amino, N,N—($C_{1-10}$ dialkyl) amino, $C_{1-10}$ alkanoyl, N—($C_{1-10}$ alkyl)carbamoyl, N,N—($C_{1-10}$ dialkyl)carbamoyl, $C_{3-10}$ cycloalkyl, ($C_{3-10}$ cycloalkyl)$C_{1-10}$ alkyl, $C_{3-10}$ cycloalkoxy, $C_{1-10}$ haloalkoxy, heterocycloalkyl, (heterocycloalkyl)$C_{1-10}$ alkyl, aryl, (aryl)$C_{1-10}$ alkyl, heteroaryl, (heteroaryl)$C_{1-10}$ alkyl and R(R')(R'')silyl wherein R, R' and R'' are independently alkyl or aryl, or when R¹ or R² is a saturated or unsaturated cyclic group, two A groups can be substituted at adjacent positions of R¹ or R² and form a 5- or 6-membered, saturated or unsaturated cyclic moiety to make a fused ring with R¹ or R², wherein the cyclic moiety can contain one or more heteroatoms selected from N, O and S; and B is independently selected from the group consisting of halo, amino, carboxy, carbamoyl, $C_{1-10}$ alkyl, $C_{1-10}$ alkoxy, N—($C_{1-10}$ alkyl)amino, N,N—($C_{1-10}$ dialkyl) amino, N—($C_{1-10}$ alkyl)carbamoyl, N,N—($C_{1-10}$ dialkyl)carbamoyl, $C_{1-10}$ haloalkyl, $C_{3-10}$ cycloalkyl, $C_{3-10}$ heterocycloalkyl, $C_{3-10}$ aryl, heteroaryl, ($C_{1-10}$ alkyl)$C_{3-10}$ cycloalkyl and R(R')(R'')silyl wherein R, R' and R'' are independently alkyl or aryl.

2. The compound of claim 1, wherein Cy¹ is $C_{3-7}$ cycloalkylidene or heterocycloalkylidene having from 3 to 7 ring members.

3. The compound of claim 1, wherein R¹ and R² are independently selected from the group consisting of —H, alkyl, and carboxy, wherein each R¹ and R² is optionally substituted by one or more A selected from the group consisting of halo, hydroxy, alkyl, hydroxyalkyl, aryl, cycloalkyl, heteroaryl, heterocycloalkyl, aralkyl, cycloalkylalkyl, heterocycloalkylalkyl and heteroarylalkyl.

4. The compound of claim 1, wherein R⁴ is selected from the group consisting of methyl, cyclopropyl, cyclopropylmethyl, trifluoroethyl, N,N-dimethylaminoethyl, pyrrolidinylethyl, benzyl, pyridinylmethyl, ethylpyridinylmethyl, acetylpiperazinylethyl, methylsulfonamidoethyl, methoxyethyl, methoxycarbonylaminoethyl, pyrazinylaminoethyl, chlorofluorobenzyl, trifluoromethylpyridinylmethyl, imidazolylethyl, imidazolylmethyl, methyldioxopiperidinylmethyl, dioxopyrrolidinylethyl, N,N-dimethylcarbamoylmethyl morpholinocarbonylethyl, hydroxymethylpropyl, fluorophenyl, and tetrahydropyranyl.

5. The compound of claim 1, wherein R⁶ and R⁷ are selected to make any of the following substitutions on the phenyl ring attached to the -phenyl-C(O)—NH— linker:

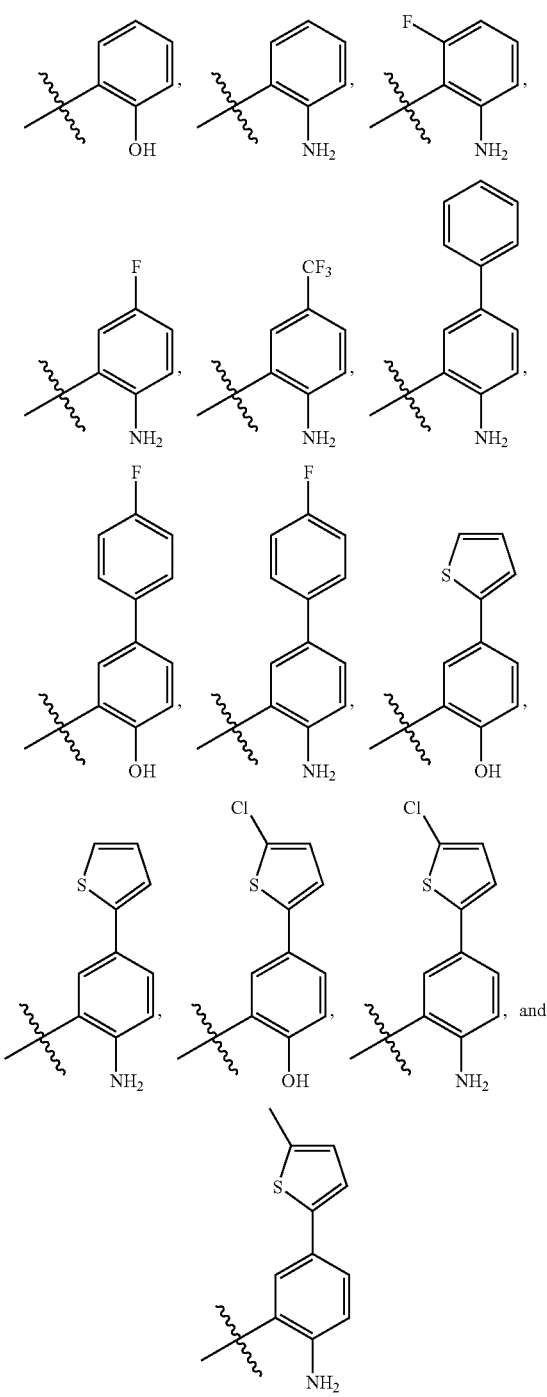

wherein the wavy line is an attachment position to the -phenyl-C(O)—NH— linker.

6. The compound of claim 1 selected from those of Formula (I-a) and pharmaceutically acceptable salts thereof:

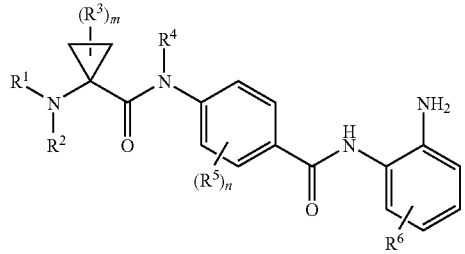

Formula (I-a)

wherein R³ is independently selected from the group consisting of halo, hydroxy, alkyl, and aryl; and m is 0, 1 or 2.

7. The compound of claim 6, wherein R¹ and R² optionally substituted with one or more A are independently selected from the group consisting of H, methyl, butyl, tetrahydrofuranylmethyl, alkylazetidinyl, alkylpiperidinyl, cyclopentyl, oxoimidazolidinylethyl, alkyloxopiperidinyl, trifluorophenylethyl, trifluoropyridinylethyl, alkylphenylcyclopropyl, hydroxy, trifluoromethylpentynyl, cyclopropylpropynyl, hydroxybutynyl, methylcyclopropoxycarbonyl, tert-butoxycarbonyl, trifluoromethylpropoxycarbonyl, benzoxycarbonyl, pyridinylmethoxycarbonyl, trifluoromethylpyridinylmethoxycarbonyl, cyclopropylpyridinylmethoxycarbonyl, phenylethoxycarbonyl, quinolinylmethoxycarbonyl, morpholinoethoxycarbonyl, N,N-dimethylcarbamoyl, morpholinylcarbonyl, N-t-butylcarbamoyl, benzenoyl, nicotinoyl, quinolinoyl, cyclopropanoyl, propanoyl, isobutanoyl, methoxypropanoyl, dimethylaminopropanoyl, trifluoroethyl, trifluoropropyl, trifluoromethylcyclopropyl, methylsulfonyl, trifluoroethylsulfonyl, cyclopropylsulfonyl, phenylsulfonyl, pyridinylsulfonyl, trifluoromethylpyridinylsulfonyl, quinolinylsulfonyl, sulfalmoyl, dimethylsulfamoyl, morpholinylsulfonyl, aminothiadiazolylethyl, tetrahydropyranylethyl, thiophenylethyl,

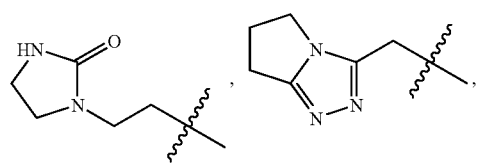

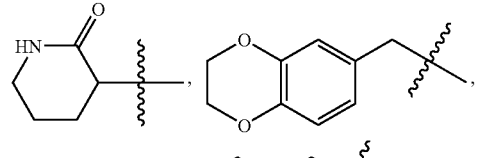

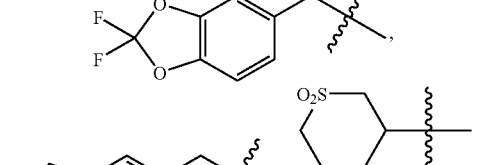

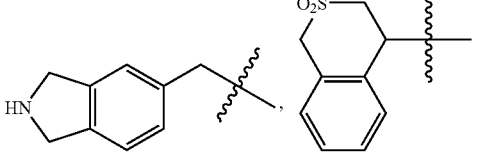

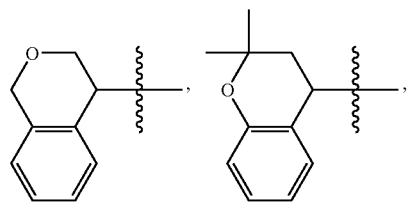

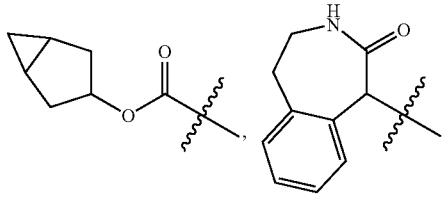

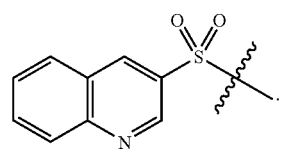

8. The compound of claim 6, wherein R¹ is —H; and R² is R¹⁰—O—C(O)—X³—, wherein R² is optionally substituted with one or more A.

9. The compound of claim 6, wherein R⁴ is selected from methyl, cyclopropyl, cyclopropylmethyl, trifluoroethyl, N,N-dimethylaminoethyl, pyrrolidin-1-ylethyl, benzyl, pyridin-2-ylmethyl, (1-ethylpyridin-4-yl)methyl, 4-acetylpiperazin-1-ylethyl, methylsulfonamidoethyl, methoxyethyl, methoxycarbonylaminoethyl, pyrazin-2-ylaminoethyl, 2-chloro-4-fluoro-benzyl, (5-(trifluoromethyl)pyridin-2-yl)methyl, (1H-imidazol-1-yl)ethyl, (1H-imidazol-2-yl)methyl, (1-methyl-2,6-dioxopiperidin-4-yl)methyl, 2,5-dioxopyrrolidin-1-ylethyl, N,N-dimethylcarbamoyl, morpholinocarbonylmethyl, 2-hydroxy-2-methylpropyl, 4-fluorophenyl, and tetrahydro-2H-pyran-4-yl.

10. The compound of claim 6, wherein R⁵ is selected from halo, hydroxy, alkyl and haloalkyl.

11. The compound of claim 6, wherein R⁶ is selected from fluoro, trifluoromethyl, phenyl, fluorophenyl, thiophenyl, chlorothiophenyl and methylthiophenyl.

12. The compound of claim 6, which is selected from the group consisting of

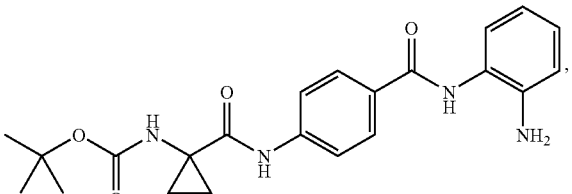

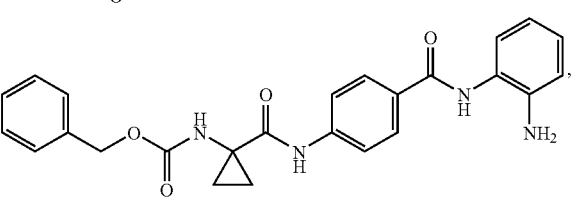

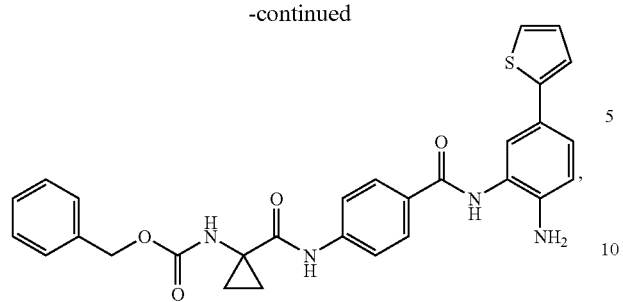

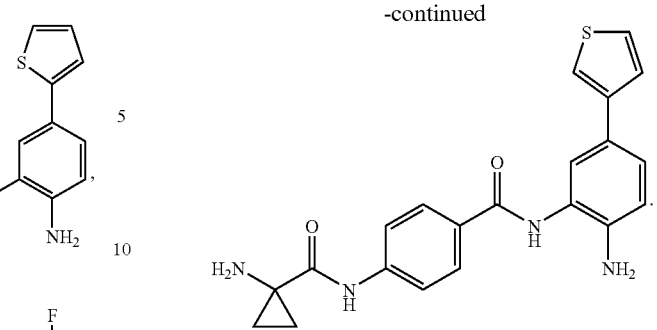

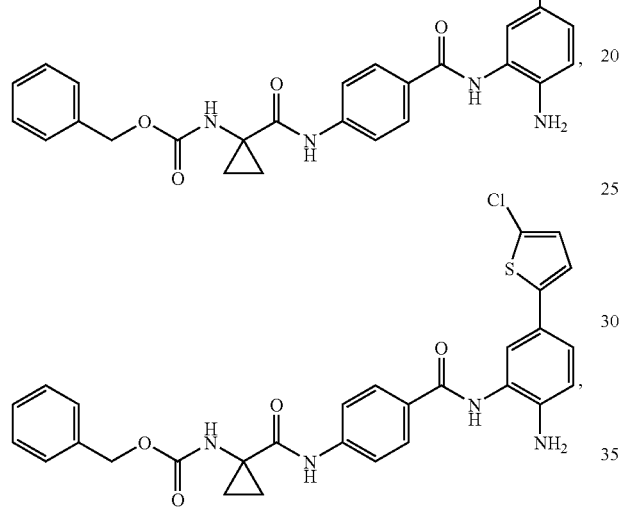

13. The compound of claim 1 selected from those of Formula (I-b) and pharmaceutically acceptable salts thereof:

Formula (I-b)

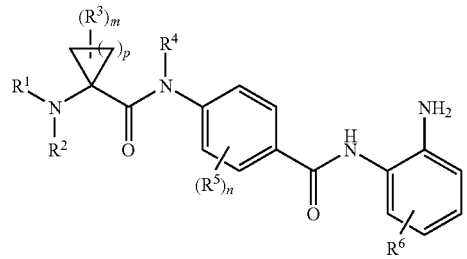

wherein R³ is independently selected from the group consisting of halo, hydroxy, alkyl, and aryl; and p is 2, 3, 4 or 5.

14. The compound of claim 13, wherein R¹ and R² are independently selected from the group consisting of H, methyl, tert-butyl, (6,7-dihydro-5H-pyrrolo[2,1-c][1,2,4]triazol-3-yl)methyl, (2,3-dihydrobenzo[b][1,4]dioxin-6-yl)methyl, (2,2-difluorobenzo[d][1,3]dioxol-5-yl)methyl, tetrahydrofuran-2-ylmethyl, 2-alkylisoindolin-5-ylmethyl, 1-alkylazetidin-3-yl, 1-alkylpiperidin-3-yl, 1-alkylpyrrolidin-2-yl, cyclopentyl, 2-oxoimidazolidin-1-ylethyl, isochroman-4-yl, 2,2-dimethylchroman-4-yl, 1-alkyl-2-oxopiperidin-3-yl, 2,2,2-trifluoro-1-phenylethyl, 2,2,2-trifluoro-1-(pyridin-2-yl)ethyl, 1-alkylphenylcyclopropyl, 5,5,5-trifluoro-4-hydroxy-4-(trifluoromethyl)pent-2-ynyl, 3-cyclopropylprop-2-ynyl, 4-hydroxy-4-methylpent-2-ynyl, 1-methylcyclopropoxycarbonyl, tert-butoxycarbonyl, 1,1,1-trifluoro-2-methylprop-2-oxycarbonyl, benzoxycarbonyl, pyridin-3-ylmethoxycarbonyl, 5-trifluoromethylpyridin-3-ylmethoxycarbonyl, 5-cyclopropylpyridin-3-ylmethoxycarbonyl, 1-phenylethoxycarbonyl, quinolin-3-ylmethoxycarbonyl, 2-morpholinoethoxycarbonyl, N,N-dimethylcarbamoyl, morpholin-4-ylcarbonyl, N-t-butylcarbamoyl, benzenoyl, nicotinoyl, quinolinoyl, cyclopropanoyl, propanoyl, isobutanoyl, methoxypropanoyl, N,N-dimethylaminopropanoyl, 2,2,2-trifluoroethyl, 1,1,1-trifluoroprop-2-yl, 1-trifluoromethylcyclopropyl, methylsulfonyl, 2,2,2-trifluoroethylsulfonyl, cyclopropylsulfonyl, phenylsulfonyl, pyridin-3-ylsulfonyl, 5-trifluoromethylpyridin-3-ylsulfonyl, quinoline-3-sulfonyl, sulfalmoyl, dimethylsulfamoyl, morpholin-4-ylsulfonyl, 2-oxo-2,3,4,5-tetrahydro-1H-benzo[d]azepin-1-yl, 1-(carboxymethyl)-2-oxo-piperidin-3-yl, 2-(5-amino-1,3,4-thiadiazol-2-yl)ethyl, 2-(tetrahydro-2H-pyran-2-yl)ethyl, and 2-(thiophen-2-yl)ethyl, wherein each of R¹ and R² is optionally substituted by one or more A.

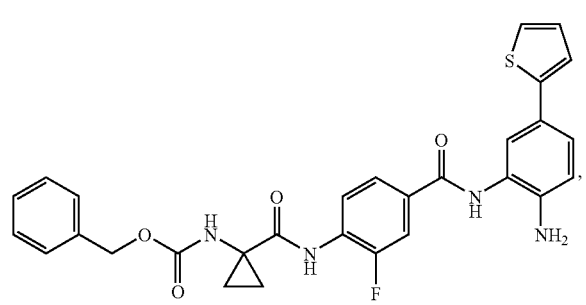

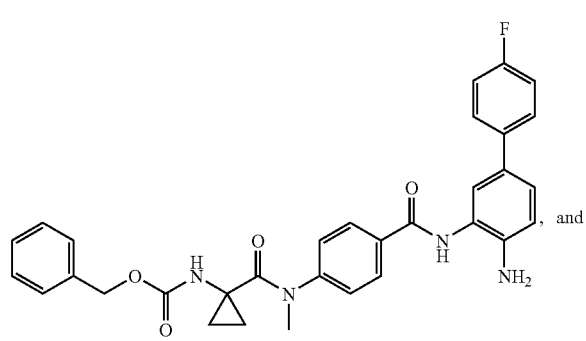

15. The compound of claim 13, wherein $R^1$ is —H; and $R^2$ is $R^{10}$—O—C(O)—$X^3$— wherein $R^2$ is optionally substituted with one or more A.

16. The compound of claim 13, wherein $R^4$ is selected from methyl, cyclopropyl, cyclopropylmethyl, trifluoroethyl, N,N-dimethylaminoethyl, pyrrolidin-1-ylethyl, benzyl, pyridin-2-ylmethyl, (1-ethylpyridin-4-yl)methyl, 4-acetylpiperazin-1-ylethyl, methylsulfonamidoethyl, methoxyethyl, methoxycarbonylaminoethyl, pyrazin-2-ylaminoethyl, 2-chloro-4-fluoro-benzyl, (5-(trifluoromethyl)pyridin-2-yl)methyl, (1H-imidazol-1-yl)ethyl, (1H-imidazol-2-yl)methyl, (1-methyl-2,6-dioxopiperidin-4-yl)methyl, 2,5-dioxopyrrolidin-1-ylethyl, N,N-dimethylcarbamoyl, morpholinocarbonylmethyl, 2-hydroxy-2-methylpropyl, 4-fluorophenyl, and tetrahydro-2H-pyran-4-yl.

17. The compound of claim 13, wherein $R^5$ is selected from halo, hydroxy, alkyl and haloalkyl.

18. The compound of claim 13, wherein $R^6$ is selected from fluoro, trifluoromethyl, phenyl, fluorophenyl, thiophenyl, chlorothiophenyl and methylthiophenyl.

19. The compound of claim 13, which is selected from the group consisting of

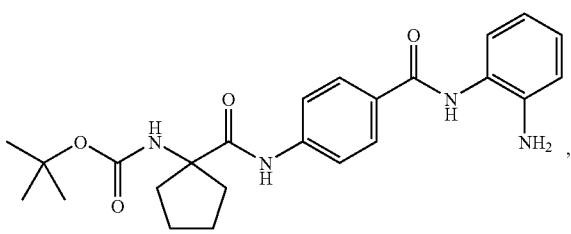

,

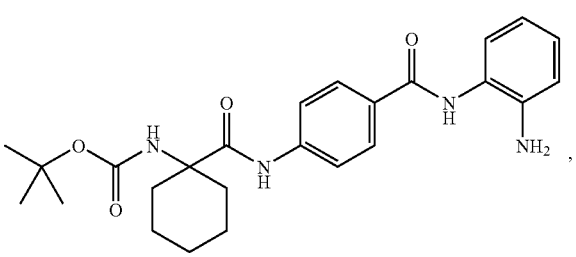

,

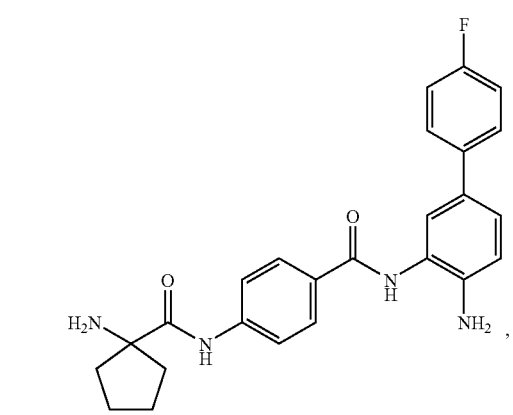

,

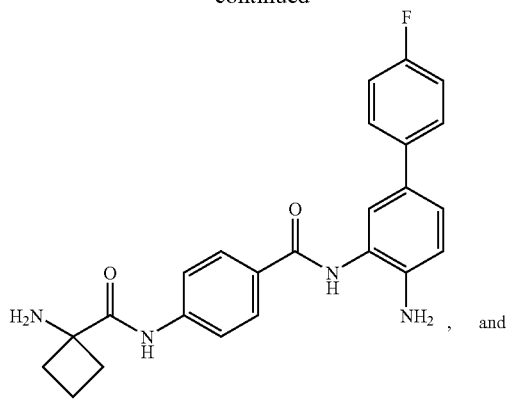

, and

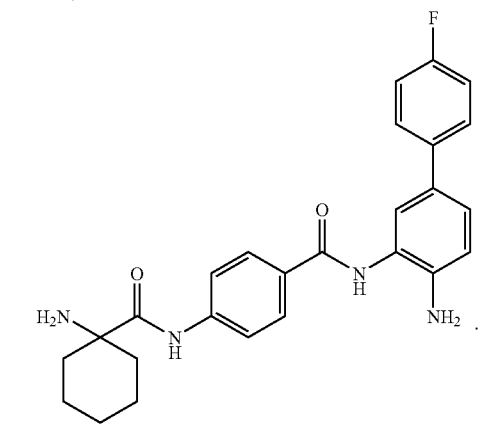

.

20. The compound of claim 1 selected from those of Formula (I-c) and pharmaceutically acceptable salts thereof:

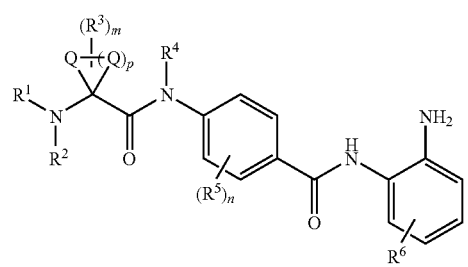

Formula (I-c)

wherein p is 2, 3, 4 or 5, and Q is independently selected from the group consisting of —CH$_2$—, —NH—, —O— and —S—, wherein at least one Q is a non-carbon ring atom.

$R^3$ is independently selected from the group consisting of halo, hydroxy, alkyl, and aryl;

$R^5$ is independently selected from the group consisting of halo, hydroxy, haloalkyl, haloalkoxy, amino, carboxy, $C_{1-10}$ alkyl, $C_{1-10}$ alkoxy, $C_{1-10}$ alkanoyl, N—($C_{1-10}$ alkyl)amino, and N,N—($C_{1-10}$ alkyl)$_2$ amino; and p is 1, 2, 3, 4 or 5.

21. The compound of claim 20, wherein $R^1$ and $R^2$ are independently selected from the group consisting of H, methyl, tert-butyl, (6,7-dihydro-5H-pyrrolo[2,1-c][1,2,4]triazol-3-yl)methyl, (2,3-dihydrobenzo[b][1,4]dioxin-6-yl)methyl, (2,2-difluorobenzo[d][1,3]dioxol-5-yl)methyl, tetrahydrofuran-2-ylmethyl, 2-alkylisoindolin-5-ylmethyl, 1-alkylazetidin-3-yl, 1-alkylpiperidin-3-yl, 1-alkylpyrrolidin-2-yl, cyclopentyl, 2-oxoimidazolidin-1-ylethyl, isochroman-4-yl, 2,2-dimethylchroman-4-yl, 1-alkyl-2-oxopiperidin-3-yl, 2,2,2-trifluoro-1-phenylethyl, 2,2,2-trifluoro-1-(pyridin-2-yl)ethyl, 1-alkylphenylcyclopropyl, 5,5,5-trifluoro-4-hydroxy-4-(trifluoromethyl)pent-2-ynyl, 3-cyclopropylprop-2-ynyl, 4-hydroxy-4-methylpent-2-ynyl, 1-methylcyclopropoxycarbonyl, tert-butoxycarbonyl, 1,1,1-trifluoro-2-methylprop-2-oxycarbonyl, benzoxycarbonyl, pyridin-3-ylmethoxycarbonyl, 5-trifluoromethylpyridin-3-ylmethoxycarbonyl, 5-cyclopropylpyridin-3-ylmethoxycarbonyl, 1-phenylethoxycarbonyl, quinolin-3-ylmethoxycarbonyl, 2-morpholinoethoxycarbonyl, N,N-dimethylcarbamoyl, morpholin-4-ylcarbonyl, N-t-butylcarbamoyl, benzenoyl, nicotinoyl, quinolinoyl, cyclopropanoyl, propanoyl, isobutanoyl, methoxypropanoyl, N,N-dimethylaminopropanoyl, 2,2,2-trifluoroethyl, 1,1,1-trifluoroprop-2-yl, 1-trifluoromethylcyclopropyl, methylsulfonyl, 2,2,2-trifluoroethylsulfonyl, cyclopropylsulfonyl, phenylsulfonyl, pyridin-3-ylsulfonyl, 5-trifluoromethylpyridin-3-ylsulfonyl, quinoline-3-sulfonyl, sulfalmoyl, dimethylsulfamoyl, morpholin-4-ylsulfonyl, 2-oxo-2,3,4,5-tetrahydro-1H-benzo[d]azepin-1-yl, 1-(carboxymethyl)-2-oxo-piperidin-3-yl, 2-(5-amino-1,3,4-thiadiazol-2-yl)ethyl, 2-(tetrahydro-2H-pyran-2-yl)ethyl, and 2-(thiophen-2-yl)ethyl, wherein each of $R^1$ and $R^2$ is optionally substituted by one or more A.

22. The compound of claim 20, wherein $R^1$ is —H; and $R^2$ is $R^{10}$—O—C(O)—$X^3$—, wherein $R^2$ is optionally substituted with one or more A.

23. The compound of claim 20, wherein $R^4$ is selected from methyl, cyclopropyl, cyclopropylmethyl, trifluoroethyl, N,N-dimethylaminoethyl, pyrrolidin-1-ylethyl, benzyl, pyridin-2-ylmethyl, (1-ethylpyridin-4-yl)methyl, 4-acetylpiperazin-1-ylethyl, methylsulfonamidoethyl, methoxyethyl, methoxycarbonylaminoethyl, pyrazin-2-ylaminoethyl, 2-chloro-4-fluoro-benzyl, (5-(trifluoromethyl)pyridin-2-yl)methyl, (1H-imidazol-1-yl)ethyl, (1H-imidazol-2-yl)ethyl, (1-methyl-2,6-dioxopiperidin-4-yl)methyl, 2,5-dioxopyrrolidin-1-ylethyl, N,N-dimethylcarbamoyl, morpholinocarbonylmethyl, 2-hydroxy-2-methylpropyl, 4-fluorophenyl, and tetrahydro-2H-pyran-4-yl.

24. The compound of claim 20, wherein $R^5$ is selected from halo, hydroxy, alkyl and haloalkyl.

25. The compound of claim 20, wherein $R^6$ is selected from fluoro, trifluoromethyl, phenyl, fluorophenyl, thiophenyl, chlorothiophenyl and methylthiophenyl.

26. The compound of claim 20, which is selected from the group consisting of

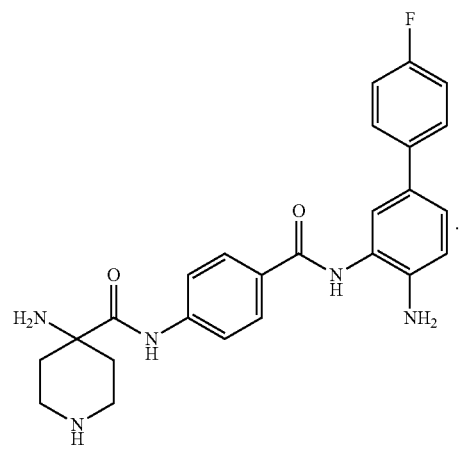

27. A pharmaceutical composition comprising an effective amount of one or more compounds according to claim 1 and a pharmaceutically-acceptable carrier.

28. The pharmaceutical composition according to claim 27, further comprising one or more anti-cancer agents.

29. The pharmaceutical composition according to claim 28, wherein the one or more anti-cancer agents are selected from the group consisting of cyclophosphamide, dacarbazine, cisplatin, methotrexate, mercaptopurine, thioguanine, fluorouracil, cytarabine, vinblastine, paclitaxel, doxorubicin, bleomycin, mitomycin, prednisone, tamoxifen, flutamide, asparaginase, rituximab, trastuzumab, imatinib, retinoic acid, colony-stimulating factor, amifostine, lenalidomide, HDAC inhibitor, CDK inhibitor, camptothecin and topotecan.

30. A method of inhibiting or treating a disease arising from abnormal cell proliferation and/or differentiation in an animal, comprising administering to said animal a therapeutically effective amount of one or more compounds according to claim 1 or 28.

31. The method according to claim 30, wherein the animal is human.

32. The method according to claim 30, wherein the disease is mediated by a histone deacetylase.

33. The method according to claim 30, wherein the disease is selected from the group consisting of a cell proliferative disease, autosomal dominant disorder, genetic related metabolic disorder, fibrosis, autoimmune disease, diabetes, neurological disease, and Alzheimer's disease.

34. The method according to claim 30, wherein the disease is cancer selected from the group consisting of bladder cancer, breast cancer, colon cancer, rectal cancer, endometrial cancer, kidney cancer, leukemia, lung cancer, melanoma, non-Hodgkin's lymphoma, pancreatic cancer, prostate cancer, skin cancer and thyroid cancer.

35. The method according to claim 30, wherein the disease is pulmonary fibrosis or renal fibrosis.

* * * * *